US009631170B2

(12) United States Patent
Herbert et al.

(10) Patent No.: US 9,631,170 B2
(45) Date of Patent: Apr. 25, 2017

(54) GENETICALLY INDUCIBLE HYDROGEN PEROXIDE RESISTANCE AND PRODUCTION

(71) Applicant: University of Wyoming, Laramie, WY (US)

(72) Inventors: Stephen K. Herbert, Laramie, WY (US); Levi G. Lowder, Laramie, WY (US)

(73) Assignee: University of Wyoming, Laramie, WY (US)

( * ) Notice: Subject to any disclaimer, the term of this patent is extended or adjusted under 35 U.S.C. 154(b) by 326 days.

(21) Appl. No.: 14/348,994

(22) PCT Filed: Oct. 4, 2012

(86) PCT No.: PCT/US2012/058756
§ 371 (c)(1),
(2) Date: Apr. 1, 2014

(87) PCT Pub. No.: WO2013/052669
PCT Pub. Date: Apr. 11, 2013

(65) Prior Publication Data
US 2014/0302583 A1  Oct. 9, 2014

Related U.S. Application Data

(60) Provisional application No. 61/544,165, filed on Oct. 6, 2011.

(51) Int. Cl.
| | |
|---|---|
| *C12N 9/08* | (2006.01) |
| *C12Q 1/68* | (2006.01) |
| *C12N 1/20* | (2006.01) |
| *C12N 15/00* | (2006.01) |
| *C07H 21/04* | (2006.01) |
| *C12N 1/12* | (2006.01) |
| *C12N 15/11* | (2006.01) |
| *A01G 33/00* | (2006.01) |
| *A01H 13/00* | (2006.01) |
| *C12N 15/79* | (2006.01) |
| *C12N 15/82* | (2006.01) |
| *C12N 9/02* | (2006.01) |
| *C12N 15/74* | (2006.01) |

(52) U.S. Cl.
CPC .............. *C12N 1/12* (2013.01); *A01G 33/00* (2013.01); *A01H 13/00* (2013.01); *C12N 1/20* (2013.01); *C12N 9/0036* (2013.01); *C12N 9/0065* (2013.01); *C12N 9/0089* (2013.01); *C12N 15/11* (2013.01); *C12N 15/74* (2013.01); *C12N 15/79* (2013.01); *C12N 15/8271* (2013.01); *C12Y 111/01006* (2013.01)

(58) Field of Classification Search
CPC .................................................. C12N 15/11
See application file for complete search history.

(56) References Cited

U.S. PATENT DOCUMENTS

| | | | |
|---|---|---|---|
| 5,582,732 A | 12/1996 | Mao et al. |
| 6,235,196 B1 | 5/2001 | Zhou et al. |
| 6,592,763 B1 | 7/2003 | Benedictus et al. |
| 6,613,222 B2 | 9/2003 | Mikkelson et al. |
| 7,097,762 B1 | 8/2006 | Ruocco et al. |
| 7,135,115 B2 | 11/2006 | Langlais et al. |
| 2008/0009444 A1 | 1/2008 | Nash et al. |
| 2008/0176299 A1 | 7/2008 | Dicosimo et al. |
| 2008/0233623 A1 | 9/2008 | Chang et al. |
| 2009/0203070 A1 | 8/2009 | Devroe et al. |
| 2011/0136197 A1 | 6/2011 | Dodge et al. |

FOREIGN PATENT DOCUMENTS

| | | | |
|---|---|---|---|
| EP | 00695722 A1 | | 2/1996 |
| EP | 01960316 B1 | | 8/2009 |
| WO | WO 2008/073139 | * | 6/2008 |
| WO | 2009050661 A2 | | 4/2009 |
| WO | 2010108087 A2 | | 9/2010 |
| WO | 2010144336 A2 | | 12/2010 |

OTHER PUBLICATIONS

Mulvey et al. Regulation of Transcription of katE and katF in *Escherichia coli*. Journal of Bacteriology, Dec. 1990, p. 6713-6720.*
Branden et al. Introduction to Protein Structure, Garland Publishing Inc., New York, p. 247, 1991.*
Strydom, JP., Britz, TJ., and Mostert, JF., Two-phase anaerobic digestion of three different dairy effluents using a hybrid bioreactor, Water SA, 1997, pp. 151-156, vol. 23:2, Pretoria.
Arnold, RS., et al., Hydrogen peroxide mediates the cell growth and transformation caused by the mitogenic oxidase Nox1, PNAS, 2001, pp. 5550-5555, vol. 98:10.
Chen, Xiangning and Widger, William R., Physical Genome Map of the Unicellular *Cyanobacteriunn synechococcus* sp. Strain PCC 7002, Journal of Bateriology, 1993, pp. 5106-5116, vol. 175:16.
Moriyama, T., et al., Characterization of cell-cycle-driven and light-driven gene expression in a synchronous culture system in the unicellular rhodophyte Cyanidioschyzon merolae, Microbiology, 2010, pp. 1730-1737, vol. 156.
PCT/U52012/058756—International Search Report and Written Opinion, Feb. 25, 2013.
Shukla, P. and Sullivan J.M., Normal and Mutant Rhodopsin Activation Measured with the Early Receptor Current in a Unicellular Expression System, J. Gen. Physiol., 1999, pp. 609-636, vol. 114:5.

* cited by examiner

*Primary Examiner* — Yong Pak
(74) *Attorney, Agent, or Firm* — Cochran Freund & Young LLC; James M. Weatherly

(57) ABSTRACT

DNA constructs as well as methods for the production of unicellular organisms capable of producing hydrogen peroxide resistance proteins are disclosed. DNA constructs as well as methods for integration of the DNA constructs into the genomes of unicellular organisms for the expression of hydrogen peroxide production proteins are also disclosed. In addition, DNA constructs as well as methods for integration of the DNA constructs into the genomes of unicellular organisms for the expression of hydrogen peroxide resistance and hydrogen peroxide production proteins are disclosed.

18 Claims, 11 Drawing Sheets

SEQUENCE LISTING

```
<160> NUMBER OF SEQ ID NOS: 17

<210> SEQ ID NO 1
<211> LENGTH: 4270
<212> TYPE: DNA
<213> ORGANISM: Homo sapiens

<400> SEQUENCE: 1
tgagtgggca gagctgaccc ggtgcgggtg ggagtcaggg cgcccggaaa acccggctct      60
gggtagcaga ccccgcccgg gctggctcgg cgccgggcct tcgggcttcc actcagtctt     120
tgaccctcgg tcctcgctca gcggcccggc aggccgcaca actgtaaccg ctgccccggc     180
cgccgcccgc tccttctcgg tccggcgggc acagagcgca gcgcggcggg gccggcggca     240
tggctgtgtc ctggaggagc tggctcgcca acgaaggggg taaacacctc tgcctgttca     300
tctggctctc catgaatgtc ctgcttttct ggaaaacctt cttgctgtat aaccaagggc     360
cagagtatca ctacctccac cagatgttgg ggctaggatt gtgtctaagc agagcctcag     420
catctgttct taacctcaac tgcagcctta tccttttacc catgtgccga acactcttgg     480
cttacctccg aggatcacag aaggttccaa gcaggagaac caggagattg ttggataaaa     540
gcagaacatt ccatattacc tgtggtgtta ctatctgtat tttctcaggc gtgcatgtgg     600
ctgcccatct ggtgaatgcc ctcaacttct cagtgaatta cagtgaagac tttgttgaac     660
tgaatgcagc aagataccga gatgaggatc ctagaaaact tctcttcaca actgttcctg     720
gcctgacagg ggtctgcatg gtggtggtgc tattcctcat gatcacagcc tctacatatg     780
caataagagt ttctaactat gatatcttct ggtatactca taacctcttc tttgtcttct     840
acatgctgct gacgttgcat gtttcaggag ggctgctgaa gtatcaaact aatttagata     900
cccaccctcc cggctgcatc agtcttaacc gaaccagctc tcagaatatt tccttaccag     960
agtatttctc agaacatttt catgaacctt tccctgaagg attttcaaaa ccggcagagt    1020
ttacccagca caaatttgtg aagatttgta tggaagagcc cagattccaa gctaattttc    1080
cacagacttg gctttggatt tctggacctt tgtgcctgta ctgtgccgaa agactttaca    1140
ggtatatccg gagcaataag ccagtcacca tcatttcggt cataagtcat ccctcagatg    1200
tcatggaaat ccgaatggtc aaagaaaatt ttaaagcaag acctggtcag tatattactc    1260
tacattgtcc cagtgtatct gcattagaaa atcatccatt taccctcaca atgtgtccaa    1320
ctgaaaccaa agcaacattt ggggttcatc ttaaaatagt aggagactgg acagaacgat    1380
ttcgagattt actactgcct ccatctagtc aagactccga aattctgccc ttcattcaat    1440
ctagaaatta tcccaaggat gactggaaac catacaagct tagaagacta tactttattt    1500
gggtatgcag agatatccag tccttccgtt ggtttgcaga tttactctgt atgttgcata    1560
acaagttttg gcaagagaac agacctgact atgtcaacat ccagctgtac ctcagtcaaa    1620
cagatgggat acagaagata attggagaaa atatcatgc actgaattca agactgttta    1680
taggacgtcc tcggtggaaa cttttgtttg atgaaatagc aaaatataac agaggaaaaa    1740
cagttggtgt tttctgttgt ggacccaatt cactatccaa gactcttcat aaactgagta    1800
accagaacaa ctcatatggg acaagatttg aatacaataa agagtctttc agctgaaaac    1860
ttttgccatg aagcaggact ctaaagaagg aatgagtgca atttctaaga ctttgaaact    1920
```

| | | | | |
|---|---|---|---|---|
| cagcggaatc | aatcagctgt | gttatgccaa | agaatagtaa | ggttttctta tttatgatta | 1980 |
| tttaaaatgg | aaatgtgaga | atgtggcaag | atgaccgtca | cattacatgt ttaatctgga | 2040 |
| aaccaaagag | accctgaaga | atatttgatg | tgatgattca | cttttcagtt ctcaaattaa | 2100 |
| aagaaaactg | ttagatgcac | actgttgatt | ttcatggtgg | attcaagaac tccctagtga | 2160 |
| ggagctgaac | ttgctcaatc | taaggctgat | tgtcgtgttc | ctctttaaat tgttttggt | 2220 |
| tgaacaaatg | caagattgaa | caaaattaaa | aattcattga | agctgaaatt ccattttctg | 2280 |
| tgttgtgtat | aaacagagta | gctttaattt | gcaagcactc | caggcaaata tattagatgt | 2340 |
| ttgaaaacac | agcacaagac | tctgtattga | tacgggtact | ttgtgtcaat atctaatcgt | 2400 |
| ctccactact | tatgctaata | cctctatttg | atatctgaag | actatatgct aactgaacct | 2460 |
| tcctcaaatg | ttgttatagt | atctattttt | atatatttt | ttcttttat tcctctctct | 2520 |
| agggaaatat | gccttccctt | agcatgcatt | agacataatg | atttaatagg tccctttcat | 2580 |
| cttcatttaa | atctatcact | attgcatggt | aatgaaaata | ttcctactat aaattataaa | 2640 |
| gggatatata | tatgggata | tatatatgta | tatacacata | tatatataca cacacacaca | 2700 |
| catatatata | tatatatata | tatatacaca | tatactaata | acttttccct tttttcagca | 2760 |
| tttttgtctc | tattattatt | attgttttt | tcccaggtag | ggtttgtctt aggctgtagc | 2820 |
| ctctaaggat | agttagttaa | tttgcacttt | gagaccaaag | acatcatgt gtgtcagtag | 2880 |
| ggactgaata | taagatttat | ctcctttgcc | acacattggt | ttatgatgga gacattgaaa | 2940 |
| gtctagtcat | attcctgaac | agtaaaacct | gtattttacc | ttttaagtaa gaggaaatat | 3000 |
| gatattctta | ttcaaactta | agtttagaat | ccagaatatt | actgtcgcac tttttggtat | 3060 |
| cctgagtttc | catagggaac | tattgggttt | aaagtcaccg | ttggaactac actgtgtgat | 3120 |
| cttataaact | tatgttccct | ggctatcata | ttcttggctc | agaacaatat ttcccattac | 3180 |
| tatcttaaga | attaaggcat | tcatggctca | cgcctgtaat | cccggcactt tgggaggcca | 3240 |
| aggcaggtgg | atcacgaggt | cagagttcaa | gaccagcctg | accaagttgg tgaaacccca | 3300 |
| tcgctactaa | aaatacaaat | attaggcggg | tgtggtggcg | ggtgcctata atcccaacta | 3360 |
| ctcgggagac | tgaggcaaag | aatcgcttga | acccggtggg | cggaggttgc agtgagccaa | 3420 |
| gattgcacca | ctgcactcca | gcctgggtga | cagagcaaga | ttccatctca aaaaaaaaa | 3480 |
| aaaaaaaaa | aaaaagaat | taaagcattc | atacagttta | gtgattttgt ttagtagtcg | 3540 |
| gctatcaatt | gctatcaaat | ataacactgc | tgaaatcagc | agtgtgactt accttgccat | 3600 |
| tgttaaaatg | ttacataaaa | cataacatga | tagatgctaa | ggccttttt tgctataatt | 3660 |
| caccaatagc | aatcaagcat | gctaacccat | actgaatgat | atttacttgt agatatttct | 3720 |
| tccttccctt | gaaattctcc | tttctatgga | agaagatga | acccaaaaaa gtgataggaa | 3780 |
| atgtggaatg | ctcatgcaga | tttagctctg | aaggcatatt | taataactag tatgtcttga | 3840 |
| caacagtctt | tagattaaaa | agaattttca | tggaaacatt | taacagaaag aactagtaaa | 3900 |
| aagacactt | gagttagtcc | aggcttaatg | tgcaatactg | actctatact gatcataatt | 3960 |
| tatttatgcg | atcatattaa | tagacctaat | ttcattaaaa | caggtagaag attttttcaaa | 4020 |
| agaaagatga | tgtttcaaag | ctggtctgcc | attctagatg | agcctccttg cttatttaag | 4080 |
| ttccagtagg | tgttcaaatg | ttaaatgtta | aacataggtc | atctttgctt ctgcagggct | 4140 |
| tcatcttgca | tgtttaagag | aactttgttt | tattttgagg | gattatttct ctggggatca | 4200 |
| ttcttataat | acaagcctta | aatcactaat | tttagtagca | ataaatgtta aaattgaaaa | 4260 | aaaaaaaaaa                                                                  4270

<210> SEQ ID NO 2
<211> LENGTH: 538
<212> TYPE: PRT
<213> ORGANISM: Homo sapiens

<400> SEQUENCE: 2

Met Ala Val Ser Trp Arg Ser Trp Leu Ala Asn Glu Gly Val Lys His
1               5                   10                  15

Leu Cys Leu Phe Ile Trp Leu Ser Met Asn Val Leu Leu Phe Trp Lys
            20                  25                  30

Thr Phe Leu Leu Tyr Asn Gln Gly Pro Glu Tyr His Tyr Leu His Gln
        35                  40                  45

Met Leu Gly Leu Gly Leu Cys Leu Ser Arg Ala Ser Ala Ser Val Leu
    50                  55                  60

Asn Leu Asn Cys Ser Leu Ile Leu Leu Pro Met Cys Arg Thr Leu Leu
65                  70                  75                  80

Ala Tyr Leu Arg Gly Ser Gln Lys Val Pro Ser Arg Arg Thr Arg Arg
                85                  90                  95

Leu Leu Asp Lys Ser Arg Thr Phe His Ile Thr Cys Gly Val Thr Ile
            100                 105                 110

Cys Ile Phe Ser Gly Val His Val Ala Ala His Leu Val Asn Ala Leu
        115                 120                 125

Asn Phe Ser Val Asn Tyr Ser Glu Asp Phe Val Glu Leu Asn Ala Ala
    130                 135                 140

Arg Tyr Arg Asp Glu Asp Pro Arg Lys Leu Leu Phe Thr Thr Val Pro
145                 150                 155                 160

Gly Leu Thr Gly Val Cys Met Val Val Leu Phe Leu Met Ile Thr
                165                 170                 175

Ala Ser Thr Tyr Ala Ile Arg Val Ser Asn Tyr Asp Ile Phe Trp Tyr
            180                 185                 190

Thr His Asn Leu Phe Phe Val Phe Tyr Met Leu Leu Thr Leu His Val
        195                 200                 205

Ser Gly Gly Leu Leu Lys Tyr Gln Thr Asn Leu Asp Thr His Pro Pro
    210                 215                 220

Gly Cys Ile Ser Leu Asn Arg Thr Ser Ser Gln Asn Ile Ser Leu Pro
225                 230                 235                 240

Glu Tyr Phe Ser Glu His Phe His Glu Pro Phe Pro Glu Gly Phe Ser
                245                 250                 255

Lys Pro Ala Glu Phe Thr Gln His Lys Phe Val Lys Ile Cys Met Glu
            260                 265                 270

Glu Pro Arg Phe Gln Ala Asn Phe Pro Gln Thr Trp Leu Trp Ile Ser
        275                 280                 285

Gly Pro Leu Cys Leu Tyr Cys Ala Glu Arg Leu Tyr Arg Tyr Ile Arg
    290                 295                 300

Ser Asn Lys Pro Val Thr Ile Ile Ser Val Ile Ser His Pro Ser Asp
305                 310                 315                 320

Val Met Glu Ile Arg Met Val Lys Glu Asn Phe Lys Ala Arg Pro Gly
                325                 330                 335

Gln Tyr Ile Thr Leu His Cys Pro Ser Val Ser Ala Leu Glu Asn His
            340                 345                 350

Pro Phe Thr Leu Thr Met Cys Pro Thr Glu Thr Lys Ala Thr Phe Gly
        355                 360                 365

| | | | | | | | | | | | |
|---|---|---|---|---|---|---|---|---|---|---|---|
| Val | His | Leu | Lys | Ile | Val | Gly | Asp | Trp | Thr | Glu | Arg | Phe | Arg | Asp | Leu |
| 370 | | | | 375 | | | | | 380 | | |

Val His Leu Lys Ile Val Gly Asp Trp Thr Glu Arg Phe Arg Asp Leu
370             375                 380

Leu Leu Pro Pro Ser Ser Gln Asp Ser Glu Ile Leu Pro Phe Ile Gln
385             390                 395                 400

Ser Arg Asn Tyr Pro Lys Asp Asp Trp Lys Pro Tyr Lys Leu Arg Arg
                405                 410                 415

Leu Tyr Phe Ile Trp Val Cys Arg Asp Ile Gln Ser Phe Arg Trp Phe
                420                 425                 430

Ala Asp Leu Leu Cys Met Leu His Asn Lys Phe Trp Gln Glu Asn Arg
            435                 440                 445

Pro Asp Tyr Val Asn Ile Gln Leu Tyr Leu Ser Gln Thr Asp Gly Ile
450                 455                 460

Gln Lys Ile Ile Gly Glu Lys Tyr His Ala Leu Asn Ser Arg Leu Phe
465                 470                 475                 480

Ile Gly Arg Pro Arg Trp Lys Leu Leu Phe Asp Glu Ile Ala Lys Tyr
                485                 490                 495

Asn Arg Gly Lys Thr Val Gly Val Phe Cys Cys Gly Pro Asn Ser Leu
                500                 505                 510

Ser Lys Thr Leu His Lys Leu Ser Asn Gln Asn Asn Ser Tyr Gly Thr
            515                 520                 525

Arg Phe Glu Tyr Asn Lys Glu Ser Phe Ser
530                 535

<210> SEQ ID NO 3
<211> LENGTH: 2262
<212> TYPE: DNA
<213> ORGANISM: Escherichia coli

<400> SEQUENCE: 3

```
atgtcgcaac ataacgaaaa gaacccacat cagcaccagt caccactaca cgattccagc      60
gaagcgaaac cggggatgga ctcactggca cctgaggacg gctctcatcg tccagcggct     120
gaaccaacac cgccaggtgc acaacctacc gccccaggga gcctgaaagc ccctgatacg     180
cgtaacgaaa aacttaattc tctggaagac gtacgcaaag gcagtgaaaa ttatgcgctg     240
accactaatc agggcgtgcg catcgccgac gatcaaaact cactgcgtgc cggtagccgt     300
ggtccaacgc tgctggaaga tttttattctg cgcgagaaaa tcacccactt tgaccatgag     360
cgcattccgg aacgtattgt tcatgcacgc ggatcagccg ctcacggtta tttccagcca     420
tataaaagct aagcgatat accaaagcg gatttcctct cagatccgaa caaaatcacc     480
ccagtatttg tacgtttctc taccgttcag ggtggtgctg ctctgctga taccgtgcgt     540
gatatccgtg gctttgccac caagttctat accgaagagg tattttttga cctcgttggc     600
aataacacgc caatcttctt tatccaggat gcgcataaat tccccgattt tgttcatgcg     660
gtaaaaccag aaccgcactg gcaattccaa agggcaaa gtgcccacga tactttctgg     720
gattatgttt ctctgcaacc tgaaactctg cacaacgtga tgtgggcgat gtcggatcgc     780
ggcatccccc gcagttaccg caccatggaa ggcttcggta ttcacacctt ccgcctgatt     840
aatgccgaag gaaggcaac gtttgtacgt ttccactgga accactggca aggtaaagcc     900
tcactcgttt gggatgaagc acaaaaactc accggacgtg accgggactt ccaccgccgc     960
gagttgtggg aagccattga agcaggcgat tttccggaat acgaactggg cttccagttg    1020
attcctgaag aagatgaatt caagttcgac ttcgatcttc tcgatccaac caaacttatc    1080
ccggaagaac tggtgcccgt tcagcgtgtc ggcaaaatgg tgctcaatcg caaccccggat    1140
```

-continued

```
aacttctttg ctgaaaacga acaggcggct ttccatcctg gcatatcgt gccgggactg      1200 gacttcacca acgatccgct gttgcaggga cgtttgttct cctataccga tacacaaatc      1260
agtcgtcttg gtgggccgaa tttccatgag attccgatta accgtccgac ctgcccttac      1320
cataatttcc agcgtgacgg catgcatcgc atggggatcg acactaaccc ggcgaattac      1380
gaaccgaact cgattaacga taactggccg cgcgaaacac cgccggggcc gaaacgcggc      1440
ggttttgaat cataccagga gcgcgtggaa ggcaataaag ttcgcgagcg cagcccatcg      1500
tttggcgaat attattccca tccgcgtctg ttctggctaa gtcagacgcc atttgagcag      1560
cgccatattg tcgatggttt cagttttgag ttaagcaaag tcgttcgtcc gtatattcgt      1620
gagcgcgttg ttgaccagct ggcgcatatt gatctcactc tggcccaggc ggtggcgaaa      1680
aatctcggta tcgaactgac tgacgaccag ctgaatatca ccccacctcc ggacgtcaac      1740
ggtctgaaaa aggatccatc cttaagtttg tacgccattc ctgacggtga tgtgaaaggt      1800
cgcgtggtag cgattttact taatgatgaa gtgagatcgg cagaccttct ggccattctc      1860
aaggcgctga aggccaaagg cgttcatgcc aaactgctct actcccgaat gggtgaagtg      1920
actgcggatg acggtacggt gttgcctata gccgctacct tgccggtgc accttcgctg      1980 acggtcgatg cggtcattgt cccttgcggc aatatcgcgg atatcgctga caacggcgat      2040
gccaactact acctgatgga agcctacaaa caccttaaac cgattgcgct ggcgggtgac      2100
gcgcgcaagt ttaaagcaac aatcaagatc gctgaccagg gtgaagaagg gattgtggaa      2160
gctgacagcg ctgacggtag tttatggat gaactgctaa cgctgatggc agcacaccgc      2220
gtgtggtcac gcattcctaa gattgacaaa attcctgcct ga                        2262
```

<210> SEQ ID NO 4
<211> LENGTH: 753
<212> TYPE: PRT
<213> ORGANISM: Escherichia coli

<400> SEQUENCE: 4

```
Met Ser Gln His Asn Glu Lys Asn Pro His Gln His Gln Ser Pro Leu
1               5                   10                  15

His Asp Ser Ser Glu Ala Lys Pro Gly Met Asp Ser Leu Ala Pro Glu
            20                  25                  30

Asp Gly Ser His Arg Pro Ala Ala Glu Pro Thr Pro Pro Gly Ala Gln
        35                  40                  45

Pro Thr Ala Pro Gly Ser Leu Lys Ala Pro Asp Thr Arg Asn Glu Lys
    50                  55                  60

Leu Asn Ser Leu Glu Asp Val Arg Lys Gly Ser Glu Asn Tyr Ala Leu
65                  70                  75                  80

Thr Thr Asn Gln Gly Val Arg Ile Ala Asp Asp Gln Asn Ser Leu Arg
                85                  90                  95

Ala Gly Ser Arg Gly Pro Thr Leu Leu Glu Asp Phe Ile Leu Arg Glu
            100                 105                 110

Lys Ile Thr His Phe Asp His Glu Arg Ile Pro Glu Arg Ile Val His
        115                 120                 125

Ala Arg Gly Ser Ala Ala His Gly Tyr Phe Gln Pro Tyr Lys Ser Leu
    130                 135                 140

Ser Asp Ile Thr Lys Ala Asp Phe Leu Ser Asp Pro Asn Lys Ile Thr
145                 150                 155                 160

Pro Val Phe Val Arg Phe Ser Thr Val Gln Gly Gly Ala Gly Ser Ala
                165                 170                 175
```

```
Asp Thr Val Arg Asp Ile Arg Gly Phe Ala Thr Lys Phe Tyr Thr Glu
            180                 185                 190

Glu Gly Ile Phe Asp Leu Val Gly Asn Asn Thr Pro Ile Phe Phe Ile
        195                 200                 205

Gln Asp Ala His Lys Phe Pro Asp Phe Val His Ala Val Lys Pro Glu
    210                 215                 220

Pro His Trp Ala Ile Pro Gln Gly Gln Ser Ala His Asp Thr Phe Trp
225                 230                 235                 240

Asp Tyr Val Ser Leu Gln Pro Glu Thr Leu His Asn Val Met Trp Ala
            245                 250                 255

Met Ser Asp Arg Gly Ile Pro Arg Ser Tyr Arg Thr Met Glu Gly Phe
        260                 265                 270

Gly Ile His Thr Phe Arg Leu Ile Asn Ala Glu Gly Lys Ala Thr Phe
    275                 280                 285

Val Arg Phe His Trp Lys Pro Leu Ala Gly Lys Ala Ser Leu Val Trp
290                 295                 300

Asp Glu Ala Gln Lys Leu Thr Gly Arg Asp Pro Asp Phe His Arg Arg
305                 310                 315                 320

Glu Leu Trp Glu Ala Ile Glu Ala Gly Asp Phe Pro Glu Tyr Glu Leu
            325                 330                 335

Gly Phe Gln Leu Ile Pro Glu Glu Asp Glu Phe Lys Phe Asp Phe Asp
        340                 345                 350

Leu Leu Asp Pro Thr Lys Leu Ile Pro Glu Glu Leu Val Pro Val Gln
    355                 360                 365

Arg Val Gly Lys Met Val Leu Asn Arg Asn Pro Asp Asn Phe Phe Ala
370                 375                 380

Glu Asn Glu Gln Ala Ala Phe His Pro Gly His Ile Val Pro Gly Leu
385                 390                 395                 400

Asp Phe Thr Asn Asp Pro Leu Leu Gln Gly Arg Leu Phe Ser Tyr Thr
            405                 410                 415

Asp Thr Gln Ile Ser Arg Leu Gly Gly Pro Asn Phe His Glu Ile Pro
        420                 425                 430

Ile Asn Arg Pro Thr Cys Pro Tyr His Asn Phe Gln Arg Asp Gly Met
    435                 440                 445

His Arg Met Gly Ile Asp Thr Asn Pro Ala Asn Tyr Glu Pro Asn Ser
450                 455                 460

Ile Asn Asp Asn Trp Pro Arg Glu Thr Pro Pro Gly Pro Lys Arg Gly
465                 470                 475                 480

Gly Phe Glu Ser Tyr Gln Glu Arg Val Glu Gly Asn Lys Val Arg Glu
            485                 490                 495

Arg Ser Pro Ser Phe Gly Glu Tyr Tyr Ser His Pro Arg Leu Phe Trp
        500                 505                 510

Leu Ser Gln Thr Pro Phe Glu Gln Arg His Ile Val Asp Gly Phe Ser
    515                 520                 525

Phe Glu Leu Ser Lys Val Val Arg Pro Tyr Ile Arg Glu Arg Val Val
530                 535                 540

Asp Gln Leu Ala His Ile Asp Leu Thr Leu Ala Gln Ala Val Ala Lys
545                 550                 555                 560

Asn Leu Gly Ile Glu Leu Thr Asp Asp Gln Leu Asn Ile Thr Pro Pro
            565                 570                 575

Pro Asp Val Asn Gly Leu Lys Lys Asp Pro Ser Leu Ser Leu Tyr Ala
        580                 585                 590

Ile Pro Asp Gly Asp Val Lys Gly Arg Val Val Ala Ile Leu Leu Asn
```

```
              595                 600                 605
Asp Glu Val Arg Ser Ala Asp Leu Leu Ala Ile Leu Lys Ala Leu Lys
    610                 615                 620

Ala Lys Gly Val His Ala Lys Leu Leu Tyr Ser Arg Met Gly Glu Val
625                 630                 635                 640

Thr Ala Asp Asp Gly Thr Val Leu Pro Ile Ala Ala Thr Phe Ala Gly
                645                 650                 655

Ala Pro Ser Leu Thr Val Asp Ala Val Ile Val Pro Cys Gly Asn Ile
            660                 665                 670

Ala Asp Ile Ala Asp Asn Gly Asp Ala Asn Tyr Tyr Leu Met Glu Ala
        675                 680                 685

Tyr Lys His Leu Lys Pro Ile Ala Leu Ala Gly Asp Ala Arg Lys Phe
    690                 695                 700

Lys Ala Thr Ile Lys Ile Ala Asp Gln Gly Glu Gly Ile Val Glu
705                 710                 715                 720

Ala Asp Ser Ala Asp Gly Ser Phe Met Asp Glu Leu Leu Thr Leu Met
                725                 730                 735

Ala Ala His Arg Val Trp Ser Arg Ile Pro Lys Ile Asp Lys Ile Pro
            740                 745                 750

Ala

<210> SEQ ID NO 5
<211> LENGTH: 722
<212> TYPE: DNA
<213> ORGANISM: Zea mays

<400> SEQUENCE: 5
gaagagaact atccagaagc gcaagactcc aaagccgtcg ccttcctatc ctcccttcct      60
cgccgcgggg gtcgcctgag atcacataaa catggtgaag gctgttgctg tgctgggtag     120
cagcgagggt gtcaagggca caatcttctt cacccaagaa ggggatggcc ctaccactgt     180
cactggaagt gtctctggcc tcaagcctgg cctccatggg ttccatgtgc atgcacttgg     240
tgacaccacc aatggctgca tgtcaactgg accacactac aatcctgcga gcaaggaaca     300
tggagcacca gaagatgaga accgccatgc cggtgatctt ggaaatgtga cagctggagc     360
agacggtgtt gcaaacatta tgttaccga cagccagatc ccactgactg gccaaactc      420 aatcattggc agagctgttg ttgttcacgc tgatcccgat gatcttggaa agggtggaca     480
cgagctcagc aagagcaccg gaaacgctgg cggccgtgtt gcttgtggga tcatcggact     540
ccagggctga actgaaacaa atgggtcgct ggacttcggg ggcgcctgag agtgccgtca     600
ccagcaggct agaataacat cccgaagaca tcgtgaaata ataataagag cgcctgatat     660
gtgatcagtg gtgtacttgc cattaagcac ccgatgagct gaactgtgtt ggactgttgg     720
ct                                                                    722

<210> SEQ ID NO 6
<211> LENGTH: 152
<212> TYPE: PRT
<213> ORGANISM: Zea mays

<400> SEQUENCE: 6

Met Val Lys Ala Val Ala Val Leu Gly Ser Ser Glu Gly Val Lys Gly
1               5                   10                  15

Thr Ile Phe Phe Thr Gln Glu Gly Asp Gly Pro Thr Thr Val Thr Gly
            20                  25                  30
```

Ser Val Ser Gly Leu Lys Pro Gly Leu His Gly Phe His Val His Ala
 35                 40                  45

Leu Gly Asp Thr Thr Asn Gly Cys Met Ser Thr Gly Pro His Tyr Asn
 50                  55                  60

Pro Ala Ser Lys Glu His Gly Ala Pro Glu Asp Glu Asn Arg His Ala
 65                  70                  75                  80

Gly Asp Leu Gly Asn Val Thr Ala Gly Ala Asp Gly Val Ala Asn Ile
                 85                  90                  95

Asn Val Thr Asp Ser Gln Ile Pro Leu Thr Gly Pro Asn Ser Ile Ile
             100                 105                 110

Gly Arg Ala Val Val Val His Ala Asp Pro Asp Asp Leu Gly Lys Gly
         115                 120                 125

Gly His Glu Leu Ser Lys Ser Thr Gly Asn Ala Gly Gly Arg Val Ala
     130                 135                 140

Cys Gly Ile Ile Gly Leu Gln Gly
145                 150

<210> SEQ ID NO 7
<211> LENGTH: 3158
<212> TYPE: DNA
<213> ORGANISM: Bos taurus

<400> SEQUENCE: 7
gattttcctc atgggaagaa gaagcatagc agagaagaaa ggcaaactca aggcattgaa      60
cctctgctac catggggaac tgggttgtga atgagggcat ctccatcttt gtcattctgg     120
tatggctggg gatgaacgtc ttccttttg tctggtacta ccgggtttat gatatcccag      180
ataagttctt ttacactcga aaacttcttg ggtcagcgct ggccctggcc agagcccctg     240
cagcctgcct gaatttcaac tgcatgctga ttctgctgcc tgtctgtcga aatctgctct     300
ccttcctcag gggttccagt gcgtgctgct caacaagaat tcggagacaa ctggacagga     360
acctcacctt tcataaaatg gtggcatgga tgattgcact tcacactgca attcatacca     420
ttgcacatct atttaatgtg gagtggtgtg tgaatgcccg agtcaacaat tctgatcctt     480
attcaatagc actctctgac attggagata agcctaatga aacttacctc aattttgttc     540
gacagagaat caagaatcct gaaggaggcc tgtatgtggc tgtgactcgg ttggcaggca     600
tcactggagt cgtcattaca ctgtgcctga tattaattat cacatcctcc accaaaacca     660
tccggaggtc ttattttgaa gtgttttggt acacacacca tctctttgtg atcttcttca     720
ttggtctcgc catccatgga gctcagcgga ttgtacgtgg cagactgca gagagtttgt      780 tgaaacacca accaagaaac tgttatcaaa acatctcaca gtggggaaaa atagagaact     840
gcccaatccc agagttctct gggaaccctc ctatgacttg gaatggata gtgggtccca      900 tgttcctgta tctctgtgag aggttggtac ggttttggag atctcaacag aaggtggtca     960
tcaccaaggt ggtcactcac cctttcaaaa ccatcgagct ccagatgaag aagaaaggat    1020
tcaagatgga ggtgggccaa tacatttcg tcaagtgtcc cgtggtgtcc aagctggagt     1080 ggcaccctt cacccctgacc tctgcccctg aggaagactt ctttagcatc catatccgca    1140 tcgtgggga ctggacagag ggactcttca agcttgtgg ctgtgataag caggagtttc      1200
aagatgcctg gaaactacca aagatagctg ttgacgggcc ctttggcact gccagtgagg    1260
acgtgttcag ttacgaggtg gtgatgttag tgggagcagg gatcggggtt acgcccttg      1320 catccatcct caagtcggtc tggtacaaat attgcaataa agccccaaat ctgaggctca    1380
aaaagatcta cttctactgg ctgtgccggg acacacatgc cttgagtgg tttgcggacc     1440

```
tgctgcagct gctggaaaca cagatgcagg agaagaacaa cacgacttc ctcagctaca    1500 acatctgcct cactggctgg gatgagtctc aggccagtca ctttgctatg catcatgacg    1560
aggagaaaga tgtaatcaca ggcctgaaac aaaagacctt gtatggacga cccaactggg    1620
ataacgagtt caagaccatt ggaagtcaac atcccaatac cagaatagga gtcttcctct    1680
gcggaccgga agccttggct gacacccta ataagcagtg catctccaac tccgactctg    1740
gccccagggg agtgcatttc atttcaaca aggaaaactt ctaactggtc tcttccttga    1800
ggaaataaat gtgggttgta ccactgaata accaagtaat gctagtggat aatataagtt    1860
cctcccttta aaaaaaaag aaaaggaac tatgatgtga tgattttccc tgagaggaat    1920
gtcaaagatt tttaatggtg ataaatttgc atttgtatgg agctttatgg ttttcagagc    1980
aattatataa acttttttt tccttttttt tccccttcac agtaatgcca gagaaaggta    2040
gggcaaagat tctcagactc acttttcagg atgaaaaaa aaaaaaggtt caaaatggtg    2100
aagtaacctc cctaagatga gactggctct aggccatctg actctaggtt tggtgatctt    2160
tcagcaatag caggttgcct ggaaattggt ttgcatgctc ccccaaagaa gaagcaaacc    2220
agggaataat tattcatatt cccttttgtg tcatcttttg tatcattatt gttctattga    2280
aggaaacttt ccaagtagga gataatttat gttgagaatg attcatcact taatagtgat    2340
gacatcctcc agtttaccaa tatagcagcc taactgggtc agagatttct cctaaaaaag    2400
aatattagac tgactggatg tatgtatgac ccaccattta cactggtgct tggcagagag    2460
tggatactca ttgaaagtta gctgaatgaa tgagtgaaaa gacatttaga accatacagt    2520
gccaaggtag aatcaacgga aagccttaaa cagtattatc tgaggaaatc acttctgata    2580
ctctagttga ccaaacgagc ctcattctct taagggtaca gaacaggcta aggttagtaa    2640
ccaatgggtt gtcctgtcca aacactctta tttgaagcat tgcaccaaag ggagatggag    2700
gcagagaaat gaactcctct cataactctg gctggctcct ttagtcctgc tcctgatgct    2760
atgaaagaaa tgcaaactaa tttattgccc aaaacggtcc tctccagcca gcacttgtga    2820
atttgaaatt aagaattgtg acaagtatgt atctgacagc tgctttaaat agcatccacc    2880
ctttatttta cttaaataca catggaaaat tgatcttact agtgtaacta atgatttatc    2940
cttctatcgt catgatcata ataaaattta catcccagaa actaaatccc tagctccaat    3000
agaatattct ggatattcat gagttcaaga atctctaaat cactgttaat gtaactgccc    3060
ctacttctgg gaatgaaaaa cagctttatt tgttatattc tctgcagcca cagatattta    3120
gaagtaatca actttaataa tgaaaaaaaa aaaaaaa                             3158
```

<210> SEQ ID NO 8
<211> LENGTH: 570
<212> TYPE: PRT
<213> ORGANISM: Bos taurus

<400> SEQUENCE: 8

```
Met Gly Asn Trp Val Val Asn Glu Gly Ile Ser Ile Phe Val Ile Leu
1               5                   10                  15

Val Trp Leu Gly Met Asn Val Phe Leu Phe Val Trp Tyr Tyr Arg Val
            20                  25                  30

Tyr Asp Ile Pro Asp Lys Phe Phe Tyr Thr Arg Lys Leu Leu Gly Ser
        35                  40                  45

Ala Leu Ala Leu Ala Arg Ala Pro Ala Ala Cys Leu Asn Phe Asn Cys
    50                  55                  60
```

-continued

```
Met Leu Ile Leu Leu Pro Val Cys Arg Asn Leu Ser Phe Leu Arg
 65                  70                  75                  80

Gly Ser Ser Ala Cys Cys Ser Thr Arg Ile Arg Arg Gln Leu Asp Arg
                 85                  90                  95

Asn Leu Thr Phe His Lys Met Val Ala Trp Met Ile Ala Leu His Thr
            100                 105                 110

Ala Ile His Thr Ile Ala His Leu Phe Asn Val Glu Trp Cys Val Asn
        115                 120                 125

Ala Arg Val Asn Asn Ser Asp Pro Tyr Ser Ile Ala Leu Ser Asp Ile
    130                 135                 140

Gly Asp Lys Pro Asn Glu Thr Tyr Leu Asn Phe Val Arg Gln Arg Ile
145                 150                 155                 160

Lys Asn Pro Glu Gly Gly Leu Tyr Val Ala Val Thr Arg Leu Ala Gly
                165                 170                 175

Ile Thr Gly Val Val Ile Thr Leu Cys Leu Ile Leu Ile Ile Thr Ser
            180                 185                 190

Ser Thr Lys Thr Ile Arg Arg Ser Tyr Phe Glu Val Phe Trp Tyr Thr
        195                 200                 205

His His Leu Phe Val Ile Phe Phe Ile Gly Leu Ala Ile His Gly Ala
    210                 215                 220

Gln Arg Ile Val Arg Gly Gln Thr Ala Glu Ser Leu Leu Lys His Gln
225                 230                 235                 240

Pro Arg Asn Cys Tyr Gln Asn Ile Ser Gln Trp Gly Lys Ile Glu Asn
                245                 250                 255

Cys Pro Ile Pro Glu Phe Ser Gly Asn Pro Pro Met Thr Trp Lys Trp
            260                 265                 270

Ile Val Gly Pro Met Phe Leu Tyr Leu Cys Glu Arg Leu Val Arg Phe
        275                 280                 285

Trp Arg Ser Gln Gln Lys Val Val Ile Thr Lys Val Val Thr His Pro
    290                 295                 300

Phe Lys Thr Ile Glu Leu Gln Met Lys Lys Gly Phe Lys Met Glu
305                 310                 315                 320

Val Gly Gln Tyr Ile Phe Val Lys Cys Pro Val Val Ser Lys Leu Glu
                325                 330                 335

Trp His Pro Phe Thr Leu Thr Ser Ala Pro Glu Glu Asp Phe Phe Ser
            340                 345                 350

Ile His Ile Arg Ile Val Gly Asp Trp Thr Glu Gly Leu Phe Lys Ala
        355                 360                 365

Cys Gly Cys Asp Lys Gln Glu Phe Gln Asp Ala Trp Lys Leu Pro Lys
    370                 375                 380

Ile Ala Val Asp Gly Pro Phe Gly Thr Ala Ser Glu Asp Val Phe Ser
385                 390                 395                 400

Tyr Glu Val Val Met Leu Val Gly Ala Gly Ile Gly Val Thr Pro Phe
                405                 410                 415

Ala Ser Ile Leu Lys Ser Val Trp Tyr Lys Tyr Cys Asn Lys Ala Pro
            420                 425                 430

Asn Leu Arg Leu Lys Lys Ile Tyr Phe Tyr Trp Leu Cys Arg Asp Thr
        435                 440                 445

His Ala Phe Glu Trp Phe Ala Asp Leu Leu Gln Leu Leu Glu Thr Gln
    450                 455                 460

Met Gln Glu Lys Asn Asn Thr Asp Phe Leu Ser Tyr Asn Ile Cys Leu
465                 470                 475                 480

Thr Gly Trp Asp Glu Ser Gln Ala Ser His Phe Ala Met His His Asp
```

```
              485                 490                 495
Glu Glu Lys Asp Val Ile Thr Gly Leu Lys Gln Lys Thr Leu Tyr Gly
            500                 505                 510

Arg Pro Asn Trp Asp Asn Glu Phe Lys Thr Ile Gly Ser Gln His Pro
            515                 520                 525

Asn Thr Arg Ile Gly Val Phe Leu Cys Gly Pro Glu Ala Leu Ala Asp
            530                 535                 540

Thr Leu Asn Lys Gln Cys Ile Ser Asn Ser Asp Ser Gly Pro Arg Gly
545                 550                 555                 560

Val His Phe Ile Phe Asn Lys Glu Asn Phe
                565                 570

<210> SEQ ID NO 9
<211> LENGTH: 707
<212> TYPE: DNA
<213> ORGANISM: Bos taurus

<400> SEQUENCE: 9
gcagtgtccc agccgggttc gtgtcgccat ggggcagatc gagtgggcca tgtgggccaa       60
cgagcaggcg ctggcgtccg gtctaatcct tatcaccggg gcatcgtgg ccacggccgg       120 tcagttcacc cagtggtacc tgggcgccta ctccatagca gcaggcgtat tggtctgcct      180
gctggaatac cctcgaggga agaggagcaa gggctccacc atggagaggt gtggacagaa      240
gtacctgacc agagtggtga agctgttcgg gcccctcacc aggaactact acatccgggc      300
cttcttgcac ctcgggctgg cggtacctgc tggcttcctg ctcgccacca tcctggggac      360
agcctgcttg gccatcgcaa gcggcatcta tctgctggca gccatccgtg gggagcagtg      420
gagccccatt gagcccaagc ccaaggagcg ccgcagatt ggggggcacca tcaagcagcc      480 gcccagcaac cctccacccc ggcccccggc tgaggcccgc aagaagccga gtgaggaggc      540
ggcgggggtc cccacggggtg gcccccagga aaacccatg ccagtgaatg acgaggtcgt      600
gtgaccagaa cctcaagccg ctctggcccg ctgaagcttt gaaggtcctt cctcctgtgg      660
gcaggctagt gggtgggtgg gggtgtgtgg cgcccagcct ggggtgt                   707

<210> SEQ ID NO 10
<211> LENGTH: 191
<212> TYPE: PRT
<213> ORGANISM: Bos taurus

<400> SEQUENCE: 10

Met Gly Gln Ile Glu Trp Ala Met Trp Ala Asn Glu Gln Ala Leu Ala
1               5                   10                  15

Ser Gly Leu Ile Leu Ile Thr Gly Gly Ile Val Ala Thr Ala Gly Gln
                20                  25                  30

Phe Thr Gln Trp Tyr Leu Gly Ala Tyr Ser Ile Ala Ala Gly Val Leu
            35                  40                  45

Val Cys Leu Leu Glu Tyr Pro Arg Gly Lys Arg Ser Lys Gly Ser Thr
        50                  55                  60

Met Glu Arg Cys Gly Gln Lys Tyr Leu Thr Arg Val Val Lys Leu Phe
65                  70                  75                  80

Gly Pro Leu Thr Arg Asn Tyr Tyr Ile Arg Ala Phe Leu His Leu Gly
                85                  90                  95

Leu Ala Val Pro Ala Gly Phe Leu Leu Ala Thr Ile Leu Gly Thr Ala
            100                 105                 110

Cys Leu Ala Ile Ala Ser Gly Ile Tyr Leu Leu Ala Ala Ile Arg Gly
```

|     |     |     |     | 115 |     |     |     | 120 |     |     |     | 125 |     |     |
| --- | --- | --- | --- | --- | --- | --- | --- | --- | --- | --- | --- | --- | --- | --- |
| Glu | Gln | Trp | Ser | Pro | Ile | Glu | Pro | Lys | Pro | Lys | Glu | Arg | Pro | Gln | Ile |
|     | 130 |     |     |     |     | 135 |     |     |     |     | 140 |     |     |     |     |
| Gly | Gly | Thr | Ile | Lys | Gln | Pro | Pro | Ser | Asn | Pro | Pro | Arg | Pro | Pro |
| 145 |     |     |     |     | 150 |     |     |     |     | 155 |     |     |     |     | 160 |
| Ala | Glu | Ala | Arg | Lys | Lys | Pro | Ser | Glu | Glu | Ala | Ala | Gly | Val | Pro | Thr |
|     |     |     |     | 165 |     |     |     |     | 170 |     |     |     |     | 175 |     |
| Gly | Gly | Pro | Gln | Glu | Asn | Pro | Met | Pro | Val | Asn | Asp | Glu | Val | Val |
|     |     |     | 180 |     |     |     |     | 185 |     |     |     |     | 190 |     |

<210> SEQ ID NO 11
<211> LENGTH: 274
<212> TYPE: DNA
<213> ORGANISM: Chlamydomonas sp.

<400> SEQUENCE: 11

| gagctgtcgc | atagatcgcc | tttgcgctcg | caactccccg | ttgcttttga | gccctcgccg | 60 |
| cccctctgcgc | cctcctcgct | gtaacgcaag | actcgacatt | gctaattggc | atcggcttct | 120 |
| ctcgctctct | ggcgacgact | gctgcggcgc | tggccttatc | attcgggcat | gtcactgacg | 180 |
| cccctcgcat | cggcccgcgc | ccgcgctgct | cgcccgcccg | cctcctcccc | cctgcccctc | 240 |
| ctttctcaac | cttccagaac | cttcttcacc | aaag |     |     | 274 |

<210> SEQ ID NO 12
<211> LENGTH: 1503
<212> TYPE: DNA
<213> ORGANISM: Streptomyces rimosus

<400> SEQUENCE: 12

| ggcttgacat | gattggtgcg | tatgtttgta | tgaagctaca | ggactgattt | ggcgggctat | 60 |
| gagggcgcgg | gaagctctgg | aagggccgcg | atggggcgcg | cggcgtccag | aaggcgccat | 120 |
| acggcccgct | ggcggcaccc | atccggtata | aaagcccgcg | accccgaacg | gtgacctcca | 180 |
| ctttcagcga | caaacgagca | cttatacata | cgcgactatt | ctgccgctat | acataaccac | 240 |
| tcagctagct | taagatccca | tcaagcttgc | atgccgggcg | cgccagaagg | agcgcagcca | 300 |
| aaccaggatg | atgtttgatg | gggtatttga | gcacttgcaa | cccttatccg | gaagcccct | 360 |
| ggcccacaaa | ggctaggcgc | caatgcaagc | agttcgcatg | cagcccctgg | agcggtgccc | 420 |
| tcctgataaa | ccggccaggg | ggcctatgtt | ctttactttt | ttacaagaga | agtcactcaa | 480 |
| catcttaaaa | tggccaggtg | agtcgacgag | caagcccggc | ggatcaggca | gcgtgcttgc | 540 |
| agatttgact | tgcaacgccc | gcattgtgtc | gacgaaggct | tttggctcct | ctgtcgctgt | 600 |
| ctcaagcagc | atctaaccct | gcgtcgccgt | ttccatttgc | aggatggcca | ctccgccctc | 660 |
| cccggtgctg | aagaatttcg | aagcatggac | gatgcgttgc | gtgcactgcg | gggtcggtat | 720 |
| cccggttgtg | agtgggttgt | tgtggaggat | ggggcctcgg | gggctggtgt | ttatcggctt | 780 |
| cggggtggtg | ggcgggagtt | gtttgtcaag | gtggcagctc | tgggggccgg | ggtgggcttg | 840 |
| ttgggtgagg | ctgagcggct | ggtgtggttg | gcggaggtgg | ggattcccgt | acctcgtgtt | 900 |
| gtggagggtg | gtggggacga | gagggtcgcc | tggttggtca | ccgaagcggt | tccggggcgt | 960 |
| ccggccagtg | cgcggtggcc | gcgggagcag | cggctggacg | tggcggtggc | gctcgcgggg | 1020 |
| ctcgctcgtt | cgctgcacgc | gctgactgg | gagcggtgtc | cgttcgatcg | cagtctcgcg | 1080 |
| gtgacggtgc | cgcaggcggc | ccgtgctgtc | gctgaaggga | gcgtcgactt | ggaggatctg | 1140 |
| gacgaggagc | ggaagggtg | gtcggggag | cggcttctcg | ccgagctgga | gcggactcgg | 1200 |

```
cctgcggacg aggatctggc ggttttgccac ggtcacctgt gcccggacaa cgtgctgctc    1260
gaccctcgta cctgcgaggt gaccgggctg atcgacgtgg ggcgggtcgg ccgtgcggac    1320
cggcactccg atctcgcgct ggtgctgcgc gagctggccc acgaggagga cccgtggttc    1380
gggccggagt gttccgcggc gttcctgcgg gagtacgggc gcgggtggga tggggcggta    1440
tcggaggaaa agctggcgtt ttaccggctg ttggacgagt tcttctgagg gacctgatgg    1500
tgt                                                                  1503
```

<210> SEQ ID NO 13
<211> LENGTH: 819
<212> TYPE: DNA
<213> ORGANISM: Streptomyces rimosus

<400> SEQUENCE: 13

```
atggacgatg cgttgcgtgc actgcggggt cggtatcccg gttgtgagtg ggttgttgtg     60
gaggatgggg cctcgggggc tggtgtttat cggcttcggg gtggtgggcg ggagttgttt    120
gtcaaggtgg cagctctggg ggccggggtg ggcttgttgg gtgaggctga gcggctggtg    180
tggttggcgg aggtggggat tcccgtacct cgtgttgtgg agggtggtgg ggacgagagg    240
gtcgcctggt tggtcaccga agcggttccg gggcgtccgg ccagtgcgcg gtggccgcgg    300
gagcagcggc tggacgtggc ggtggcgctc gcggggctcg ctcgttcgct gcacgcgctg    360
gactgggagc ggtgtccgtt cgatcgcagt ctcgcggtga cggtgccgca ggcggcccgt    420
gctgtcgctg aagggagcgt cgacttggag gatctggacg aggagcggaa ggggtggtcg    480
ggggagcggc ttctcgccga gctggagcgg actcggcctg cggacgagga tctggcggtt    540
tgccacggtg acctgtgccc ggacaacgtg ctgctcgacc ctcgtacctg cgaggtgacc    600
gggctgatcg acgtggggcg ggtcggccgt gcggaccggc actccgatct cgcgctggtg    660
ctgcgcgagc tggcccacga ggaggacccc tggttcgggc cggagtgttc cgcggcgttc    720
ctgcgggagt acgggcgcgg gtgggatggg gcggtatcgg aggaaaagct ggcgttttac    780
cggctgttgg acgagttctt ctgagggacc tgatggtgt                           819
```

<210> SEQ ID NO 14
<211> LENGTH: 820
<212> TYPE: DNA
<213> ORGANISM: Chlamydomonas sp.

<400> SEQUENCE: 14

```
ggatcccaca cacctgcccg tctgcctgac aggaagtgaa cgcatgtcga gggaggcctc     60
accaatcgtc acacgagccc tcgtcagaaa cacgtctccg ccacgctctc cctctcacgg    120
ccgaccccgc agccctttg ccctttccta ggccaccgac aggacccagg cgctctcagc    180
atgcctcaac aacccgtact cgtgccagcg gtgcccttgt gctggtgatc gcttggaagc    240
gcatgcgaag acgaagggc ggagcaggcg gcctggctgt cgaagggct cgccgccagt    300 tcgggtgcct ttctccacgc gcgcctccac acctaccgat gcgtgaaggc aggcaaatgc    360
tcatgtttgc ccgaactcgg agtccttaaa aagccgcttc ttgtcgtcgt tccgagacat    420
gttagcagat cgcagtgcca cctttcctga cgcgctcggc cccatattcg acgcaattg     480 tcatttgtag cacaattgga gcaaatctgg cgaggcagta ggcttttaag ttgcaaggcg    540
agagagcaaa gtgggacgcg gcgtgattat tggtatttac gcgacggccc ggcgcgttag    600
cggcccttcc cccaggccag ggacgattat gtatcaatat tgttgcgttc gggcactcgt    660
```

<210> SEQ ID NO 15
<211> LENGTH: 5298
<212> TYPE: DNA
<213> ORGANISM: Artificial sequence
<220> FEATURE:
<223> OTHER INFORMATION: Synthetic sequence

<400> SEQUENCE: 15

```
gcgagggctc ctgcgggctg ggaggggga tctgggaatt ggaggtacga ccgagatggc      720
ttgctcgggg ggaggtttcc tcgccgagca agccagggtt aggtgttgcg ctcttgactc      780
gttgtgcatt ctaggacccc actgctactc acaacaagcc                            820
ctgacgcgcc ctgtagcggc gcattaagcg cggcgggtgt ggtggttacg cgcagcgtga       60
ccgctacact tgccagcgcc ctagcgcccg ctcctttcgc tttcttccct tcctttctcg      120
ccacgttcgc cggcttgaca tgattggtgc gtatgtttgt atgaagctac aggactgatt      180
tggcgggcta tgagggcgcg ggaagctctg aagggccgc gatggggcgc gcggcgtcca       240
gaaggcgcca tacggcccgc tggcggcacc catccggtat aaaagcccgc gaccccgaac      300
ggtgacctcc actttcagcg acaaacgagc acttatacat acgcgactat ctgccgcta       360
tacataacca ctcagctagc ttaagatccc atcaagcttg catgccgggc gcgccagaag      420
gagcgcagcc aaaccaggat gatgtttgat ggggtatttg agcacttgca accttatcc       480
ggaagccccc tggcccacaa aggctaggcg ccaatgcaag cagttcgcat gcagccctg       540
gagcggtgcc ctcctgataa accggccagg gggcctatgt tctttacttt tttacaagag      600
aagtcactca acatcttaaa atggccaggt gagtcgacga gcaagcccgg cggatcaggc      660
agcgtgcttg cagatttgac ttgcaacgcc cgcattgtgt cgacgaaggc ttttggctcc      720
tctgtcgctg tctcaagcag catctaaccc tgcgtcgccg tttccatttg caggatggcc      780
actccgccct ccccggtgct gaagaattc gaagcatgga cgatgcgttg cgtgcactgc      840
ggggtcggta tcccggttgt gagtgggttg ttgtggagga tggggcctcg ggggctggtg      900
tttatcggct tcggggtggt gggcgggagt tgtttgtcaa ggtggcagct ctggggccg       960
gggtgggctt gttgggtgag gctgagcggc tggtgtggtt ggcggaggtg gggattcccg     1020
tacctcgtgt tgtggagggt ggtggggacg agagggtcgc ctggttggtc accgaagcgg     1080
ttccggggcg tccggccagt gcgcggtggc cgcgggagca gcggctggac gtggcggtgg     1140
cgctcgcggg gctcgctcgt tcgctgcacg cgctggactg ggagcggtgt ccgttcgatc     1200
gcagtctcgc ggtgacggtg ccgcaggcgg cccgtgctgt cgctgaaggg agcgtcgact     1260
tggaggatct ggacgaggag cggaaggggt ggtcggggga gcggcttctc gccgagctgg     1320
agcggactcg gcctgcggac gaggatctgg cggtttgcca cggtcacctg tgcccggaca     1380
acgtgctgct cgaccctcgt acctgcgagg tgaccgggct gatcgacgtg gggcgggtcg     1440
gccgtgcgga ccggcactcc gatctcgcgc tggtgctgcg cgagctggcc cacgaggagg     1500
acccgtggtt cgggccggag tgttccgcgg cgttcctgcg ggagtacggg cgcggtgggg     1560
atggggcggt atcggaggaa aagctggcgt tttaccggct gttggacgag ttcttctgag     1620
ggacctgatg tgttggtgg ctgggtaggg ttgcgtcgcg tgggtgacag cacagtgtgg     1680
acgttgggat ccccgctccg tgtaaatgga ggcgctcgtt gatctgagcc ttgccccctg     1740
acgaacggcg gtggatggaa gatactgctc tcaagtgctg aagcggtagc ttagctcccc     1800
gtttcgtgct gatcagtctt tttcaacacg taaaaagcgg aggagttttg caattttgtt     1860
ggttgtaacg atcctccgtt gattttggcc tcttctccca tgggcgggct gggcgtattt     1920
```

```
gaagcgggta cccagctttt gttcccttta gtgagggtta attgcgcgct tggcgtaatc    1980
atggtcatag ctgtttcctg tgtgaaattg ttatccgctc acaattccac acaacatacg    2040
agccggaagt ctagacggcg gggagctcgc tgaggcttga catgattggt gcgtatgttt    2100
gtatgaagct acaggactga tttggcgggc tatgagggcg cgggaagctc tggaagggcc    2160
gcgatggggc gcgcggcgtc cagaaggcgc catacggccc gctggcggca cccatccggt    2220
ataaaagccc gcgaccccga acggtgacct ccactttcag cgacaaacga gcacttatac    2280
atacgcgact attctgccgc tatacataac cactcagcta gcttaagatc ccatcaagct    2340
tgcatgccgg gcgcgccaga aggagcgcag ccaaaccagg atgatgtttg atggggtatt    2400
tgagcacttg caacccttat ccggaagccc cctggcccac aaaggctagg cgccaatgca    2460
agcagttcgc atgcagcccc tggagcggtg ccctcctgat aaaccggcca gggggcctat    2520
gttctttact tttttacaag agaagtcact caacatctta aaatggccag gtgagtcgac    2580
gagcaagccc ggcggatcag gcagcgtgct tgcagatttg acttgcaacg cccgcattgt    2640
gtcgacgaag gcttttggct cctctgtcgc tgtctcaagc agcatctaac cctgcgtcgc    2700
cgtttccatt tgcaggatgg ccactccgcc ctccccggtg ctgaagaatt cgaaattaa    2760
ccctcactaa agggaacaaa agctgggtac cgggccccccc ctcgaggtcg acggtatcga    2820
taagcttgat atcgaattcc tgcagcccgg gggatcccg ctccgtgtaa atggaggcgc    2880
tcgttgatct gagccttgcc ccctgacgaa cggcggtgga tggaagatac tgctctcaag    2940
tgctgaagcg gtagcttagc tccccgtttc gtgctgatca gtcttttca acacgtaaaa    3000
agcggaggag ttttgcaatt ttgttggttg taacgatcct ccgttgattt tggcctcttt    3060
ctccatgggc gggctgggcg tatttgaagc gggtacccag cttttgttcc ctttagtgag    3120
ggttaattgc gcgcttggcg taatcatggt catagctgtt tcctgtgtga aattgttatc    3180
cgctcacaat tccacacaac atacgagccg aagcataaa gtgtaaagcc tggggtgcct    3240
aatgagtgag ctaactcaca ttaattgcgt tgcgctcact gcccgctttc cagtcgggaa    3300
acctgtcgtg ccagctgcat taatgaatcg gccaacgcgc ggggagaggc ggtttgcgta    3360
ttgggcgctc ttccgcttcc tcgctcactg actcgctgcg ctcggtcgtt cggctgcggc    3420
gagcggtatc agctcactca aaggcggtaa tacggttatc cacagaatca ggggataacg    3480
caggaaagaa catgtgagca aaaggccagc aaaaggccag gaaccgtaaa aaggccgcgt    3540
tgctggcgtt ttccatagg ctccgccccc ctgacgagca tcacaaaaat cgacgctcaa    3600
gtcagaggtg gcgaaacccg acaggactat aaagatacca ggcgtttccc cctggaagct    3660
ccctcgtgcg ctctcctgtt ccgaccctgc cgcttaccgg atacctgtcc gcctttctcc    3720
cttcgggaag cgtggcgctt tctcatagct cacgctgtag gtatctcagt tcggtgtagg    3780
tcgttcgctc caagctgggc tgtgtgcacg aaccccccgt tcagcccgac cgctgcgcct    3840
tatccggtaa ctatcgtctt gagtccaacc cggtaagaca cgacttatcg ccactggcag    3900
cagccactgg taacaggatt agcagagcga ggtatgtagg cggtgctaca gagttcttga    3960
agtggtggcc taactacggc tacactagaa ggacagtatt tggtatctgc gctctgctga    4020
agccagttac cttcggaaaa agagttggta gctcttgatc cggcaaacaa accaccgctg    4080
gtagcggtgg tttttttgtt tgcaagcagc agattacgcg cagaaaaaaa ggatctcaag    4140
aagatccttt gatcttttct acggggtctg acgctcagtg gaacgaaaac tcacgttaag    4200
ggattttggt catgagatta tcaaaaagga tcttcaccta gatcctttta aattaaaaat    4260
```

| | |
|---|---|
| gaagtttta atcaatctaa agtatatatg agtaaacttg gtctgacagt taccaatgct | 4320 |
| taatcagtga ggcacctatc tcagcgatct gtctatttcg ttcatccata gttgcctgac | 4380 |
| tccccgtcgt gtagataact acgatacggg agggcttacc atctggcccc agtgctgcaa | 4440 |
| tgataccgcg agacccacgc tcaccggctc cagatttatc agcaataaac cagccagccg | 4500 |
| gaagggccga gcgcagaagt ggtcctgcaa ctttatccgc ctccatccag tctattaatt | 4560 |
| gttgccggga agctagagta agtagttcgc cagttaatag tttgcgcaac gttgttgcca | 4620 |
| ttgctacagg catcgtggtg tcacgctcgt cgtttggtat ggcttcattc agctccggtt | 4680 |
| cccaacgatc aaggcgagtt acatgatccc ccatgttgtg caaaaaagcg gttagctcct | 4740 |
| tcggtcctcc gatcgttgtc agaagtaagt tggccgcagt gttatcactc atggttatgg | 4800 |
| cagcactgca taattctctt actgtcatgc catccgtaag atgcttttct gtgactggtg | 4860 |
| agtactcaac caagtcattc tgagaatagt gtatgcggcg accgagttgc tcttgcccgg | 4920 |
| cgtcaatacg ggataatacc gcgccacata gcagaacttt aaaagtgctc atcattggaa | 4980 |
| aacgttcttc ggggcgaaaa ctctcaagga tcttaccgct gttgagatcc agttcgatgt | 5040 |
| aacccactcg tgcacccaac tgatcttcag catcttttac tttcaccagc gtttctgggt | 5100 |
| gagcaaaaac aggaaggcaa aatgccgcaa aaaagggaat aagggcgaca cggaaatgtt | 5160 |
| gaatactcat actcttcctt tttcaatatt attgaagcat ttatcagggt tattgtctca | 5220 |
| tgagcggata catatttgaa tgtatttaga aaaataaaca aatagggggtt ccgcgcacat | 5280 |
| ttccccgaaa agtgccac | 5298 |

<210> SEQ ID NO 16
<211> LENGTH: 3430
<212> TYPE: DNA
<213> ORGANISM: Arabidopsis thaliana

<400> SEQUENCE: 16

| | |
|---|---|
| cagttgtgtt cttttctttt tttctttgca tatttgcatt tagaatgttt aataattaag | 60 |
| ttactgtatt tccacataca ttagttccaa gaatatacat atattaattt attttttctta | 120 |
| aaaatgtttt ggaatgacta atattgacaa cgaaaataga agctatgcta aaccattacg | 180 |
| tatatgtgac ttcacatgtt gttgttttac attccctata tatatggatg gctgtcacaa | 240 |
| tcagaaacgt gatcgaaaaa agacaaacag tgtttgcata aaaagactat ttcgtttcat | 300 |
| tgacaatttg tgtttatttg taaagaaaag tggcaaagtg gaatttgagt tcctgcaagt | 360 |
| aagaaagatg aaataaaaga cttgagtgtg tgttttttttc ttttatctga aagctgcaat | 420 |
| gaaatattcc taccaagccc gtttgattat taattggggt ttggttttct tgatgcgaac | 480 |
| taattggtta tataagaaac tatacaatcc atgttaattc aaaaattttg atttctcttg | 540 |
| taggaatatg atttactata tgagactttc ttttcgccaa taatagtaaa tccaaagata | 600 |
| tttgaccgga ccaaaacaca ttgatctatt ttttagttta tttaatccag tttctctgag | 660 |
| ataattcatt aaggaaaact tagtattaac ccatcctaag attaaatagg agccaaactc | 720 |
| acatttcaaa tattaaataa cataaaatgg atttaaaaaa tctatacgtc aaattttatt | 780 |
| tatgacattt cttatttaaa tttatattta atgaaataca gctaagacaa accaaaaaaa | 840 |
| aaatactttc taagtggtcc aaaacatcaa ttccgttcaa tattattagg tagaatcgta | 900 |
| cgaccaaaaa aggtaggtta atacgaaatt acaaacatat ctatatacat agtatatatt | 960 |
| attacctatt atgaggaatc aaaatgcatc aaatatggat ttaaggaatc cataaaagaa | 1020 |
| taaattctac ggaaaaaaaa aaagaataaa attctttaa gttttttaat tgttttttat | 1080 |

```
ttggtagttc tccatttgt tttatttcgt ttggatttat tgtgtccaaa tactttgtaa    1140
accaccgttg taattcttaa acggggtttt cacttctttt ttatattcag acataaagca    1200
tcggctggtt taatcaatca atagatttta tttttcttct caattattag taggtttgat    1260
gtgaacttta caaaaaaaac aaaaacaaat caatgcagag aaaagaaacc acgtgggcta    1320
gtcccacctt gtttcatttc caccacaggt tcgatcttcg ttaccgtctc caataggaaa    1380
ataaacgtga ccacaaaaaa aaaacaaaaa aaaagtctat atattgcttc tctcaagtct    1440
ctgagtgtca tgaaccaaag taaaaaacaa agactcgagt tgatatgtct agtactaaag    1500
atatgtcaac tgtccaaaac gcaactcctt ttaacggcgt tgccccatcc accaccgtgc    1560
gagttacaat cgtccaatcc tccaccgtct ataacgatac tcctgccact ataggtaacc    1620
aatccattaa ttcatcctct gacctatttt tatttttatt ttttgatatg taaaatttat    1680
cgaaaacgtt ccatttcaat atgtagacaa agcggagaag tatattgtgg aggcggcaag    1740
caagggagca gagctagtgt tgttcccgga ggggtttatc ggtggctatc ctcgaggttt    1800
taggttcggt ttagcggttg gcgttcataa cgaagaaggg cgtgatgagt ttcggaagta    1860
ccatgcttct gctattcatg ttcctggtat tactatttac ttccattatt tgtattcttt    1920
ttattatcat cttatcttgt atttatcca taaaatgatt tttgatacat ttttaaccaa    1980
tcaatgactt tgaaccatat cctcaattat tgcatgctta tcctaggccg agtgtattca    2040
aagtatacac caccgatct cggatccaag cctaccaaaa atttggatat gcggatctag    2100
atgacaatat ttatcctgat ctttatcttt taaatgtata aattactata tgttacatta    2160
aattttataa tttttacacc aaaaaatata atattaaatc tctttaatta aagatttttt    2220
ttatttctcc tttatttggt tgctggatta tgatttttag ttggctatgg ttggagtctt    2280
ggtgatgtgt ataagttttg gacaattgaa ttttatttgg aacaaagtaa acttaacttt    2340
gagggaaaat atgtttgatt tcgagttctc ttttttttg tcacgtttag atgaaattta    2400
attgaacaa gcatctaatt aatgagtgtt cttgctctag tttaaattta gttgagcact    2460
ctcaatatct tggaacacaa aatgactctt ttggtttttt gtgatgaatc ttcaggccct    2520
gaagtagcaa gattggctga cgtggctagg aaaaaccatg tgtacttggt aatgggagcc    2580
atagagaagg aagggtatac cctctattgc acagttcttt tctttagtcc acagggtcag    2640
ttcttgggca agcaccgtaa actcatgccc acaagtttgg aacgttgcat ttggggccaa    2700
ggggacggat caaccatccc cgtttacgac actcccattg gaaaactcgg tgctgctatt    2760
tgctgggaga ataggatgcc cctctacaga actgcattgt acgccaaagg tcagcttta    2820
atgcaatgcc gtttgaaaca tctaggcttt tacaaaaaaa tcttacaaag tttttttttt    2880
atttttcgtt tttggtgttt aggcattgag ctttattgtg cacctactgc tgatggttcg    2940
aaagaatggc aatcgtcgat gcttcacatt gcgatcgaag gtggatgttt cgtcttgtcg    3000
gcttgccaat tctgccagcg taaacatttc cctgatcatc ctgactactt gtttaccgat    3060
tggtacgacg acaaagaaca tgattctatt gtctcccaag gtggaagtgt cattatttca    3120
cctttgggac aagttctcgc cggaccaaac tttgaatcag agggtctcgt cacagctgat    3180
attggtatgt atatgtatat ttacactctc atttgatagt catcttaggt tatagaaaag    3240
gataacgttt tttttttttt ttccatcaag atcttggtga tatagcaaga gccaagttat    3300
acttcgattc ggttggacat tactcgagac cagatgtttt acacttgacc gtaaatgagc    3360
acccgaggaa atcggttaca ttcgtgacga aggtggagaa agctgaggat gactcaaaca    3420
```

| aatagtaaga | 3430 |

<210> SEQ ID NO 17
<211> LENGTH: 3522
<212> TYPE: DNA
<213> ORGANISM: Volvox carteri f. nagariensis

<400> SEQUENCE: 17

| atgttaccgg tgggagcggg gctgctggga acaggcaaag catacgaacc ttgcctcctg | 60 |
| gtcttcaggg tctgcggctc caacgccgcg gctttcacgt gcattatgca aaagatatcc | 120 |
| acaaatctgt ctcaacctcg actacgaagc ctatcgctgt tcttggggttg agccctcga | 180 |
| gcgcgccgaa accacaacaa gctgttcccg ctctacgtta acggcgtggc aaagtcatac | 240 |
| tttaaaatca gcgccagccg cgactacgcg caggtgctcc ggcgcctgct gcggcgagac | 300 |
| ccgctgctca catttgccct ccaaaaagcc attaaaaacc tttcaaaagg cgactgtaag | 360 |
| cccgtcagcc acgtcacctc cgaccccacc gggcagtccg cgtcgctcta tggcctccgc | 420 |
| atcaccccct gcgtgtggtc ggacaccaac ggacacaagc tccccgccct cctcctggag | 480 |
| cacaacgtgc cgtacgagtc gcaggatgtc atgccgcgcc tgctccgcga ctacgcagtc | 540 |
| ctgtcccacg tgccttccat tctcacactt atagacttca acggccacgt gttgtaccaa | 600 |
| aacgccgcca gcattgacta ctgcggcgac ctgaccagcc acaacgtgga accggcgac | 660 |
| ggaatgatgg gtgtgttgtt tcagtacgag ccgcagctgc tgcaggagat gctgcaggag | 720 |
| gtgaatgagg gcaactactg gcagcaggtc gtgcgcgtgc cggcctcgct caagcggcac | 780 |
| atggtctttg aggcggaaac gacctggagc tacgggagcc gcggcggcgg cggaaagaag | 840 |
| ctcactgctg ccgtcagcaa gcgcttcatt caggacgcga tggagccgga gttccagctg | 900 |
| gaaagcttca cgacgcaaca tgcccgcagc cagcggaaca cacggcgcg cggactggcg | 960 |
| tccctgtttc agacgcaggt tagcatggcg cggcaggaga gcctggggcc agcgggggcg | 1020 |
| gggggccgtg gcaatggcag cccccggcaa caggcgcctg cgccgcagcg gcaggacacg | 1080 |
| cgggacagcg gcgtcgcaat tgccgggccg gcggcgctgc ccgtgggtcg cctaggtagc | 1140 |
| atcaccgggc ctgccccgcg cctggctagc aataccctca ccccaggcac cagtgcgcac | 1200 |
| gtcgcgttca atctgcccaa tcagctcgaa gattcgtcac cgggtccccc ggcggcaatg | 1260 |
| gcggggtcct tcaccgttac tgccgctaag gctggtggcg gcggaggcgg aggcgccttg | 1320 |
| gtgccgcagc agcactcgca cctgaccaat gccggccaaa tcggcggttt catgacgctg | 1380 |
| atgcaatcgg cggagcggca gcagccaccc agcttcacgg cgtcattgca gagcttcaac | 1440 |
| acagatgggg agaagcccga gtcgcggggg ttgttggcgc aggaagaatg ctggcatgac | 1500 |
| atctcagcaa tcccgcttct ggacccggtc ctggacaagc aggtataccg gggggtggag | 1560 |
| gcatacgggg gggaggcgta tgggggaagg ggcggcaccg cactggggtt gggcttggga | 1620 |
| agcgaggtga tactgctgct ccagaccaac gtcacagccc gggtggagct ggagaaccgg | 1680 |
| ctggcggacc tgacggatgc gcagctgggc atgttggagc agctcttccc ccgccacgtc | 1740 |
| atcgagtata tgctgtccca caaacacggc tacaactccc gcaacctgac ccatctggcc | 1800 |
| aaccaccacg cgacgtcat tgtgctgttt acgatgtgg tgggcttcac gtcgatgagt | 1860 |
| aaggaggtcg agcccagcga ggtgatgcac ttcctgaacg agctgtacac catctttgac | 1920 |
| gacctggtgg atatccacga cctgtacaag ctggacaccg tgggcgactg ctacatcgtg | 1980 |
| gtggcggggc tcaccatgca ggacgacgac ggcttcacgt gcacggtgca aggggacaac | 2040 |
| gatcaacggc tgcaccacgc ggaggtcatg atggactttg caaaggccat cctgcgggag | 2100 |

-continued

```
tccaagcagg tcctcatgcc gcacaataac agccctgtgc aaatacgcat cgggatccac    2160
tttggcagcc tggccagcgg cttggtgggg cccaagatgc ccaagttcac gctgtttggg    2220
gacacgatga acaccgccag caggatggaa agcacctgca agccaggatg cgtccaggtt    2280
tcggaggtgt ttgcgaagct gcttccgttc gaggactggc aggacacggg tggcgtggag    2340
gtcaagggaa aaggacacat gcagaccttt ctgtggatcc ccaaacccga ggacctcatc    2400
ccgagtggta tgggaggtcg atcgccgtgc cgcagcggcg atggcggcgg ctccgtcggc    2460
tctacggacg gcgccatggc gcctgcggcc agcgctgcca gctccgtcac caacggcgcg    2520
ggactcgatg acttggccac ggaccgcacg gacatgaaca gcaccggtcg ggccagtgct    2580
gcatcgctag tgcgcgcccg gtcagcacgt gccgcctccg ttcgacccaa atcgagtcga    2640
cccaaatcga gtcgctactt cacgcggccc tcgacggcac ggcttcggga aagctatgct    2700
ggtggcagtg gcagcggtag cggcggccct ggcagcacga gccgcccgag cacggccagc    2760
agcggtctag gccgcatgtc gtccctcggg cgaaccagcc tcggccggtc taccacactc    2820
aaccggtcga tgtcgcgccg caatgtgagt ttccgcttcc agggagactt accggacgac    2880
gatttgggca tggaggagga ggatgccaac cccttcatgg ccattctcag ccacatccgc    2940
ggcagcaaca cgggcgagcc agaggacggc ggcggcggcg gtggcggcgg cagcggcatg    3000
gcgtccgggc accgagacat taccgccggc ttgcgcatct ctagcgatgg cgagaacgaa    3060
ggcgacaaca agccgcagcg cagcggcccg ccctgggcg ccaagcgagt cagcaacggt     3120
tactcgggag gagggccct gcgtcggagc ggcagcggcg cgatggcggc gcaggtccgg     3180
ttgagctcca gtgggacgcc gcggatgagt aacaatggag gaatgcggat cagcggcccc    3240
ggccaaggcg ccggcgccgg cagcagtcct ggttaccggt ctttagtgga gggcagcgcg    3300
gtgcaggcag tggacgagac ggaagcgata gacgagctga aggcgtgcat ggtggtggcc    3360
aaggcggagg gcgcgctgaa gcccgccagg gccgtacggt tgacgtttgc gccagagatg    3420
cagctgccgc tgtcgccgac gctattaacg caccttccgc agcagcagca gcagcagccg    3480
aatgccacgg cgaccacgac aacgatggtg gcgaacaatt ag                       3522
```

GENETICALLY INDUCIBLE HYDROGEN PEROXIDE RESISTANCE AND PRODUCTION

CROSS REFERENCE TO RELATED APPLICATIONS

This application claims priority to and the benefit under 35 U.S.C. 3.71 of PCT/US2012/058756, filed on Oct. 4, 2012 as well as U.S. Provisional Application No. 61/544,165 filed Oct. 6, 2011, the entire contents of both applications are incorporated herein by reference for all purposes.

ACKNOWLEDGEMENT OF FEDERAL RESEARCH SUPPORT

This invention was made, in part, with government support awarded by United States Department of Agriculture grant number 2006-35318-17445. Accordingly, the United States government has certain rights in this invention.

SUBMISSION OF SEQUENCE LISTING

The Sequence Listing associated with this application is filed in electronic format via EFS-Web and is hereby incorporated by reference into the specification in its entirety.

BACKGROUND

All publications cited in this application are herein incorporated by reference.

$H_2O_2$ is a reactive oxygen species (ROS) commonly used as a general biocide in wastewater treatment and for cleaning of algal bioreactors prior to restarting batch cultures. $H_2O_2$ cannot be used to control microbial pests in large-scale algal cultures because the desired cyanobacteria and eukaryotic algae are naturally very sensitive to $H_2O_2$, especially cyanobacteria. $H_2O_2$ is a small, non-polar molecule soluble in both water and lipids. Applied exogenously, $H_2O_2$ is believed to kill cells by diffusing rapidly through biological membranes and generating highly destructive hydroxyl radicals (OH.) through Fenton chemistry. $H_2O_2$ is also known to directly inhibit thiol-modulated enzymes that participate in photosynthesis and other cellular metabolism. For example, concentrations of $H_2O_2$ as low as 10 μM decreased photosynthetic carbon fixation by 50% in plant chloroplasts. Exogenous $H_2O_2$ also inhibits turnover of the D1 protein at the translation step of protein synthesis. D1 is part of the core of the Photosystem II (PSII) complex and D1 turnover is necessary for repair of the daily photodamage incurred by PSII. $H_2O_2$ is a simple molecule but its effect on cells can be complex. One reason for this is that, in addition to entering freely into cells from exogenous sources, $H_2O_2$ is produced endogenously by aerobic metabolism, for example during beta-oxidation of fatty acids or photorespiration. Moreover, $H_2O_2$ is a signaling molecule known to activate the SoxR and OxyR regulons and to trigger genes for programmed cell death.

Consistent with its inhibition of metabolism and triggering of cell death, various organisms, including humans and bacteria, utilize $H_2O_2$ secretion to defend themselves from pathogens and competitors. A common example is human neutrophils that secrete an "oxidative burst" of lethal $H_2O_2$ to kill invading bacteria that they encounter in blood and tissues.

$H_2O_2$ is a broad-spectrum biocide effective against unwanted microbes of all kinds. It degrades spontaneously to oxygen ($O_2$) and water ($H_2O$), leaving no residual activity. $H_2O_2$ can be applied cheaply at large scales by means of dry compounds that release $H_2O_2$ when dissolved in water. Broad-spectrum algaecides with this mode of action are already in use for control of algal blooms in natural waters, e.g. PAK™27.

The foregoing examples of the related art and limitations related therewith are intended to be illustrative and not exclusive. Other limitations of the related art will become apparent to those of skill in the art upon a reading of the specification.

SUMMARY

It is to be understood that the present invention includes a variety of different versions or embodiments, and this Summary is not meant to be limiting or all-inclusive. This Summary provides some general descriptions of some of the embodiments, but may also include some more specific descriptions of other embodiments.

An embodiment of the present invention may comprise DNA constructs for the expression of proteins in the cell wall, cell membrane, cytosol or organelles of an organism, where the expressed protein is a hydrogen peroxide resistance protein. Such DNA constructs may be represented as Pro-CAT, Pro-CAT-SM, Pro-Ribo-CAT or Pro-Ribo-CAT-SM wherein Pro is an inducible and/or constitutive promoter, CAT is a hydrogen peroxide resistance protein such as a catalase, SM is a selectable marker such as a fluorescent protein sequence and Ribo is an optional transcription element.

An embodiment may further comprise a transgenic unicellular organism having a DNA construct stably integrated into the organism's genome under conditions suitable for an expression of the DNA construct in the cell wall, cell membrane, cytosol or organelles of the organism, wherein the DNA construct expresses a protein in the cell wall, cell membrane, cytosol or organelles of the organism, and wherein the expressed protein is a hydrogen peroxide resistance protein.

An embodiment of the present invention may further comprise a method for producing a transgenic unicellular organism expressing a hydrogen peroxide resistance protein which comprises growing a transgenic unicellular organism having a DNA construct stably integrated into a genome under conditions suitable for an expression of the DNA construct in the transgenic unicellular organism, wherein the DNA construct expresses a protein in the cell wall, cell membrane, cytosol or organelles of the organism, and wherein the expressed protein is a hydrogen peroxide resistance protein.

An embodiment of the present invention may comprise DNA constructs for the expression of proteins in the cell wall, cell membrane, cytosol or organelles of an organism, where the expressed protein is a hydrogen peroxide production protein. Such DNA constructs may be represented as Pro-HPP, Pro1-HPP-Pro2-SM, Pro-Ribo-HPP, Pro1-Ribo-HPP-Pro2-SM, or ProCY-CYBB-CYBA-ProSM-SM wherein Pro1, Pro2 and ProCY are inducible and/or constitutive promoters, HPP is a hydrogen peroxide production protein, CYBB-CYBA is a cytochrome hydrogen peroxide production protein complex, SM is a selectable marker such as a fluorescent protein sequence and Ribo is an optional transcription element.

An embodiment may further comprise a transgenic unicellular organism having a DNA construct stably integrated into the organism's genome under conditions suitable for an expression of the DNA construct in the cell wall, cell membrane, cytosol or organelles of the organism, wherein the DNA construct expresses a protein in the cell wall, cell membrane, cytosol or organelles of the organism, and wherein the expressed protein is a hydrogen peroxide production protein.

An embodiment of the present invention may further comprise a method for producing a transgenic unicellular organism expressing a hydrogen peroxide production protein which comprises growing a transgenic unicellular organism having a DNA construct stably integrated into a genome under conditions suitable for an expression of the DNA construct in the transgenic unicellular organism, wherein the DNA construct expresses a protein in the cell wall, cell membrane, cytosol or organelles of the organism, and wherein the expressed protein is a hydrogen peroxide production protein.

An embodiment of the present invention may comprise one or more DNA constructs for the expression of proteins in the cell wall, cell membrane, cytosol or organelles of an organism, where the expressed proteins are a hydrogen peroxide resistance protein and hydrogen peroxide production protein. Such DNA constructs may be represented as ProCAT-CAT-ProHPP-HPP wherein ProCAT and ProHPP are inducible and/or constitutive promoters, CAT is a hydrogen peroxide resistance protein and HPP is a hydrogen peroxide production protein.

An embodiment may further comprise a transgenic unicellular organism having a DNA construct stably integrated into the organism's genome under conditions suitable for an expression of the DNA construct in the cell wall, cell membrane, cytosol or organelles of the organism, wherein the DNA construct expresses a protein in the cell wall, cell membrane, cytosol or organelles of the organism, and wherein the expressed protein is a hydrogen peroxide resistance protein and a hydrogen peroxide production protein.

An embodiment of the present invention may further comprise a method for producing a transgenic unicellular organism expressing a hydrogen peroxide resistance protein and a hydrogen peroxide production protein which comprises growing a transgenic unicellular organism having a DNA construct stably integrated into a genome under conditions suitable for an expression of the DNA construct in the transgenic unicellular organism, wherein the DNA construct expresses a protein in the cell wall, cell membrane, cytosol or organelles of the organism, and wherein the expressed protein is a hydrogen peroxide resistance protein and a hydrogen peroxide production protein.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

As used herein, "sometime" means at some indefinite or indeterminate point of time. So for example, as used herein, "sometime after" means following, whether immediately following or at some indefinite or indeterminate point of time following the prior act.

Various embodiments of the present invention are set forth in the Detailed Description as provided herein and as embodied by the claims. It should be understood, however, that this Summary does not contain all of the aspects and embodiments of the present invention, is not meant to be limiting or restrictive in any manner, and that the invention(s) as disclosed herein is/are understood by those of ordinary skill in the art to encompass obvious improvements and modifications thereto.

Additional advantages of the present invention will become readily apparent from the following discussion, particularly when taken together with the accompanying drawings and sequence listings.

BRIEF DESCRIPTION OF THE DRAWINGS

To further clarify the above and other advantages and features of the present invention, a more particular description of the invention is rendered by reference to specific embodiments thereof which are illustrated in the appended drawings. It is appreciated that these drawings depict only typical embodiments of the invention and are therefore not to be considered limiting of its scope. The invention is described and explained with additional specificity and detail through the use of the accompanying drawings in which.

Figure 1:
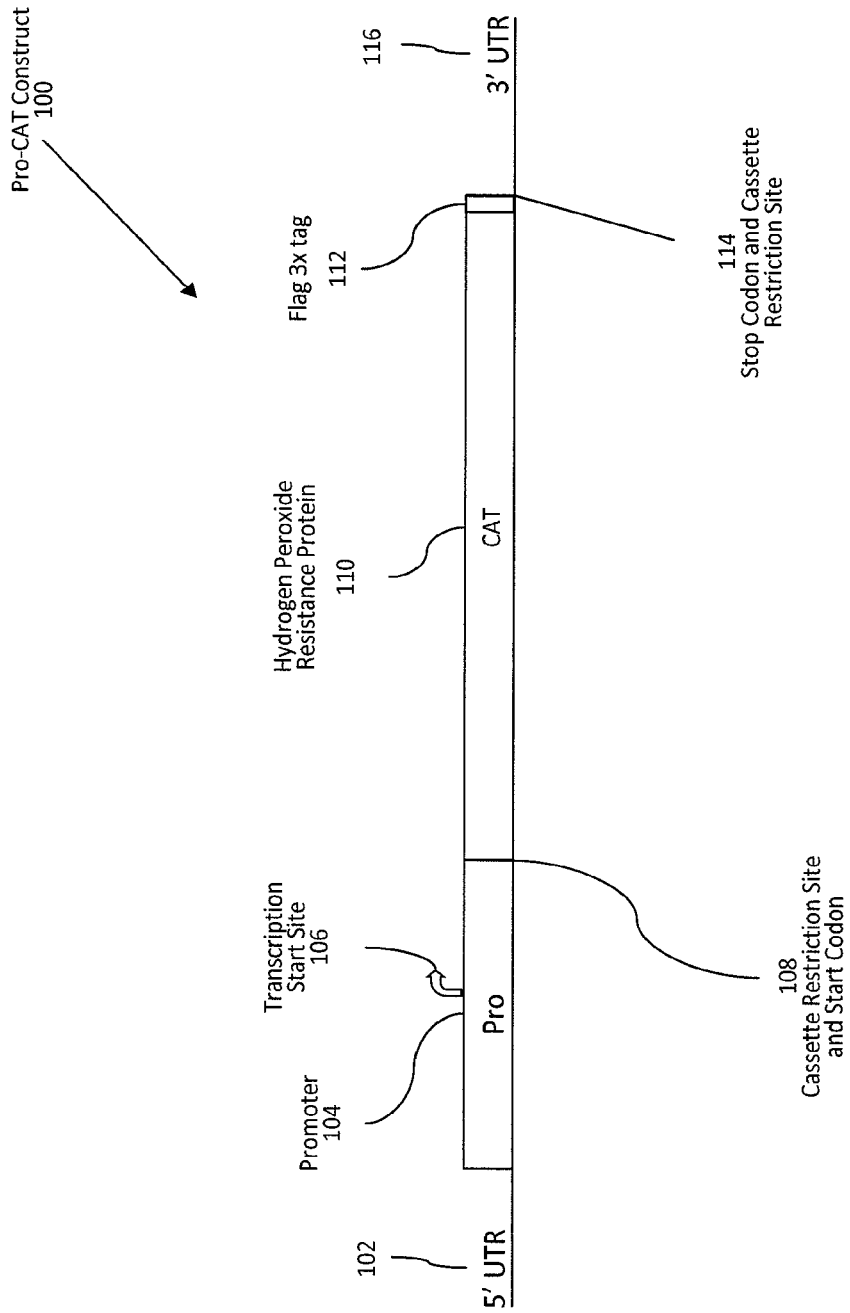
FIG. 1 is a map of a DNA construct, represented as Pro-CAT that includes (from 5' to 3'), promoter and a hydrogen peroxide resistance protein coding sequence.

The drawings are not necessarily to scale.

BRIEF DESCRIPTION OF THE SEQUENCE LISTINGS

SEQ ID NO: 1 discloses the nucleic acid sequence for the *Homo sapiens* NADPH oxidase 4 (NOX4), transcript variant 2, mRNA sequence (GENBANK Accession number NM_001143836).

SEQ ID NO: 2 discloses the protein sequence for the *Homo sapiens* NADPH oxidase 4 (NOX4), transcript variant 2, mRNA sequence (GENBANK Accession number NP_001137308.1).

SEQ ID NO: 3 discloses the nucleic acid sequence of the *Escherichia coli* str. K-12 substr. MG1655 catalase chromosome (GENBANK Accession No.: NC_000913).

SEQ ID NO: 4 discloses the protein sequence of the *Escherichia coli* str. K-12 substr. MG1655 catalase chromosome (GENBANK Accession No.: YP_025308.1).

SEQ ID NO: 5 discloses the nucleic acid sequence of the *Zea mays* superoxide dismutase4 (sod4) (GENBANK Accession No.: 162463248).

SEQ ID NO: 6 discloses the protein sequence of the *Zea mays* superoxide dismutase4 (sod4) (GENBANK Accession No.: NP_001105704).

SEQ ID NO: 7 discloses the nucleic acid sequence of the *Bos taurus* cytochrome b-245, beta polypeptide (CYBB) (GENBANK Accession No.: NM 174035).

SEQ ID NO: 8 discloses the protein sequence of the *Bos taurus* cytochrome b-245, beta polypeptide (CYBB) (GENBANK Accession No.: NP_776460).

SEQ ID NO: 9 discloses the nucleic acid sequence of the *Bos taurus* cytochrome b-245, alpha polypeptide (CYBA) (GENBANK Accession No.: NM_174034).

SEQ ID NO: 10 discloses the protein sequence of the *Bos taurus* cytochrome b-245, alpha polypeptide (CYBA) (GENBANK Accession No.: NP_776459).

SEQ ID NO: 11 discloses the nucleic acid sequence for the THI4 riboswitch alt. spliced exon with 5' NotI and 3' NdeI.

SEQ ID NO: 12 discloses the nucleic acid sequence for the paromomycin resistance marker (aph VIIIsr) w/upstream Hsp70A/RbcS2 promoter and intron 1.

SEQ ID NO: 13 discloses the nucleic acid sequence for the paromomycin resistance marker (GENBANK Accession number AF182845.2).

SEQ ID NO: 14 discloses the nucleic acid sequence for the PSAD promoter.

SEQ ID NO: 15 discloses the nucleic acid sequence for the RbcS2 promoter flanked by enhancer elements of Hsp70A and RbcS2 intron 1 ("Hsp70A/RbcS2").

SEQ ID NO:16 discloses the nucleic acid sequence for the NIT1 promoter (GENBANK Accession Number Y07648.2).

SEQ ID NO:17 discloses the nucleic acid sequence for the CYC6 promoter (GENBANK Accession Number XM_002955348).

DETAILED DESCRIPTION

Embodiments of the present invention include DNA constructs as well as methods for integration of the DNA constructs into photosynthetic unicellular organisms for the expression of hydrogen peroxide (H$_2$O$_2$) resistance as well as proteins for the production of hydrogen peroxide or a combination of both resistance to and production of hydrogen peroxide proteins. Transgenic cells are engineered to highly express cytosolic catalases and for increased H$_2$O$_2$ resistance. Embodiments also include DNA constructs as well as methods of integration of the DNA constructs into photosynthetic organisms for the heterologous and endogenous expression of H$_2$O$_2$ production. Hydrogen peroxide producing enzymes/oxidases are also expressed in the cytosol and peroxide is left to diffuse outside the cell. Oxidases include but are not limited to NADPH oxidases, cytochromes, pyruvate oxidases, and flavoprotein oxidases. A "construct" is an artificially constructed segment of DNA that may be introduced into a target unicellular organism.

As used herein, the term "expression" includes the process by which information from a gene is used in the synthesis of a functional gene product, such as the expression of hydrogen peroxide production and resistance proteins in the cell wall of unicellular organisms as well as the cell membrane cytoplasm or any organelle. These products are often proteins, but in non-protein coding genes such as rRNA genes or tRNA genes, the product is a functional RNA. The process of gene expression is used by all known life, i.e., eukaryotes (including multicellular organisms), prokaryotes (bacteria and archaea), and viruses, to generate the macromolecular machinery for life. Several steps in the gene expression process may be modulated, including the transcription, up-regulation, RNA splicing, translation, and post translational modification of a protein.

As shown in FIG. 1, a construct for expression of a hydrogen peroxide resistance protein is generally represented as Pro-CAT 100, where starting at the 5' UTR 102 an inducible or constitutive transcriptional promoter such as RbcS2 promoter (SEQ ID NO: 15) and the PSAD promoter (SEQ ID NO: 14) is provided as Promoter (Pro) 104 with a transcription start site 106. CAT 110 is a hydrogen peroxide resistance protein such as the *E. coli* catalase (KatE) (SEQ. ID NO: 3) where the protein has a restriction site and start codon 108 on the 5' end of the hydrogen peroxide resistance protein. A stop codon and 3' cassette restriction site 114 provides the transcription termination on the 3'UTR 116. The Pro-CAT construct 100 may include a peptide tag such as the FLAG 3x tag 112 or reporter tag to allow for identification of the protein. Each of these components is operably linked to the next, i.e., the promoter is operably linked to the 5' end of the hydrogen peroxide resistance protein sequence encoding the hydrogen peroxide resistance protein. The DNA construct Pro-CAT 100 is then integrated into a photosynthetic unicellular organism such as *Chlamydomonas reinhardtii* and organisms expressing the hydrogen peroxide resistance protein, including expression in the cell wall, cell membrane, cytosol or organelles of the organism, are then generated including but not limited to cyanobacteria or eukaryotic green algae including but not limited to *Arthrospira* spp., *Spirulina* spp., *Calothrix* spp., *Anabaena flos-aquae*, *Aphanizomenon* spp., *Anadaena* spp., *Gleotrichia* spp., *Oscillatoria* spp., *Nostoc* spp., *Synechococcus elongatus* 7942, *Synechococcus* spp., *Synechosystis* spp. PCC 6803, *Synechosystis* spp., *Spirulina plantensis*, *Chaetoceros* spp., *Chlamydomonas reinhardii*, *Chlamydomonas* spp., *Chlorella vulgaris*, *Chlorella* spp., *Cyclotella* spp., *Didymosphenia* spp., *Dunaliella tertiolecta*, *Dunaliella* spp., *Botryococcus braunii*, *Botryococcus* spp., *Gelidium* spp., *Gracilaria* spp., *Hantscia* spp., *Hematococcus* spp., *Isochrysis* spp., *Laminaria* spp., *Navicula* spp., *Pleurochrysis* spp. and *Sargassum* spp.

As used herein "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

Figure 2:
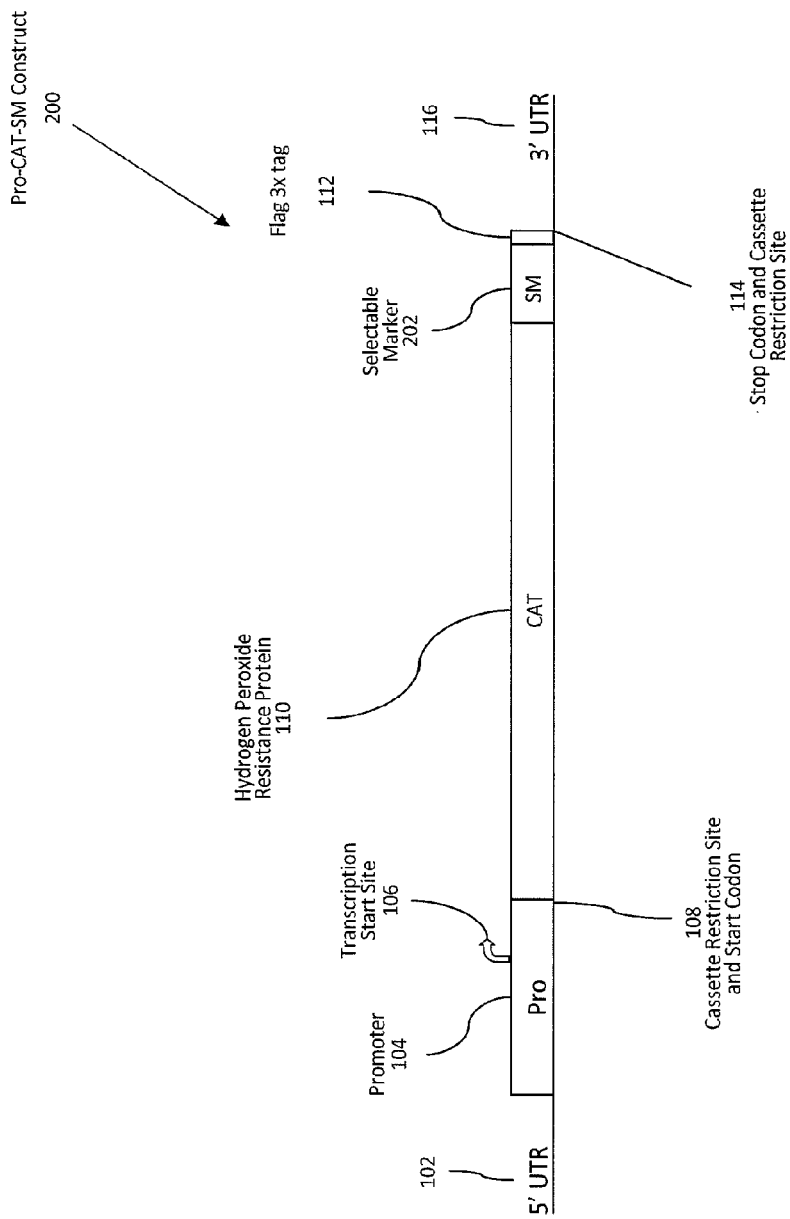
FIG. 2 is a map of a DNA construct, represented as Pro-CAT-SM that includes (from 5' to 3'), promoter; hydrogen peroxide resistance protein coding sequence and a second promoter and selectable marker.

As shown in FIG. 2, a construct for expression of a hydrogen peroxide resistance protein with a selectable marker is generally represented as Pro-CAT-SM 200, where starting at the 5' UTR 102 an inducible transcriptional promoter such as NIT1 inducible promoter (SEQ ID NO: 16) and CYC6 inducible promoters (SEQ ID NO: 17), constitutive promoters such as the RbcS2 promoter (SEQ ID NO: 15) or a promoter with an associated regulatory element promoter such as the PSAD promoter (SEQ ID NO: 14) is provided as Promoter (Pro) 104 with a transcription start site 106. CAT 110 is a hydrogen peroxide resistance protein such as the *E. coli* catalase (CAT) (SEQ. ID NO: 3), where the protein has a restriction site and start codon 108 on the 5' end of the hydrogen peroxide resistance protein. SM, 202 is a selectable marker such as a bleomycin (Ble) resistance marker, a hygromycin resistance marker, the paromomycin resistance marker (aph VIIIsr) (SEQ ID NO:12 or SEQ ID NO:13) or a fluorescent fusion protein yellow fluorescent protein (YFP), a cyan fluorescent protein (CFP), a red fluorescent protein (mRFP). A stop codon and 3' cassette restriction site 114 provides the transcription termination on the 3'UTR 116. The Pro-CAT-SM 200 may include a peptide tag such as the FLAG 3x tag 112 or reporter tag. Each of these components is operably linked to the next, i.e., the promoter coding sequence is operably linked to the 5' end of the hydrogen peroxide resistance protein sequence encoding the hydrogen peroxide resistance protein and the hydrogen peroxide resistance protein sequence is operably linked to the 5' end of the selectable marker coding sequence. The DNA construct Pro-CAT-SM 200 is then integrated into a photosynthetic unicellular organism such as *Chlamydomonas reinhardtii* and organisms expressing the hydrogen peroxide resistance protein, including expression in the outer plasma membrane, inner face of the membrane and cytoplasm of the organism, are then generated including but not limited to cyanobacteria or green algae including but not limited to *Arthrospira* spp., *Spirulina* spp., *Calothrix* spp., *Anabaena flos-aquae*, *Aphanizomenon* spp., *Anadaena* spp., *Gleotrichia* spp., *Oscillatoria* spp., *Nostoc* spp., *Synechococcus elongatus* 7942, *Synechococcus* spp., *Synechosystis* spp. PCC 6803, *Synechosystis* spp., *Spirulina plantensis*, *Chaetoceros* spp., *Chlamydomonas reinhardii*, *Chlamydomonas* spp., *Chlorella vulgaris*, *Chlorella* spp., *Cyclotella* spp., *Didymosphenia* spp., *Dunaliella tertiolecta*, *Dunaliella* spp., *Botryococcus braunii*, *Botryococcus* spp., *Gelidium* spp., *Gracilaria* spp., *Hantscia* spp., *Hematococcus* spp., *Isochrysis* spp., *Laminaria* spp., *Navicula* spp., *Pleurochrysis* spp. *Scenedesmus* spp. and *Sargassum* spp.

Figure 3:
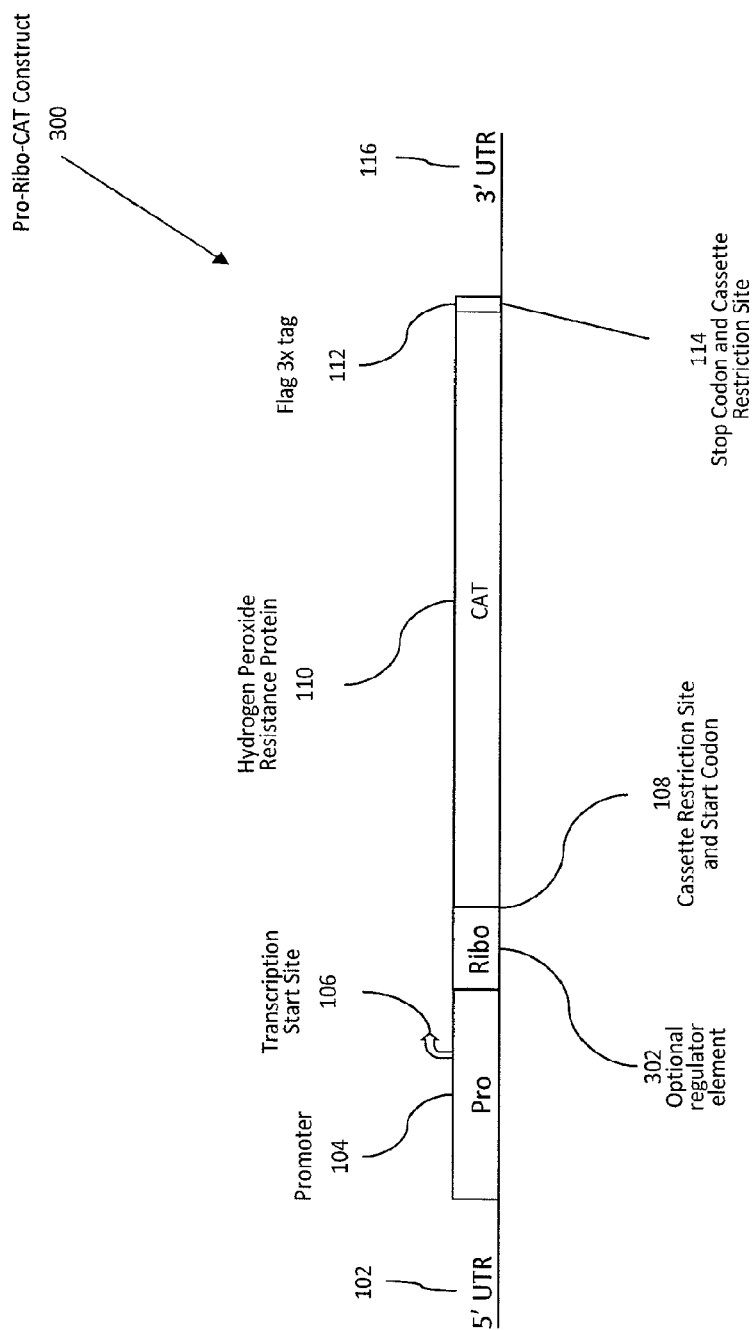
FIG. 3 is a map of a DNA construct, represented as Pro-Ribo-CAT that includes (from 5' to 3'), a promoter, an optional regulator element, and a hydrogen peroxide resistance protein coding sequence.

As shown in FIG. 3, a construct for expression of a hydrogen peroxide resistance protein with a translational regulator is generally represented as Pro-Ribo-CAT 300, where starting at the 5' UTR 102 an inducible transcriptional promoter such as NIT1 inducible promoter (SEQ ID NO: 16) and CYC6 inducible promoters (SEQ ID NO: 17), constitutive promoters such as the RbcS2 promoter (SEQ ID NO: 15) or a promoter with an associated regulatory element promoter such as the PSAD promoter (SEQ ID NO: 14) is provided as Promoter (Pro) 104 with a transcription start site 106. Ribo, 302 is an optional translational regulator such as THI4 riboswitch (SEQ ID NO:11). CAT 110 is a hydrogen peroxide resistance protein such as the *E. coli* catalase (CAT) (SEQ. ID NO: 3) where the protein has a restriction site and start codon 108 on the 5' end of the hydrogen peroxide resistance protein. A stop codon and 3' cassette restriction site 114 provides the transcription termination on the 3'UTR 116. The Pro-Ribo-CAT 300 may include a peptide tag such as the FLAG 3x tag 112 or reporter tag for the identification of the protein. Each of these components is operably linked to the next, i.e., the promoter coding sequence is operably linked to the 5' end of the translational regulator coding sequence and the translational regulator coding sequence is operably linked to the 5' end of the hydrogen peroxide resistance protein sequence encoding the hydrogen peroxide resistance protein. The DNA construct Pro-Ribo-CAT 300 is then integrated into a photosynthetic unicellular photosynthetic organism such as *Chlamydomonas reinhardtii* and organisms expressing the hydrogen peroxide resistance protein, including expression in the outer plasma membrane of the organism, are then generated including but not limited to cyanobacteria including but not limited to *Arthrospira* spp., *Spirulina* spp., *Calothrix* spp., *Anabaena flos-aquae*, *Aphanizomenon* spp., *Anadaena* spp., *Gleotrichia* spp., *Oscillatoria* spp., *Nostoc* spp., *Synechococcus elongatus* 7942, *Synechococcus* spp., *Synechosystis* spp. PCC 6803, *Synechosystis* spp., *Spirulina plantensis*, *Chaetoceros* spp., *Chlamydomonas reinhardii*, *Chlamydomonas* spp., *Chlorella vulgaris*, *Chlorella* spp., *Cyclotella* spp., *Didymosphenia* spp., *Dunaliella tertiolecta*, *Dunaliella* spp., *Botryococcus braunii*, *Botryococcus* spp., *Gelidium* spp., *Gracilaria* spp., *Hantscia* spp., *Hematococcus* spp., *Isochrysis* spp., *Laminaria* spp., *Navicula* spp., *Pleurochrysis* spp. *Scenedesmus* spp. and *Sargassum* spp.

Figure 4:
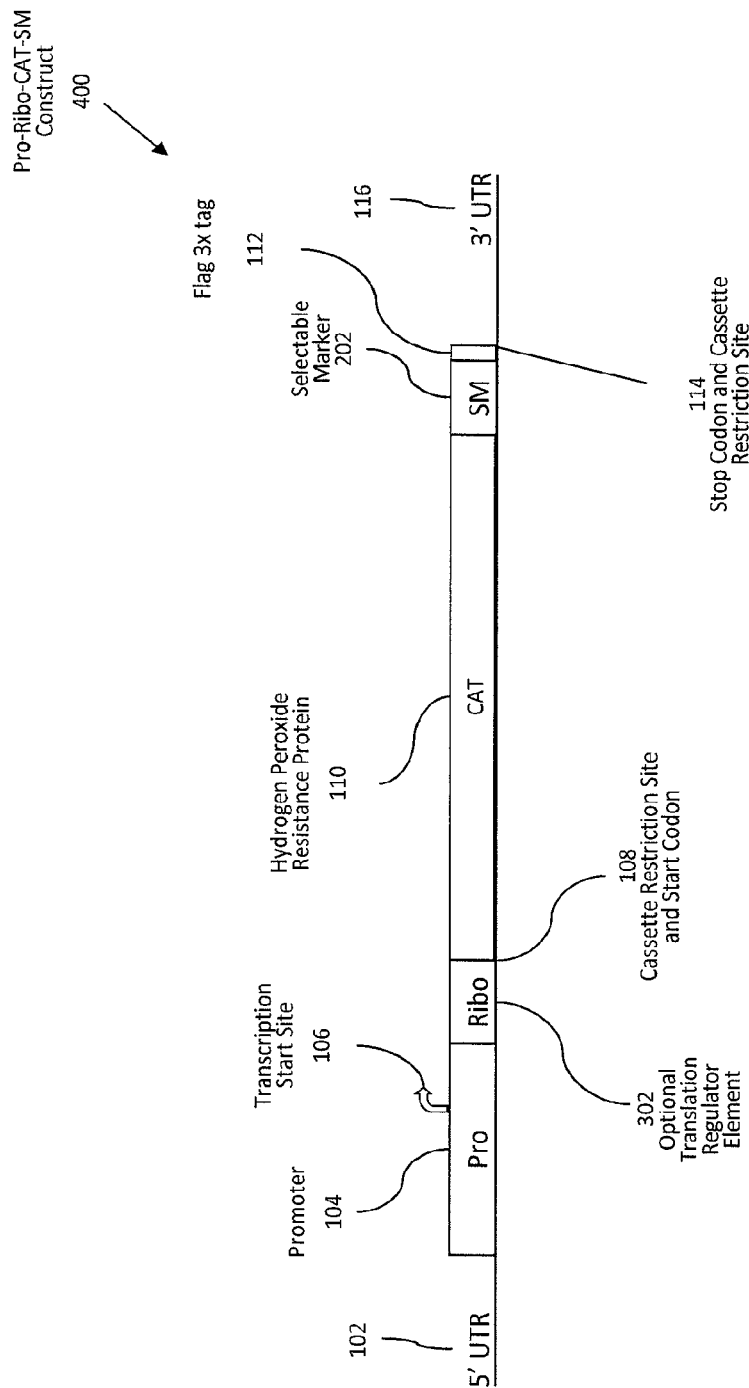
FIG. 4 is a map of a DNA construct, represented as Pro-Ribo-CAT-SM that includes (from 5' to 3'), a promoter, an optional regulator element, a hydrogen peroxide resistance protein coding sequence and a selectable marker coding sequence.

As shown in FIG. 4, a construct for expression of a hydrogen peroxide resistance protein with a translational regulator and a selectable marker is generally represented as Pro-Ribo-CAT-SM 400, where starting at the 5' UTR 102 an inducible transcriptional promoter such as NIT1 inducible promoter (SEQ ID NO: 16) and CYC6 inducible promoters (SEQ ID NO: 17), constitutive promoters such as the RbcS2 promoter (SEQ ID NO: 15) or a promoter with an associated regulatory element promoter such as the PSAD promoter (SEQ ID NO: 14) is provided as Promoter (Pro) 104 with a transcription start site 106. Ribo, 302 is an optional translation regulator such as THI4 riboswitch (SEQ ID NO:11). CAT 110 is a hydrogen peroxide resistance protein such as the *E. coli* catalase (KatE) (SEQ. ID NO: 3) where the protein has a restriction site and start codon 108 on the 5' end of the hydrogen peroxide resistance protein. SM, 202 is a selectable marker such as the paromomycin resistance marker (aph VIIIsr) (SEQ ID NO:12 or SEQ ID NO: 13) or a fluorescent fusion protein yellow fluorescent protein (YFP), a cyan fluorescent protein (CFP), a red fluorescent protein (mRFP). A stop codon and 3' cassette restriction site 114 is provides the transcription termination on the 3'UTR 116. The Pro-Ribo-CAT-SM 400 may include a peptide tag such as the FLAG 3x tag 112 or reporter tag. Each of these components is operably linked to the next, i.e., the promoter coding sequence is operably linked to the 5' end of the translational regulator coding sequence. The translational regulator coding sequence is operably linked to the hydrogen peroxide resistance protein sequence encoding the hydrogen peroxide resistance protein and the hydrogen peroxide resistance protein coding sequence is operably linked to the selectable marker coding sequence. The DNA construct Pro-Ribo-CAT-SM 400 is then integrated into a photosynthetic unicellular organism such as *Chlamydomonas reinhardtii* and organisms expressing the hydrogen peroxide resistance protein, including expression in the outer plasma membrane of the organism, are then generated including but not limited to cyanobacteria including but not limited to *Arthrospira* spp., *Spirulina* spp., *Calothrix* spp., *Anabaena flos-aquae, Aphanizomenon* spp., *Anadaena* spp., *Gleotrichia* spp., *Oscillatoria* spp., *Nostoc* spp., *Synechococcus elongatus* 7942, *Synechococcus* spp., *Synechosystis* spp. PCC 6803, *Synechosystis* spp., *Spirulina plantensis, Chaetoceros* spp., *Chlamydomonas reinhardii, Chlamydomonas* spp., *Chlorella vulgaris, Chlorella* spp., *Cyclotella* spp., *Didymosphenia* spp., *Dunaliella tertiolecta, Dunaliella* spp., *Botryococcus braunii, Botryococcus* spp., *Gelidium* spp., *Gracilaria* spp., *Hantscia* spp., *Hematococcus* spp., *Isochrysis* spp., *Laminaria* spp., *Navicula* spp., *Pleurochrysis* spp. and *Sargassum* spp.

Figure 5:
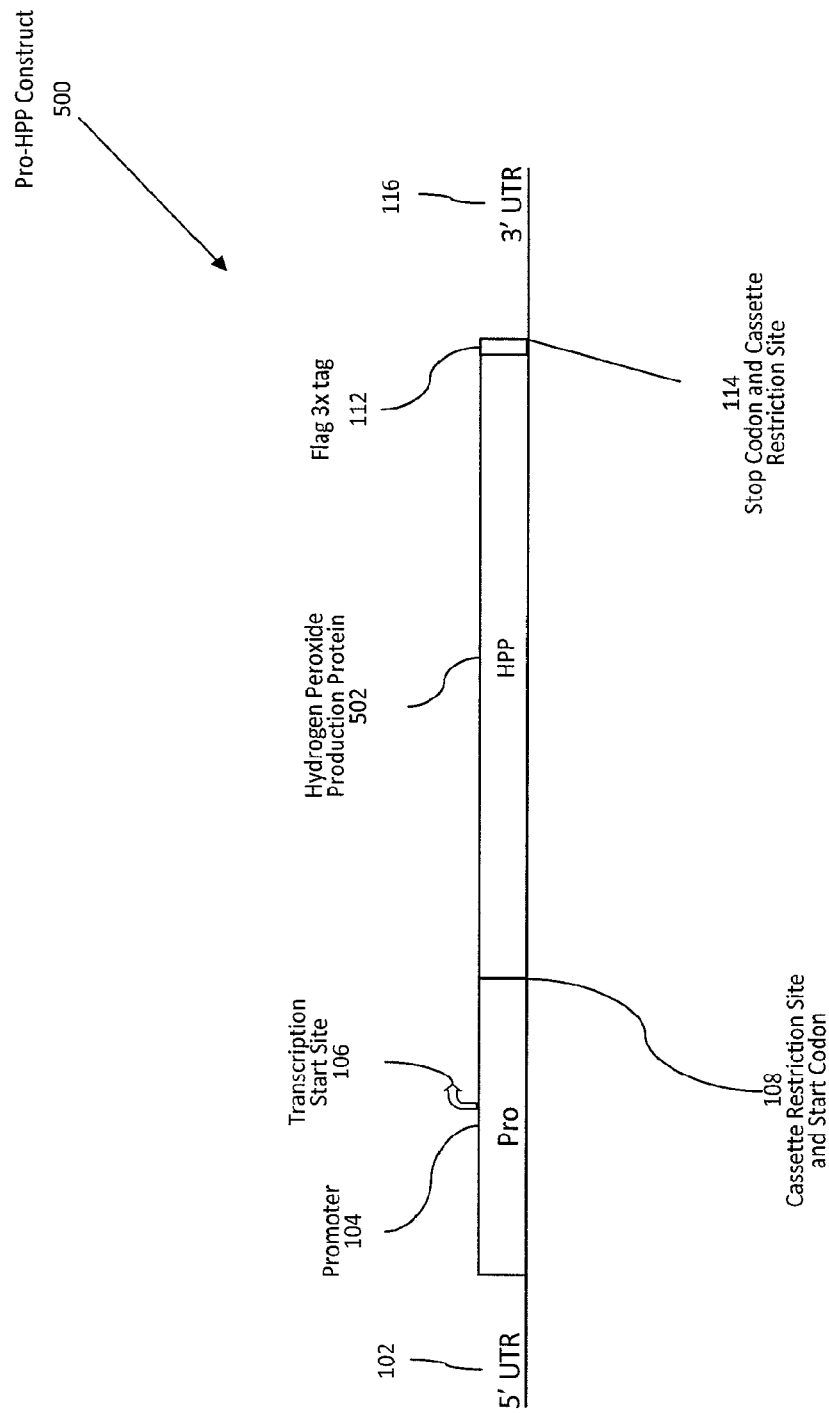
FIG. 5 is a map of a DNA construct, represented as Pro-HPP that includes (from 5' to 3'), a promoter and a hydrogen peroxide production protein coding sequence.

As shown in FIG. 5, a construct for expression of a hydrogen peroxide production protein is generally represented as Pro-HPP 500, where starting at the 5' UTR 102 an inducible transcriptional promoter such as NIT1 inducible promoter (SEQ ID NO: 16) and CYC6 inducible promoters (SEQ ID NO: 17), constitutive promoters such as the RbcS2 promoter (SEQ ID NO: 15) or a promoter with an associated regulatory element promoter such as the PSAD promoter (SEQ ID NO: 14) is provided as Promoter (Pro) 104 with a transcription start site 106. HPP 502 is a hydrogen peroxide production protein such as the *Homo sapiens* NADPH oxidase 4 (NOX4) (SEQ ID NO: 1), the *Zea mays* superoxide dismutase4 (sod4) (SEQ ID NO: 5), or the cytochrome b245 protein complex (SEQ ID NO: 7 and SEQ ID NO:9) where the protein has a restriction site and start codon 108 on the 5' end of the hydrogen peroxide production protein. A stop codon and 3' cassette restriction site 114 is provides the transcription termination on the 3'UTR 116. The Pro-HPP 500 may include a peptide tag such as the FLAG 3x tag 112 or reporter tag. Each of these components is operably linked to the next, i.e., the promoter coding sequence is operably linked to the 5' end of the hydrogen peroxide production protein sequence encoding the hydrogen peroxide production protein. The DNA construct Pro-HPP 500 is then integrated into a photosynthetic unicellular organism such as *Chlamydomonas reinhardtii* and organisms expressing the hydrogen peroxide production protein, including expression in the outer plasma membrane of the organism, are then generated including but not limited to cyanobacteria including but not limited to *Arthrospira* spp., *Spirulina* spp., *Calothrix* spp., *Anabaena flos-aquae, Aphanizomenon* spp., *Anadaena* spp., *Gleotrichia* spp., *Oscillatoria* spp., *Nostoc* spp., *Synechococcus elongatus* 7942, *Synechococcus* spp., *Synechosystis* spp. PCC 6803, *Synechosystis* spp., *Spirulina plantensis, Chaetoceros* spp., *Chlamydomonas reinhardii, Chlamydomonas* spp., *Chlorella vulgaris, Chlorella* spp., *Cyclotella* spp., *Didymosphenia* spp., *Dunaliella tertiolecta, Dunaliella* spp., *Botryococcus braunii, Botryococcus* spp., *Gelidium* spp., *Gracilaria* spp., *Hantscia* spp., *Hematococcus* spp., *Isochrysis* spp., *Laminaria* spp., *Navicula* spp., *Pleurochrysis* spp., *Scenendesumus* spp. and *Sargassum* spp.

Figure 6:
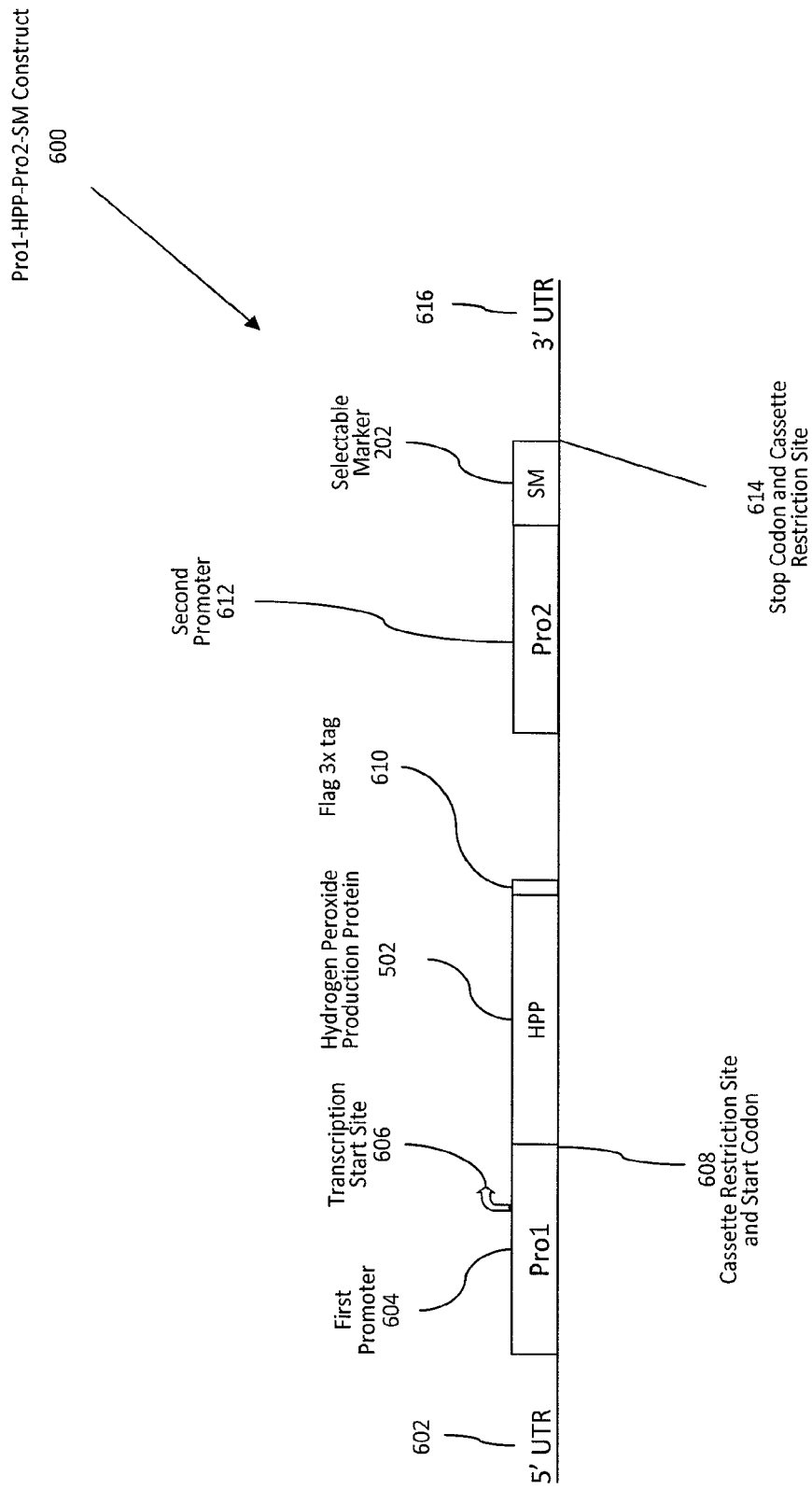
FIG. 6 is a map of a DNA construct, represented as Pro1-HPP-Pro2-SM that includes (from 5' to 3'), a first promoter; a hydrogen peroxide production protein coding sequence a second promoter and a selectable marker.

As shown in FIG. 6, a construct for expression of a hydrogen peroxide production protein with a selectable marker is generally represented as Pro1-HPP-Pro2-SM 600, where starting at the 5' UTR 602 an inducible transcriptional promoter such as NIT1 inducible promoter (SEQ ID NO: 16) and CYC6 inducible promoters (SEQ ID NO: 17), constitutive promoters such as the RbcS2 promoter (SEQ ID NO: 15) or a promoter with an associated regulatory element promoter such as the PSAD promoter (SEQ ID NO: 14) is provided as first promoter (Pro1) 604 with a transcription start site 606. HPP 502 is a hydrogen peroxide production protein such as the *Homo sapiens* NADPH oxidase 4 (NOX4) (SEQ ID NO: 1), the *Zea mays* superoxide dismutase4 (sod4) (SEQ ID NO: 5), or the cytochrome b245 protein complex (SEQ ID NO: 7 and SEQ ID NO:9) where the protein has a restriction site and start codon 608 on the 5' end of the hydrogen peroxide production protein. A peptide tag such as the FLAG 3x tag 610 or reporter tag is used to identify the protein. Second promoter (Pro2) 612 is an inducible transcriptional promoter such as NIT1 inducible promoter (SEQ ID NO: 16) and CYC6 inducible promoters (SEQ ID NO: 17), constitutive promoters such as the RbcS2 promoter (SEQ ID NO: 15) or a promoter with an associated regulatory element promoter such as the PSAD promoter (SEQ ID NO: 14) and SM, 202 is a selectable marker such as a fluorescent fusion protein yellow fluorescent protein (YFP), a cyan fluorescent protein (CFP), a red fluorescent protein (mRFP). A stop codon and 3' cassette restriction site 614 is provides the transcription termination on the 3'UTR 616. Each of these components is operably linked to the next, i.e., the first promoter coding sequence is operably linked to the 5' end of the hydrogen peroxide production protein sequence encoding the hydrogen peroxide production protein and the hydrogen peroxide production protein coding sequence is operably linked to the second promoter which is operably linked to the selectable marker coding sequence. The DNA construct Pro1-HPP-Pro2-SM 600 is then integrated into a photosynthetic unicellular photosynthetic organism such as *Chlamydomonas reinhardtii* and organisms expressing the hydrogen peroxide production protein, including expression in the outer plasma membrane of the organism, are then generated including but not limited to cyanobacteria including but not limited to *Arthrospira* spp., *Spirulina* spp., *Calothrix* spp., *Anabaena flos-aquae, Aphanizomenon* spp., *Anadaena* spp., *Gleotrichia* spp., *Oscillatoria* spp., *Nostoc* spp., *Synechococcus elongatus* 7942, *Synechococcus* spp., *Synechosystis* spp. PCC 6803, *Synechosystis* spp., *Spirulina plantensis, Chaetoceros* spp., *Chlamydomonas reinhardii, Chlamydomonas* spp., *Chlorella vulgaris, Chlorella* spp., *Cyclotella* spp., *Didymosphenia* spp., *Dunaliella tertiolecta, Dunaliella* spp., *Botryococcus braunii, Botryococcus* spp., *Gelidium* spp., *Gracilaria* spp., *Hantscia* spp., *Hematococcus* spp., *Isochrysis* spp., *Laminaria* spp., *Navicula* spp., *Pleurochrysis* spp., *Scenendesumus* spp. and *Sargassum* spp.

Figure 7:
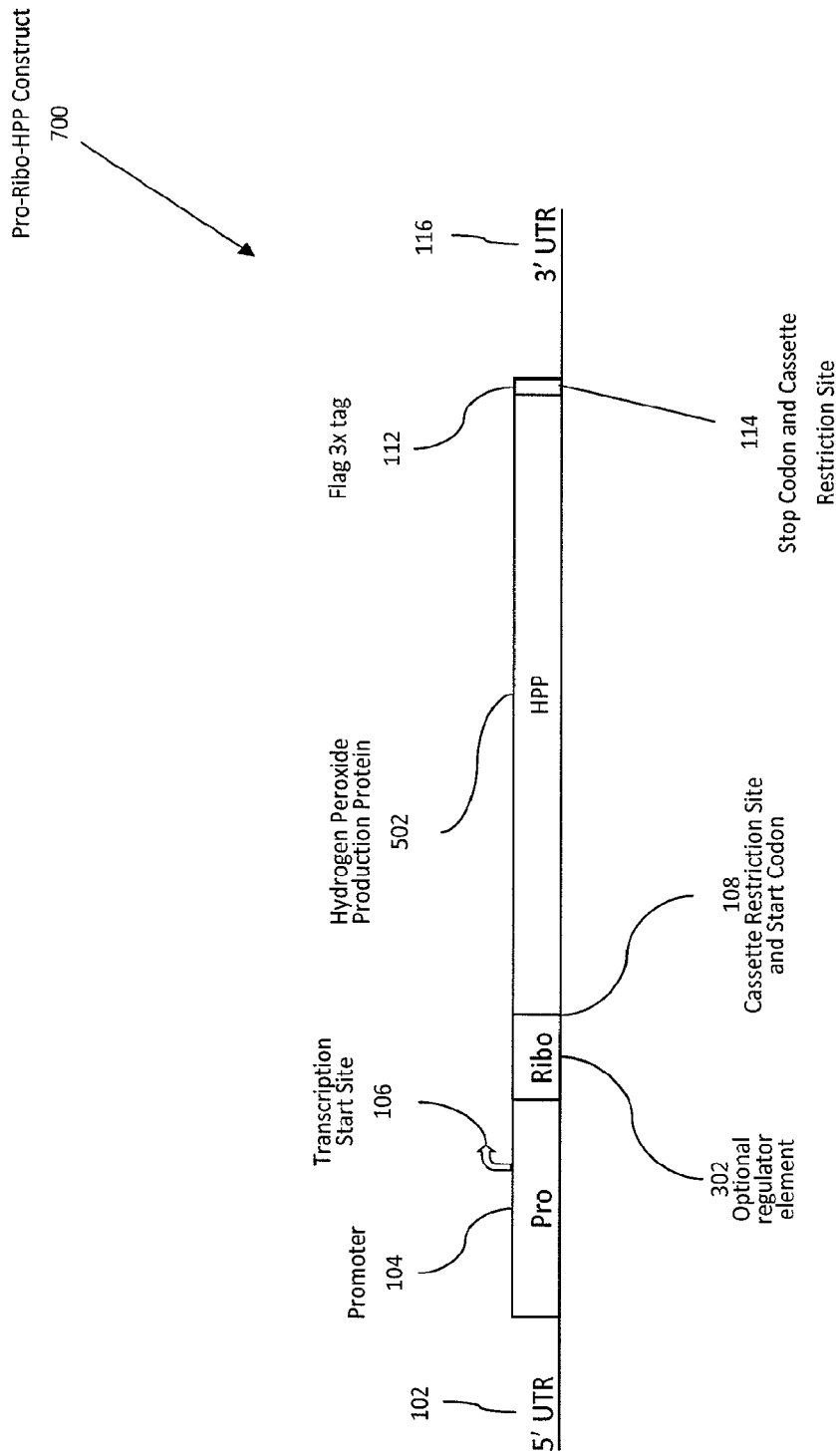
FIG. 7 is a map of a DNA construct, represented as Pro-Ribo-HPP that includes (from 5' to 3'), a promoter, an optional regulator element, and a hydrogen peroxide production and resistance protein coding sequence.

As shown in FIG. 7, a construct for expression of a hydrogen peroxide production protein with a translational regulator is generally represented as Pro-Ribo-HPP 700, where starting at the 5' UTR 102 an inducible transcriptional promoter such as NIT1 inducible promoter (SEQ ID NO: 16) and CYC6 inducible promoters (SEQ ID NO: 17), constitutive promoters such as the RbcS2 promoter (SEQ ID NO: 15) or a promoter with an associated regulatory element promoter such as the PSAD promoter (SEQ ID NO: 14) is provided as Promoter (Pro) 104 with a transcription start site 106. Ribo, 302 is a translational regulator such as THI4 riboswitch (SEQ ID NO:11). HPP 502 is a hydrogen peroxide production protein such as the *Homo sapiens* NADPH oxidase 4 (NOX4) (SEQ ID NO: 1), the *Zea mays* superoxide dismutase4 (sod4) (SEQ ID NO: 5), or the cytochrome b245 protein complex (SEQ ID NO: 7 and SEQ ID NO:9) where the protein has a restriction site and start codon 108 on the 5' end of the hydrogen peroxide production protein. A stop codon and 3' cassette restriction site 114 is provides the transcription termination on the 3'UTR 116. The Pro-Ribo-HPP 700 may include a peptide tag such as the FLAG 3x tag 112 or reporter tag for the identification of the hydrogen peroxide production protein. Each of these components is operably linked to the next, i.e., the promoter coding sequence is operably linked to the 5' end of the translational regulator coding sequence and the translational regulator coding sequence is operably linked to the hydrogen peroxide production protein sequence encoding the hydrogen peroxide production protein. The DNA construct Pro-Ribo-HPP 700 is then integrated into a photosynthetic unicellular organism such as *Chlamydomonas reinhardtii* and organisms expressing the hydrogen peroxide production protein, including expression in the outer plasma membrane of the organism, are then generated including but not limited to cyanobacteria including but not limited to *Arthrospira* spp., *Spirulina* spp., *Calothrix* spp., *Anabaena flos-aquae, Aphanizomenon* spp., *Anadaena* spp., *Gleotrichia* spp., *Oscillatoria* spp., *Nostoc* spp., *Synechococcus elongatus* 7942, *Synechococcus* spp., *Synechosystis* spp. PCC 6803, *Synechosystis* spp., *Spirulina* plantensis, *Chaetoceros* spp., *Chlamydomonas reinhardii, Chlamydomonas* spp., *Chlorella vulgaris, Chlorella* spp., *Cyclotella* spp., *Didymosphenia* spp., *Dunaliella tertiolecta, Dunaliella* spp., *Botryococcus braunii, Botryococcus* spp., *Gelidium* spp., *Gracilaria* spp., *Hantscia* spp., *Hematococcus* spp., *Isochrysis* spp., *Laminaria* spp., *Navicula* spp., *Pleurochrysis* spp., *Scenedesemus* spp. and *Sargassum* spp.

Figure 8:
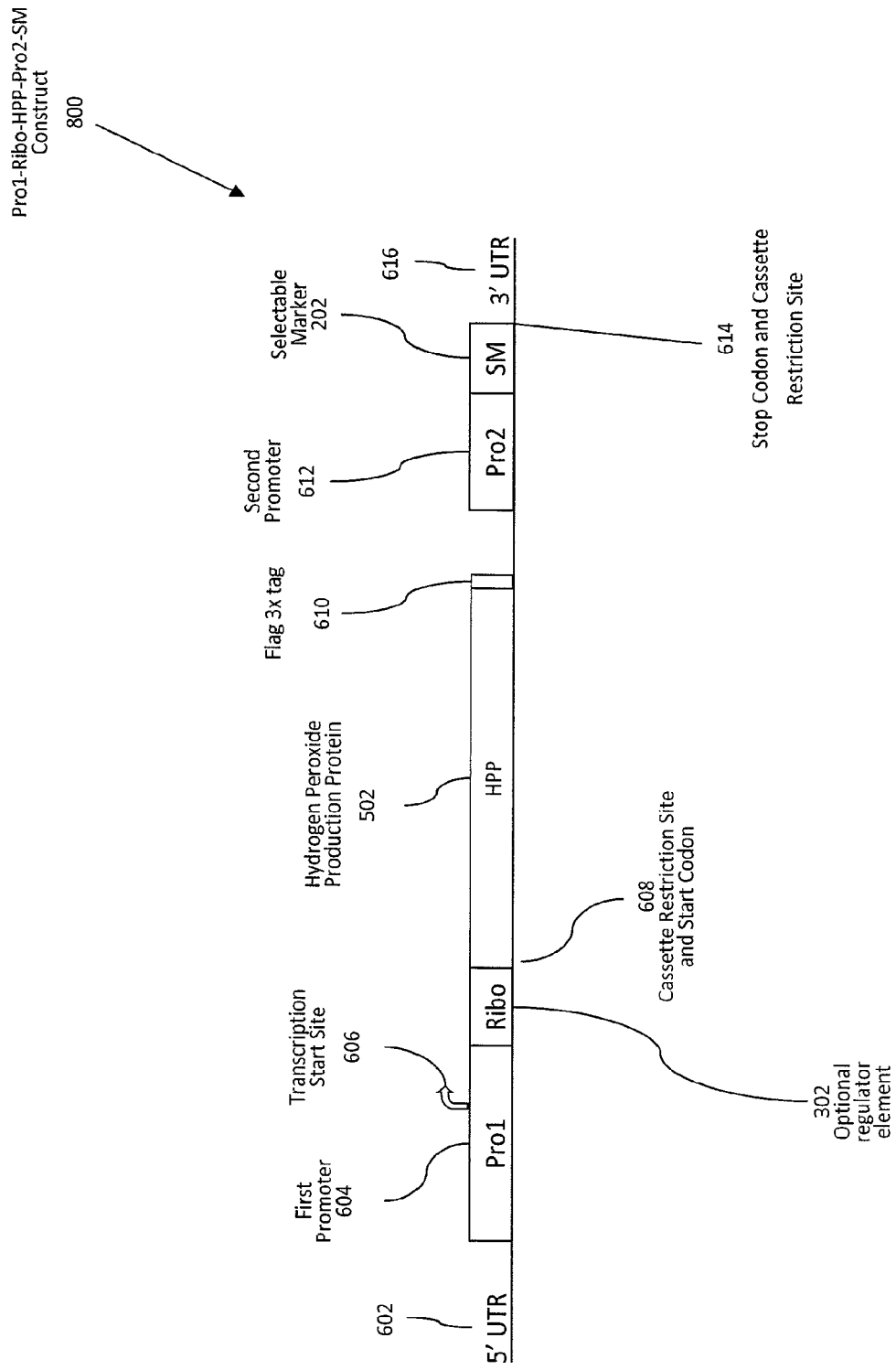
FIG. 8 is a map of a DNA construct, represented as Pro1-Ribo-HPP-Pro2-SM that includes (from 5' to 3'), a first promoter, an optional regulator element, a hydrogen peroxide production protein coding sequence a second promoter and a selectable marker coding sequence.

As shown in FIG. 8, a construct for expression of a hydrogen peroxide production protein with a translational regulator and a selectable marker is generally represented as Pro1-Ribo-HPP-Pro2-SM 800, where starting at the 5' UTR 602 an inducible transcriptional promoter such as the NIT1 inducible promoter (SEQ ID NO: 16) and CYC6 inducible promoters (SEQ ID NO: 17), constitutive promoters such as the RbcS2 promoter (SEQ ID NO: 15) or a promoter with an associated regulatory element promoter such as the PSAD promoter (SEQ ID NO: 14) is provided as First Promoter (Pro1) 604 with a transcription start site 606. Ribo, 302 is a translational regulator such as THI4 riboswitch (SEQ ID NO:11). HPP 502 is a hydrogen peroxide production protein such as the *Homo sapiens* NADPH oxidase 4 (NOX4) (SEQ ID NO: 1), the *Zea mays* superoxide dismutase4 (sod4) (SEQ ID NO: 5), or the cytochrome b245 protein complex (SEQ ID NO: 7 and SEQ ID NO:9) where a Flag 3x tag 610 or reporter tag is attached on the 5' end of the hydrogen peroxide production protein. Second Promoter (Pro2) 610 is an inducible transcriptional promoter such as NIT1 inducible promoter (SEQ ID NO: 16) and CYC6 inducible promoters (SEQ ID NO: 17), constitutive promoters such as the RbcS2 promoter (SEQ ID NO: 15) or a promoter with an associated regulatory element promoter such as the PSAD promoter (SEQ ID NO: 14) and SM, 202 is a selectable marker such as a fluorescent fusion protein yellow fluorescent protein (YFP), a cyan fluorescent protein (CFP), a red fluorescent protein (mRFP). A stop codon and 3' cassette restriction site 614 is provides the transcription termination on the 3'UTR 616. Each of these components is operably linked to the next, i.e., the first promoter coding sequence is operably linked to the 5' end of the translational regulator coding sequence, the translational regulator coding sequence is operably linked to the 5' end of the hydrogen peroxide production protein sequence encoding the hydrogen peroxide production protein and the hydrogen peroxide production protein coding sequence is operably linked to the 5' end of the second promoter coding sequence and the second promoter is operably linked to the 5' end of the selectable marker coding sequence. The DNA construct Pro1-Ribo-HPP-Pro2-SM 800 is then integrated into a photosynthetic unicellular organism such as *Chlamydomonas reinhardtii* and organisms expressing the hydrogen peroxide production protein, including expression in the outer plasma membrane of the organism, are then generated including but not limited to cyanobacteria including but not limited to *Arthrospira* spp., *Spirulina* spp., *Calothrix* spp., *Anabaena flos-aquae, Aphanizomenon* spp., *Anadaena* spp., *Gleotrichia* spp., *Oscillatoria* spp., *Nostoc* spp., *Synechococcus elongatus* 7942, *Synechococcus* spp., *Synechosystis* spp. PCC 6803, *Synechosystis* spp., *Spirulina plantensis, Chaetoceros* spp., *Chlamydomonas reinhardii, Chlamydomonas* spp., *Chlorella vulgaris, Chlorella* spp., *Cyclotella* spp., *Didymosphenia* spp., *Dunaliella tertiolecta, Dunaliella* spp., *Botryococcus braunii, Botryococcus* spp., *Gelidium* spp., *Gracilaria* spp., *Hantscia* spp., *Hematococcus* spp., *Isochrysis* spp., *Laminaria* spp., *Navicula* spp., *Pleurochrysis* spp. and *Sargassum* spp.

Figure 9:
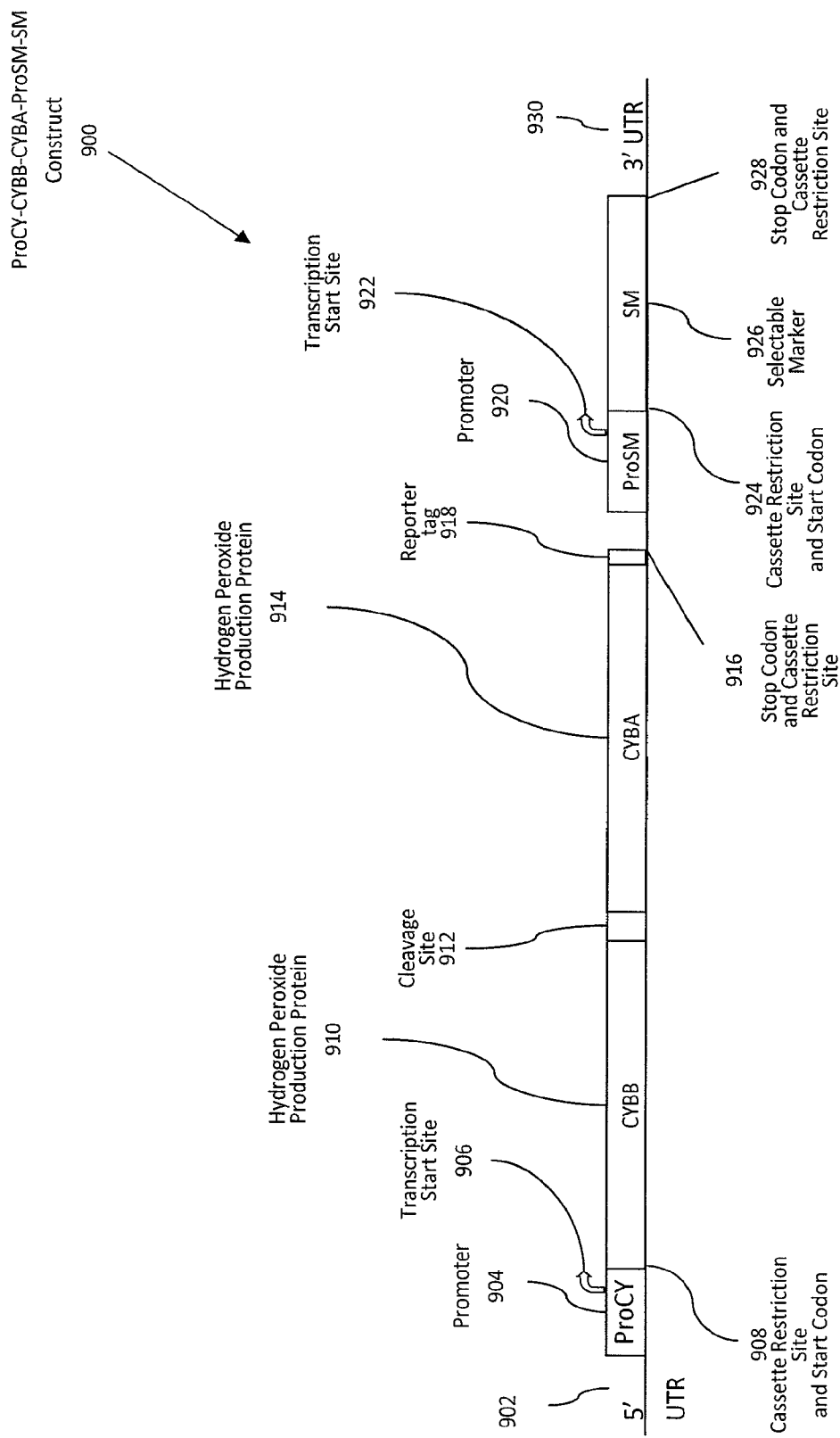
FIG. 9 is a map of a DNA construct, represented as ProCY-CYBB-CYBA-ProSM-SM that includes (from 5' to 3'), a first promoter, the CYBB cytochrome hydrogen peroxide production protein coding sequence, the CYBA cytochrome hydrogen peroxide production protein coding sequence, a second promoter and a selectable marker coding sequence.

As shown in FIG. 9, a construct for expression of a hydrogen peroxide production protein complex with a selectable marker is generally represented as ProCY-CYBB-CYBA-ProSM-SM 900, where starting at the 5' UTR 902 an inducible or constitutive transcriptional promoter such as RbcS2 promoter (SEQ ID NO: 15) the PSAD promoter (SEQ ID NO: 14), the NIT1 promoter (SEQ ID NO:16) or the CYC6 promoter (SEQ ID NO: 17) is provided as ProCY 904 with a transcription start site 906. CYBB 910 is first hydrogen peroxide production protein of the cytochrome b245 protein complex (SEQ ID NO: 7) where the protein has a restriction site and start codon 908 on the 5' end of the hydrogen peroxide production protein 910. A cleavage site 912 operably links the CYBB hydrogen peroxide protein with CYBA 914 which is second hydrogen peroxide production protein of the cytochrome b245 protein complex (SEQ ID NO: 9) where the protein 914 has a restriction site and stop codon 916 on the 3' end of the hydrogen peroxide production protein complex where a reporter tag such as the FLAG 3x tag 918 or reporter tag identifies the location of the protein complex 910 and 914. ProSM 920 is a promoter such as RbcS2 promoter (SEQ ID NO: 15) the PSAD promoter (SEQ ID NO: 14), the NIT1 promoter (SEQ ID NO:16) or the CYC6 promoter (SEQ ID NO: 17) with a transcription start site 922. SM, 926 is a species specific selectable marker such as the paromomycin resistance marker (aph VIIIsr) (SEQ ID NO:12 or SEQ ID NO: 13) where the selectable marker has a restriction site and start codon 924 on the 5' end of the selectable marker. A stop codon and 3' cassette restriction site 928 provides the transcription termination on the 3'UTR 930. Each of these components is operably linked to the next, i.e., the first promoter is operably linked to the 5' end of the CYBB hydrogen peroxide production protein sequence encoding the CYBB hydrogen peroxide production protein and the CYBB hydrogen peroxide production protein coding sequence is operably linked to cleavage site which is operably linked to the 5' end of the CYBA hydrogen peroxide production protein sequence encoding the CYBA hydrogen peroxide protein which is operably linked to a second promoter which is operably linked to a selectable marker. The DNA construct ProCY-CYBB-CYBA-ProSM-SM 900 is then integrated into a photosynthetic unicellular photosynthetic organism such as *Chlamydomonas reinhardtii* and organisms expressing the hydrogen peroxide production protein, including expression in the outer plasma membrane of the organism, are then generated including but not limited to cyanobacteria including but not limited to *Arthrospira* spp., *Spirulina* spp., *Calothrix* spp., *Anabaena flos-aquae, Aphanizomenon* spp., *Anadaena* spp., *Gleotrichia* spp., *Oscillatoria* spp., *Nostoc* spp., *Synechococcus elongatus* 7942, *Synechococcus* spp., *Synechosystis* spp. PCC 6803, *Synechosystis* spp., *Spirulina plantensis, Chaetoceros spp., *Chlamydomonas reinhardii, Chlamydomonas* spp., *Chlorella vulgaris, Chlorella* spp., *Cyclotella* spp., *Didymosphenia* spp., *Dunaliella tertiolecta, Dunaliella* spp., *Botryococcus braunii, Botryococcus* spp., *Gelidium* spp., *Gracilaria* spp., *Hantscia* spp., *Hematococcus* spp., *Isochrysis* spp., *Laminaria* spp., *Navicula* spp., *Pleurochrysis* spp. *Scenedesemus* spp. and *Sargassum* spp.

Figure 10:
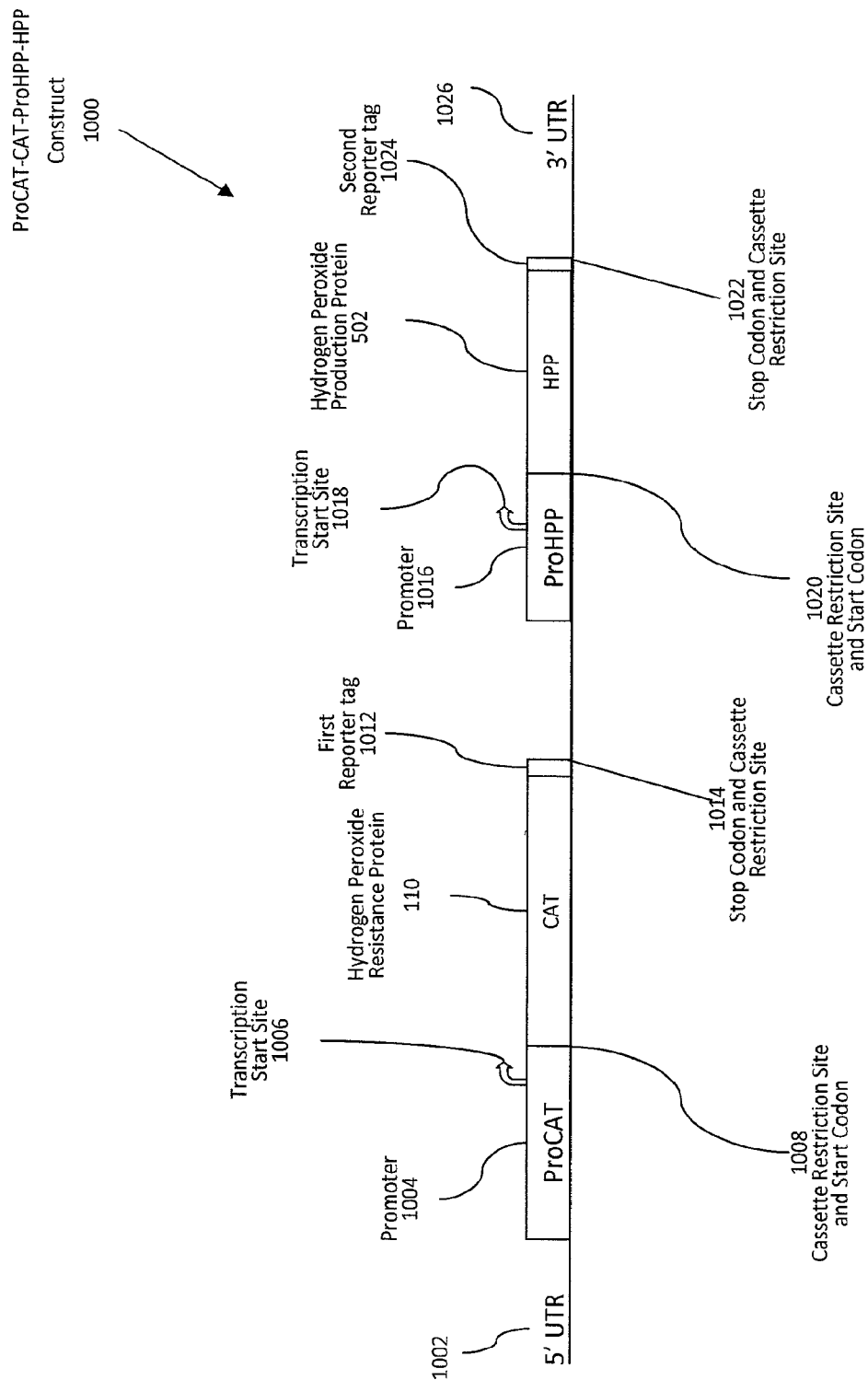
FIG. 10 is a map of a DNA construct, represented as ProCAT-CAT-ProHPP-HPP that includes (from 5' to 3'), a first promoter, a hydrogen peroxide resistance protein coding sequence, a second promoter, and a hydrogen peroxide production protein coding sequence.

As shown in FIG. 10, a construct for expression of a hydrogen peroxide resistance protein and a hydrogen peroxide production protein is generally represented as Pro-CAT-CAT-ProHPP-HPP 1000, where starting at the 5' UTR 1002 an inducible or constitutive transcriptional promoter such as RbcS2 promoter (SEQ ID NO: 15) and the PSAD promoter (SEQ ID NO: 14) is provided as ProCAT 1004 with a transcription start site 1006. CAT 110 is a hydrogen peroxide resistance protein such as the *E. coli* catalase (KatE) (SEQ. ID NO: 3) where the protein has a restriction site and start codon 1008 on the 5' end of the hydrogen peroxide resistance protein 110. A stop codon and 3' cassette restriction site 1014 provides the transcription termination and a reporter peptide tag allows for identification of the protein 1012. The construct further includes an inducible transcriptional promoter such as NIT1 inducible promoter (SEQ ID NO: 16) and CYC6 inducible promoters (SEQ ID NO: 17), constitutive promoters such as the RbcS2 promoter (SEQ ID NO: 15) or a promoter with an associated regulatory element promoter such as the PSAD promoter (SEQ ID NO: 14) is provided as ProHPP 1016 with a transcription start site 1018. HPP 502 is a hydrogen peroxide production protein such as the *Homo sapiens* NADPH oxidase 4 (NOX4) (SEQ ID NO: 1), the *Zea mays* superoxide dismutase4 (sod4) (SEQ ID NO: 5), or the cytochrome b245 protein complex (SEQ ID NO: 7 and SEQ ID NO:9) where the protein has a restriction site and start codon 1020 on the 5' end of the hydrogen peroxide production protein 502. A stop codon and 3' cassette restriction site 1022 provides the transcription termination on the 3'UTR 1026 a second reporter tag which may be a peptide tag such as the FLAG 3x tag 1024 or reporter tag is used to identify the hydrogen peroxide production protein. Each of these components is operably linked to the next, i.e., the first promoter is operably linked to the 5' end of the hydrogen peroxide resistance protein sequence encoding the hydrogen peroxide resistance protein, the hydrogen peroxide resistance protein coding sequence is operably linked to the second promoter coding sequence. The second promoter coding sequence is operably linked to the hydrogen peroxide production coding sequence. The DNA construct ProCAT-CAT-ProHPP-HPP 1000 is then integrated into a photosynthetic unicellular organism such as *Chlamydomonas reinhardtii* and organisms expressing the hydrogen peroxide resistance protein and the hydrogen peroxide production protein, including expression in the outer plasma membrane of the organism, are then generated including but not limited to cyanobacteria including but not limited to *Arthrospira* spp., *Spirulina* spp., *Calothrix* spp., *Anabaena flos-aquae, Aphanizomenon* spp., *Anadaena* spp., *Gleotrichia* spp., *Oscillatoria* spp., *Nostoc* spp., *Synechococcus elongatus* 7942, *Synechococcus* spp., *Synechosystis* spp. PCC 6803, *Synechosystis* spp., *Spirulina* plantensis, *Chaetoceros* spp., *Chlamydomonas reinhardii, Chlamydomonas* spp., *Chlorella vulgaris, Chlorella* spp., *Cyclotella* spp., *Didymosphenia* spp., *Dunaliella tertiolecta, Dunaliella* spp., *Botryococcus braunii, Botryococcus* spp., *Gelidium* spp., *Gracilaria* spp., *Hantscia* spp., *Hematococcus* spp., *Isochrysis* spp., *Laminaria* spp., *Navicula* spp., *Pleurochrysis* spp. *Scenedesemus* spp. and *Sargassum* spp.

Generally, the DNA that is introduced into an organism is part of a construct. A construct is an artificially constructed segment of DNA that may be introduced into a target organism tissue or organism cell. The DNA may be a gene of interest, e.g., a coding sequence for a protein, or it may be a sequence that is capable of regulating expression of a gene, such as an antisense sequence, a sense suppression sequence, or a miRNA sequence. As used herein, "gene" refers to a segment of nucleic acid. A gene can be introduced into a genome of a species, whether from a different species or from the same species. The construct typically includes regulatory regions operably linked to the 5' side of the DNA of interest and/or to the 3' side of the DNA of interest. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation. A cassette containing all of these elements is also referred to herein as an expression cassette. The expression cassettes may additionally contain 5' leader sequences in the expression cassette construct. (A leader sequence is a nucleic acid sequence containing a promoter as well as the upstream region of a gene.) The regulatory regions (i.e., promoters, transcriptional regulatory regions, translational regulatory regions, and translational termination regions) and/or the polynucleotide encoding a signal anchor may be native/analogous to the host cell or to each other. Alternatively, the regulatory regions and/or the polynucleotide encoding a signal anchor may be heterologous to the host cell or to each other. The expression cassette may additionally contain selectable marker genes. See U.S. Pat. No. 7,205,453 and U.S. Patent Application Publication Nos. 2006/0218670 and 2006/0248616. Targeting constructs are engineered DNA molecules that encode genes and flanking sequences that enable the constructs to integrate into the host genome at targeted or random locations. Publicly available restriction proteins may be used for the development of the constructs. Targeting constructs depend upon homologous recombination to find their targets.

The expression cassette or chimeric genes in the transforming vector typically have a transcriptional termination region at the opposite end from the transcription initiation regulatory region. The transcriptional termination region may normally be associated with the transcriptional initiation region from a different gene. The transcriptional termination region may be selected, particularly for stability of the mRNA, to enhance expression. Illustrative transcriptional termination regions include the NOS terminator from *Agrobacterium* Ti plasmid and the rice α-amylase terminator.

Promoters

A promoter is a DNA region, which includes sequences sufficient to cause transcription of an associated (downstream) sequence. The promoter may be regulated, i.e., not constitutively acting to cause transcription of the associated sequence. If inducible, there are sequences present therein which mediate regulation of expression so that the associated sequence is transcribed only when an inducer molecule is present. The promoter may be any DNA sequence which shows transcriptional activity in the chosen cells or organisms. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds, Nucleic Acids Res., 15, 2343-61 (1987). Also, the location of the promoter relative to the transcription start may be optimized. Many suitable promoters for use in algae, plants, and photosynthetic bacteria are well known in the art, as are nucleotide sequences, which enhance expression of an associated expressible sequence.

While the RbcS2 promoter (SEQ ID NO: 15), the PSAD promoter (SEQ ID NO: 14), the NIT1 promoter (SEQ ID NO:16) the CYC6 promoter (SEQ ID NO: 17) and the riboswitch translational regulator (SEQ ID NO:12) or the regulatory region upstream of the protein coding sequences are examples of promoters that may be used, a number of promoters may be used including but not limited to prokaryotic lac and Ptrc promoters and eukaryotic. Promoters can be selected based on the desired outcome. That is, the nucleic acids can be combined with constitutive, tissue-preferred, or other promoters for expression in the host cell of interest. Translational enhancing sequences and outer membrane trafficking signal peptide sequences are assembled around NOX4 as necessary (and is species specific) for proper protein expression and localization to the outer membrane.

Hydrogen Peroxide Resistant and Production Proteins $H_2O_2$ is a simple molecule but its effect on cells can be complex. One reason for this is that, in addition to entering freely into cells from exogenous sources, $H_2O_2$ is produced endogenously by aerobic metabolism, for example during beta-oxidation of fatty acids or photorespiration. Moreover, $H_2O_2$ is a signaling molecule known to activate the SoxR and OxyR regulons, inhibit metabolism and trigger programmed cell death. Various organisms, including humans and bacteria, utilize $H_2O_2$ secretion to defend themselves from pathogens and competitors. A common example is human neutrophils that secrete an "oxidative burst" of lethal $H_2O_2$ to kill invading bacteria that they encounter in blood and tissues. As noted earlier, $H_2O_2$ degrades spontaneously to $H_2O$ and $O_2$ in water. In cells, $H_2O_2$ degradation is highly accelerated by peroxidase and catalase enzymes. Catalases degrade $H_2O_2$ at one of the fastest enzymatic rates known but with a relatively low affinity for the substrate. Peroxidases have a higher affinity for $H_2O_2$ but require electron donors and are thereby integrated with cellular energy metabolism. For example, ascorbate pools in chloroplasts can be higher than 1 mM owing to the need for supplying ascorbate peroxidases with reducing power acquired from photosynthetic electron transport. Heterologous peroxidase expression would require linking the peroxidases with electron donors, native or otherwise, and create the risk of interfering with normal cell functions and compromising growth.

For genetic engineering of resistance to exogenous $H_2O_2$, catalases are better tools because of their high rates of $H_2O_2$ degradation and their lack of integration with other cellular metabolism. Even the relatively poor affinity of catalases for $H_2O_2$ can be an advantage because heterologous catalase expression is thereby less likely to interfere with positive functions of $H_2O_2$ in gene regulation.

Catalases for Hydrogen Peroxide Resistance

Catalases are enzymes found in many living organisms. Catalases provide resistance to hydrogen peroxide by decomposing hydrogen peroxide to water and oxygen.

A. E. coli katE Catalase

The E. coli KatE gene (SEQ ID NO:3) contains the HPII catalase and provides resistance to hydrogen peroxide. The HPII catalase possesses enzymes that serve to decompose hydrogen peroxide into water and oxygen which intern protects host cells from the hydrogen peroxide.

Additional catalases that may be used to express hydrogen peroxide resistance in photosynthetic unicellular organisms includes but is not limited to the CAT2 catalase 2 [*Arabidopsis thaliana*] (GENBANK Accession No. NC_003075, Gene ID: 829661), the cat1 catalase1 [*Zea mays*] (GENBANK Gene ID: 542369), the CAT1 catalase/peroxidase [*Chlamydomonas reinhardtii*] (GENBANK Gene ID: 5722404), and the CAT2 catalase/peroxidase [*Chlamydomonas reinhardtii*] (GENBANK Gene ID: 5715669).

Hydrogen Peroxide Production Proteins

A. Human NOX4 Protein

The human Nox4 (SEQ ID NO: 1) protein is a transmembrane bound NADPH oxidase which produces hydrogen peroxide. Nox4 is relatively unique among the Nox family of proteins in that it constitutively produces large amounts of hydrogen peroxide without concomitant superoxide preformation. Nox4 also requires no regulatory mechanisms for activity such as subunit assembly, cytosolic activation factors or Rac-type GTPases and activity is believed to occur without post translational modifications such as glycosylation.

B. *Zea mays* Superoxide Dismutase (SOD4)

The *Zea mays* SOD4 gene produces superoxide dismutase enzymes (SEQ ID NO:5) that generate hydrogen peroxide by catalyzing the redox reaction of superoxide into oxygen and hydrogen peroxide.

C. Cytochrome

Cytochrome b245 is a protein complex composed of cytochrome b alpha and beta chain CYBB (SEQ ID NO:7) and CYBA (SEQ ID NO:9). Cytochrome b245 is a component of the membrane-bound oxidase of phagocytes that generates hydrogen peroxide. It is the terminal component of a respiratory chain that transfers single electrons from cytoplasmic NADPH across the plasma membrane to molecular oxygen on the exterior. Cytochrome b245 participates in the regulation of cellular pH and is blocked by zinc. Cytochrome b245 is made of two subunits: a light chain and a heavy chain. The sequences for both subunits (SEQ ID NO: 7 and SEQ ID NO:9) must be expressed in tandem to assemble a functional cytochrome Vector Construction, Transformation, and Heterologous Protein Expression As used herein plasmid, vector or cassette refers to an extrachromosomal element often carrying genes and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with an appropriate 3' untranslated sequence into a cell.

An example of an expression vector is a *Chlamydomonas* expression vector designated pSI105, derivatives of the vectors described herein may be capable of stable transformation of many photosynthetic unicells, including but not limited to unicellular algae of many species, photosynthetic bacteria, and single photosynthetic cells, e.g. protoplasts, derived from the green parts of plants. Vectors for stable transformation of algae, bacteria, and plants are well known in the art and can be obtained from commercial vendors. Expression vectors can be engineered to produce heterologous and/or homologous protein(s) of interest (e.g., antibodies, mating type agglutinins, etc.). Such vectors are useful for recombinantly producing the protein of interest.

Such vectors are also useful to modify the natural phenotype of host cells (e.g., expressing a hydrogen peroxide production protein and a hydrogen peroxide resistance protein).

To construct the vector, the upstream DNA sequences of a gene expressed under control of a suitable promoter may be restriction mapped and areas important for the expression of the protein characterized. The exact location of the start codon of the gene is determined and, making use of this information and the restriction map, a vector may be designed for expression of a heterologous protein by removing the region responsible for encoding the gene's protein but leaving the upstream region found to contain the genetic material responsible for control of the gene's expression. A synthetic oligonucleotide is preferably inserted in the location where the protein sequence once was, such that any additional gene could be cloned in using restriction endonuclease sites in the synthetic oligonucleotide (i.e., a multicloning site). An unrelated gene (or coding sequence) inserted at this site would then be under the control of an extant start codon and upstream regulatory region that will drive expression of the foreign (i.e., not normally present) protein encoded by this gene. Once the gene for the foreign protein is put into a cloning vector, it can be introduced into the host organism using any of several methods, some of which might be particular to the host organism. Variations on these methods are described in the general literature. Manipulation of conditions to optimize transformation for a particular host is within the skill of the art.

The basic transformation techniques for expression in photosynthetic unicells are commonly known in the art. These methods include, for example, introduction of plasmid transformation vectors or linear DNA by use of cell injury, by use of biolistic devices, by use of a laser beam or electroporation, by microinjection, or by use of *Agrobacterium tumifaciens* for plasmid delivery with transgene integration or by any other method capable of introducing DNA into a host cell.

In some embodiments, biolistic plasmid transformation of the chloroplast genome can be achieved by introducing regions of chloroplast DNA flanking a desired nucleotide sequence, allowing for homologous recombination of the exogenous DNA into the target chloroplast genome. Plastid transformation is routine and well known in the art (see U.S. Pat. Nos. 5,451,513, 5,545,817, and 5,545,818; WO 95/16783; McBride et al., *Proc. Natl. Acad. Sci.*, USA 91:7301-7305, 1994). In some instances one to 1.5 kb flanking nucleotide sequences of chloroplast genomic DNA may be used. Using this method, point mutations in the chloroplast 16S rRNA and rps12 genes, which confer resistance to spectinomycin and streptomycin, can be utilized as selectable markers for transformation and can result in stable homoplasmic transformants, at a frequency of approximately one per 100 bombardments of target cells (Svab et al., *Proc. Natl. Acad. Sci., USA* 87:8526-8530, 1990).

Biolistic microprojectile-mediated transformation also can be used to introduce a polynucleotide into photosynthetic unicells for nuclear integration. This method utilizes microprojectiles such as gold or tungsten, which are coated with the desired polynucleotide by precipitation with calcium chloride, spermidine or polyethylene glycol. The microprojectile particles are accelerated at high speed into cells using a device such as the BIOLISTIC PD-1000 particle gun. Methods for the transformation using biolistic methods are well known in the art. Microprojectile mediated transformation has been used, for example, to generate a variety of transgenic organisms. Transformation of photosynthetic unicells also can be transformed using, for example, biolistic methods as described above, protoplast transformation, electroporation of partially permeabilized cells, introduction of DNA using glass fibers, the glass bead agitation method, and the like. Transformation frequency may be increased by replacement of recessive rRNA or r-protein antibiotic resistance genes with a dominant selectable marker, including, but not limited to the bacterial aadA gene (Svab and Maiiga, *Proc. Natl. Acad. Sci.*, USA 90:913-917, 1993).

The basic techniques used for transformation and expression in photosynthetic organisms are known in the art. These methods have been described in a number of texts for standard molecular biological manipulation (see Packer & Glaser, 3988, "Cyanobacteria", *Meth. Enzymol.*, Vol. 167; Weissbach & Weissbach, 1988, "Methods for plant molecular biology," Academic Press, New York, Sambrook, Fritsch & Maniatis, 1989, "Molecular Cloning: A laboratory manual," 2nd edition Cold Spring Harbor Laboratory Press, Cold Spring Harbor, N.Y.; and Clark M S, 1997, Plant Molecular Biology, Springer, N.Y.). These methods include, for example, biolistic devices (See, for example, Sanford, Trends In Biotech. (1988) 6: 299-302, U.S. Pat. No. 4,945,050); electroporation (Fromm et al., Proc. Nat'l. Acad. Sci. (USA) (1985) 82: 5824-5828); use of a laser beam, electroporation, microinjection or any other method capable of introducing DNA into a host cell (e.g., an NVPO).

Other transformation methods are available to those skilled in the art, such as direct uptake of foreign DNA constructs (see EP 295959), techniques of electroporation (see Fromm et al. (1986) Nature (London) 319:791) or high-velocity ballistic bombardment with metal particles coated with the nucleic acid constructs (see Kline et al. (1987) Nature (London) 327:70, and see U.S. Pat. No. 4,945,050).

To confirm the presence of the transgenes in transgenic cells, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different photosynthetic unicellular organisms is to use a reporter gene, such as GUS. Once transgenic organisms have been obtained, they may be grown to produce organisms or parts having the desired phenotype.

Use of a Selectable Marker (SM)

A selectable marker can provide a means to obtain photosynthetic unicells that express the marker and, therefore, can be useful as a component of a vector. Examples of selectable markers include, but are not limited to, those that confer antimetabolite resistance, for example, dihydrofolate reductase, which confers resistance to methotrexate; neomycin phosphotransferase, which confers resistance to the aminoglycosides neomycin, kanamycin and paromycin (SEQ ID NO:12 and SEQ ID NO:13); hygro, which confers resistance to hygromycin, trpB, which allows cells to utilize indole in place of tryptophan; hisD, which allows cells to utilize histinol in place of histidine; mannose-6-phosphate isomerase which allows cells to utilize mannose; ornithine decarboxylase, which confers resistance to the ornithine decarboxylase inhibitor, 2-(difluoromethyl)-DL-ornithine; and deaminase from *Aspergillus terreus*, which confers resistance to *Blasticidin S*. Additional selectable markers include those that confer herbicide resistance, for example, phosphinothricin acetyltransferase gene, which confers resistance to phosphinothricin, a mutant EPSPV-synthase, which confers glyphosate resistance, a mutant acetolactate synthase, which confers imidazolone or sulfonylurea resistance, a mutant psbA, which confers resistance to atrazine, or a mutant protoporphyrinogen oxidase, or other markers conferring resistance to an herbicide such as glufosinate. Selectable markers include polynucleotides that confer dihydrofolate reductase (DHFR) or neomycin resistance for eukaryotic cells and tetracycline; ampicillin resistance for prokaryotes such as *E. coli*; and bleomycin, gentamycin, glyphosate, hygromycin, kanamycin, methotrexate, phleomycin, phosphinothricin, spectinomycin, streptomycin, sulfonamide and sulfonylurea resistance in plants.

Fluorescent peptide (FP) fusions allow analysis of dynamic localization patterns in real time. Over the last several years, a number of different colored fluorescent peptides have been developed and may be used in various constructs, including yellow FP (YFP), cyan FP (CFP), red FP (mRFP) and others. Some of these peptides have improved spectral properties, allowing analysis of fusion proteins for a longer period of time and permitting their use in photobleaching experiments. Others are less sensitive to pH, and other physiological parameters, making them more suitable for use in a variety of cellular contexts. Additionally, FP-tagged proteins can be used in protein-protein interaction studies by bioluminescence resonance energy transfer (BRET) or fluorescence resonance energy transfer (FRET). High-throughput analyses of FP fusion proteins in *Arabidopsis* have been performed by overexpressing cDNA-GFP fusions driven by strong constitutive promoters. A standard protocol is to insert the mRFP tag or marker at a default position of ten amino acids upstream of the stop codon, following methods established for *Arabidopsis* (Tian et al. High through put fluorescent tagging of full-length *Arabidopsis* gene products in plants. *PlantPhysiol.* 135 25-38). Although useful, this approach has inherent limitations, as it does not report tissue-specificity, and overexpression of multimeric proteins may disrupt the complex. Furthermore, overexpression can lead to protein aggregation and/or mislocalization.

In order to tag a specific gene with a fluorescent peptide such as the red fluorescent protein (mRFP), usually a gene ideal for tagging has been identified through forward genetic analysis or by homology to an interesting gene from another model system. For generation of native expression constructs, full-length genomic sequence is required. For tagging of the full-length gene with an FP, the full-length gene sequence should be available, including all intron and exon sequences. A standard protocol is to insert the mRFP tag or marker at a default position of ten amino acids upstream of the stop codon, following methods known in the art established for photosynthetic unicells. The rationale is to avoid masking N-terminal targeting signals (such as endoplasmic reticulum (ER) retention or peroxisomal signals). In addition, by avoiding the N-terminus, disruption of N-terminal targeting sequences or transit peptides is avoided. However, choice of tag insertion is case-dependent, and it should be based on information on functional domains from database searches. If a homolog of the gene of interest has been successfully tagged in another organism, this information is also used to choose the optimal tag insertion site.

Flag tags or reporter tags/epitopes, such as artificial genes with 5' and 3' restriction sites and C-terminal 3X FLAG tags are another mechanism to allow for analysis of the location and presence of a gene. The C-terminal FLAG tag/epitope allows screening of transformants and analysis of protein expression by standard Western blot using commercially available anti-FLAG M2 primary antibody.

Linker

A flexible linker peptide may be placed between proteins such that the desired protein is obtained. A cleavable linker peptide may also be placed between proteins such that they can be cleaved and the desired protein obtained. An example of a flexible linker may include (GSS)2, which is a flexible linker added by the reverse primer.

Transcription Terminator

The transcription termination region of the constructs is a downstream regulatory region including the stop codon TGA and the cassette restriction site of the sequence. Alternative transcription termination regions which may be used may be native with the transcriptional initiation region, may be native with the DNA sequence of interest, or may be derived from another source. The transcription termination region may be naturally occurring, or wholly or partially synthetic. Convenient transcription termination regions are available from the Ti-plasmid of *Agrobacterium tumefaciens*, such as the octopine synthase and nopaline synthase transcription termination regions or from the genes for beta-phaseolin, the chemically inducible plant gene, pIN.

Growing a Transgenic Unicellular Organism

A variety of methods are available for growing photosynthetic unicellular organisms. Cells can be successfully grown in a variety of media including agar and liquid, with shaking or mixing. Long term storage of cells can be achieved using plates and storing a 10-15° C. Cells may be stored in agar tubes, capped and grown in a cool, low light storage area. Photosynthetic unicells are usually grown in a simple medium with light as the sole energy source including in closed structures such as photobioreactors, where the environment is under strict control. A photobioreactor is a bioreactor that incorporates a light source.

While the techniques necessary for growing unicellular organisms are known in the art, an example method of growing unicells may include using a liquid culture for growth including 100 µl of 72 hr liquid culture used to inoculate 3 ml of medium in 12 well culture plates that are grown for 24 hrs in the light with shaking.

Another example may include the use of 300 ul of 72 hr liquid culture used to inoculate 5 ml of medium in 50 ml culture tubes where the unicells cultures are grown for 72 hrs under light with shaking. Cultures are vortexed and photographed. Cultures are then left to settle for 10 min and photographed again.

The practice described herein employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis, et al., *Molecular Cloning*, Cold Spring Harbor Laboratory Press, Cold Spring Harbor, N.Y. (1982); Sambrook, et al., *Molecular Cloning, 2nd Ed.*, Cold Spring Harbor Laboratory Press, Cold Spring Harbor, N.Y. (1989); Sambrook and Russell, *Molecular Cloning, 3rd Ed.*, Cold Spring Harbor Laboratory Press, Cold Spring Harbor, N.Y. (2001); Ausubel, et al., *Current Protocols in Molecular Biology*, John Wiley & Sons (including periodic updates) (1992); Glover, *DNA Cloning*, IRL Press, Oxford (1985); Russell, *Molecular biology of plants: a laboratory course manual*, Cold Spring Harbor Laboratory Press, Cold Spring Harbor, N.Y. (1984); Anand, *Techniques for the Analysis of Complex Genomes*, Academic Press, NY (1992); Guthrie and Fink, *Guide to Yeast Genetics and Molecular Biology*, Academic Press, NY (1991); Harlow and Lane, *Antibodies*, Cold Spring Harbor Laboratory Press, Cold Spring Harbor, N.Y. (1988); *Nucleic Acid Hybridization*, B. D. Hames & S. J.

Higgins eds. (1984); *Transcription And Translation*, B. D. Hames & S. J. Higgins eds. (1984); *Culture Of Animal Cells*, R. I. Freshney, A. R. Liss, Inc. (1987); *Immobilized Cells And Enzymes*, IRL Press (1986); B. Perbal, *A Practical Guide To Molecular Cloning* (1984); the treatise, Methods In Enzymology, Academic Press, Inc., NY); *Methods In Enzymology*, Vols. 154 and 155, Wu, et al., eds.; *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds. (1986); Riott, *Essential Immunology*, 6th Edition, Blackwell Scientific Publications, Oxford (1988); Fire, et al., *RNA Interference Technology: From Basic Science to Drug Development*, Cambridge University Press, Cambridge (2005); Schepers, *RNA Interference in Practice*, Wiley VCH (2005); Engelke, *RNA Interference (RNAi): The Nuts & Bolts of siRNA Technology*, DNA Press (2003); Gott, *RNA Interference, Editing, and Modification: Methods and Protocols (Methods in Molecular Biology)*, Human Press, Totowa, N.J. (2004); and Sohail, *Gene Silencing by RNA Interference: Technology and Application*, CRC (2004).

EXAMPLES

The following examples are provided to illustrate further the various applications and are not intended to limit the invention beyond the limitations set forth in the appended claims.

Example 1

Use of Selectable Marker to Quantify Hydrogen Peroxide Resistance

The cell wall-deficient CC-400 cw15 mt+ strain of *C. reinhardtii* is used as genetic background for transformations. Cultures are maintained on liquid and solid (1.5% agar) tris-acetate-phosphate (TAP) growth medium (Gorman & Levine 1965) under continuous 60 µEm-2s-1 cool white fluorescent light at 25 C. Liquid cultures for physiological analyses, such as catalase assays, are grown under the same conditions except that lighting is on a diurnal cycle of 16 h light, 8 h dark, which is more consistent with outdoor growing conditions than is continuous light.

Standard methods for generating recombinant DNA expression vectors and expressing heterologous proteins in *C. reinhardtii* are employed (see Sambrook and Russell 2001 and Heitzer and Zschoernig 2007). *C. reinhardtii* codon bias, as described by Fuhrman and Hegemann (1997), is used by adapting the *E. coli* catalase (KatE) (open reading frame (ORF)). (Additional catalases that may be used to express hydrogen peroxide resistance in photosynthetic unicellular organisms include but are not limited to the CAT2 catalase 2 [*Arabidopsis thaliana*] (GENBANK Accession No. NC_003075, Gene ID: 829661), cat1 catalase1 [*Zea mays*] (GENBANK Gene ID: 542369), the CAT1 catalase/peroxidase [*Chlamydomonas reinhardtii*] (GENBANK Gene ID: 5722404), and the CAT2 catalase/peroxidase [*Chlamydomonas reinhardtii*] (GENBANK Gene ID: 5715669)). Artificial genes with 5' and 3' restriction sites and C-terminal 3X FLAG tags are synthesized using a service provider such as GenScript Corporation, Piscataway, N.J. Restriction sites are used to ligate and clone the synthesized ORF and fusion sequences into the *C. reinhardtii* expression vector pChlamy_1, which is available from Life Technologies Corporation, Grand Island, N.Y. The pChlamy_1 vector systems harbor effective selection markers and are optimized for transgene expression in *C. reinhardtii*. Public domain expression vectors based on the pS1105 system (Couso et al. 2011) are also available for *C. reinhardtii* and are utilized for later stages of this project. For localization of the catalase to the inner face of the plasma membrane, an N-terminal GPI anchor sequence for a membrane anchoring protein domain are added to the 5' end of the transgene coding sequence. The C-terminal FLAG tag/epitope allows screening of transformants and analysis of protein expression by standard Western blot using commercially available anti-FLAG M2 primary antibody. Chromogenic detection of primary antibody is mediated by an anti-mouse alkaline phosphatase-conjugated secondary antibody and NBT-BCIP substrate. Transformations are done according to the nuclear glass bead method (Kindle 1990) (this is the method used for each transgene).

Transformed lines of *C. reinhardtii* that show evidence of heterologous catalase expression in Western blots are grown to 106 cells/ml in liquid medium and tested for in vivo catalase activity using an assay based on the initial rate of $O_2$ evolution in response to addition of exogenous $H_2O_2$ to intact cells (Thomas et al. 1998). $O_2$ evolution is measured in a Clark-type $O_2$ electrode. The assay is simple and fast, allowing Km and Vmax values for total catalase activity to be determined in cell suspensions with relative ease. The assay is also sensitive enough that replica-plated single colonies of transformants can be suspended in solution and their catalase activity measured accurately, allowing early screening for catalase activity before possible decay of transgene expression can occur. Untransformed and empty vector control strains therefore exhibit background catalase activity (this is the assay for catalase expressing strains).

Analyses of growth is made for all transformed lines with addition of the $H_2O_2$-based algaecide PAK™27 from Morgan & Associates, Inc. (Peroxygen Solutions), Greensboro, N.C., over a range of concentrations, from benign to completely lethal. Growth are tested in 10 ml liquid batch cultures. The cultures are grown in 25×200 mm culture tubes slanted at 15° on an orbital shaker set to 150 rpm.

Liquid cultures for growth experiments are started from replica plated cultures on agar slants and grown to saturation under unstressed conditions (108 cells/ml or more). The cultures are then diluted to approximately 0.5×106 cells/ml with fresh medium and returned to unstressed conditions. After 24 h adjustment to the dilution, PAK™27 doses are applied and cell density measured at 24 h intervals over 72 h by apparent absorbance at 750 nm (A750), which is proportional to light scattering and linear with cells/ml (Thomas 1998). Growth rates for the different tubes are calculated as hours required for cell doubling averaged over 72 h.

Example 2

Expression of the NOX4 Protein for Hydrogen Peroxide Production in *C. reinhardtii*

The cell wall-deficient CC-400 cw15 mt+ strain of *C. reinhardtii* is used as genetic background for transformations. Cultures are maintained on liquid and solid (1.5% agar) tris-acetate-phosphate (TAP) growth medium under continuous 60 µEm-2s-1 cool white fluorescent light at 25 C. Liquid cultures for physiological analyses, such as oxidase assays, are grown under the same conditions except that lighting is on a diurnal cycle of 16 h light, 8 h dark, which is more consistent with outdoor growing conditions than is continuous light.

Standard methods for generating recombinant DNA expression vectors and expressing heterologous proteins in *C. reinhardtii* are employed. *C. reinhardtii* codon bias, as described by Fuhrman and Hegemann (1997), is used by adapting the human Nox4 (SEQ ID NO: 1) protein (open reading frame (ORF)). Artificial genes with 5' and 3' restriction sites and C-terminal 3X FLAG tags are synthesized using a service provider such as GenScript. Restriction sites are used to ligate and clone the synthesized ORF and fusion sequences into the *C. reinhardtii* expression vector pChlamy_1, which is available from Life Technologies Corporation. The pChlamy_1 vector systems harbor effective selection markers and are optimized for transgene expression in *C. reinhardtii*. Public domain expression vectors based on the pS1105 system are also available for *C. reinhardtii* and are utilized for later stages of this project. For localization of catalase to the inner face of the plasma membrane, an N-terminal GPI anchor sequence for a membrane anchoring protein domain are added to the 5' end of the transgene coding sequence. The C-terminal FLAG tag/epitope allows screening of transformants and analysis of protein expression by standard Western blot using commercially available anti-FLAG M2 primary antibody. Chromogenic detection of primary antibody is mediated by an anti-mouse alkaline phosphatase-conjugated secondary antibody and NBT-BCIP substrate. Transformations are done according to the nuclear glass bead method.

Transformed lines of *C. reinhardtii* that show evidence of heterologous oxidase expression in Western blots are grown to 106 cells/ml in liquid medium and tested for in vivo oxidase activity using an assay based on the initial rate of $O_2$ evolution in response to addition of exogenous $H_2O_2$ to intact cells. $O_2$ evolution is measured in a Clark-type $O_2$ electrode. The assay is simple and fast, allowing Km and Vmax values for total oxidase activity to be determined in cell suspensions with relative ease. The assay is also sensitive enough that replica-plated single colonies of transformants can be suspended in solution and their oxidase activity measured accurately, allowing early screening for oxidase activity before possible decay of transgene expression can occur. Untransformed and empty vector control strains therefore exhibit background oxidase activity (this is the assay for oxidase expressing strains).

Analyses of growth is made for all transformed lines with addition of the $H_2O_2$ based algaecide PAK™27 over a range of concentrations, from benign to completely lethal. Growth are tested in 10 ml liquid batch cultures. The cultures are grown in 25×200 mm culture tubes slanted at 15° on an orbital shaker set to 150 rpm.

Liquid cultures for growth experiments are started from replica plated cultures on agar slants and grown to saturation under unstressed conditions (108 cells/ml or more). The cultures are then diluted to approximately 0.5×106 cells/ml with fresh medium and returned to unstressed conditions. After 24 h adjustment to the dilution, PAK™27 doses are applied and cell density measured at 24 h intervals over 72 h by apparent absorbance at 750 nm (A750), which is proportional to light scattering and linear with cells/ml. Growth rates for the different tubes are calculated as hours required for cell doubling averaged over 72 h.

Example 3

Expression of the SOD4 Protein for Hydrogen Peroxide Production in *C. reinhardtii*

The cell wall-deficient CC-400 cw15 mt+ strain of *C. reinhardtii* is used as genetic background for transformations. Cultures are maintained on liquid and solid (1.5% agar) tris-acetate-phosphate (TAP) growth medium under continuous 60 µEm-2s-1 cool white fluorescent light at 25 C. Liquid cultures for physiological analyses, such as oxidase assays, are grown under the same conditions except that lighting is on a diurnal cycle of 16 h light, 8 h dark, which is more consistent with outdoor growing conditions than is continuous light.

Standard methods for generating recombinant DNA expression vectors and expressing heterologous proteins in *C. reinhardtii* are employed. *C. reinhardtii* codon bias, as described by Fuhrman and Hegemann (1997), is used by adapting the maize SOD4 (SEQ ID NO: 5) protein (open reading frame (ORF)). Artificial genes with 5' and 3' restriction sites and C-terminal 3X FLAG tags are synthesized using a service provider such as GenScript. Restriction sites are used to ligate and clone the synthesized ORF and fusion sequences into the *C. reinhardtii* expression vector pChlamy_1, which is available from Life Technologies Corporation. The pChlamy_1 vector systems harbor effective selection markers and are optimized for transgene expression in *C. reinhardtii*. Public domain expression vectors based on the pS1105 system are also available for *C. reinhardtii* and are utilized for later stages of this project. For localization of the oxidase to the inner face of the plasma membrane, an N-terminal GPI anchor sequence for a membrane anchoring protein domain are added to the 5' end of the transgene coding sequence. The C-terminal FLAG tag/epitope allows screening of transformants and analysis of protein expression by standard Western blot using commercially available anti-FLAG M2 primary antibody. Chromogenic detection of primary antibody is mediated by an anti-mouse alkaline phosphatase-conjugated secondary antibody and NBT-BCIP substrate. Transformations are done according to the nuclear glass bead method.

Transformed lines of *C. reinhardtii* that show evidence of heterologous oxidase expression in Western blots are grown to 106 cells/ml in liquid medium and tested for in vivo oxidase activity using an assay based on the initial rate of $O_2$ evolution in response to addition of exogenous $H_2O_2$ to intact cells. $O_2$ evolution is measured in a Clark-type $O_2$ electrode. The assay is simple and fast, allowing Km and Vmax values for total oxidase activity to be determined in cell suspensions with relative ease. The assay is also sensitive enough that replica-plated single colonies of transformants can be suspended in solution and their oxidase activity measured accurately, allowing early screening for oxidase activity before possible decay of transgene expression can occur. Untransformed and empty vector control strains therefore exhibit background oxidase activity (this is the assay for oxidase expressing strains).

Analyses of growth is made for all transformed lines with addition of the $H_2O_2$-based algaecide PAK™27 over a range of concentrations, from benign to completely lethal. Growth are tested in 10 ml liquid batch cultures. The cultures are grown in 25×200 mm culture tubes slanted at 15° on an orbital shaker set to 150 rpm.

Liquid cultures for growth experiments are started from replica plated cultures on agar slants and grown to saturation under unstressed conditions (108 cells/ml or more). The cultures are then diluted to approximately 0.5×106 cells/ml with fresh medium and returned to unstressed conditions. After 24 h adjustment to the dilution, PAK™27 doses are applied and cell density measured at 24 h intervals over 72 h by apparent absorbance at 750 nm (A750), which is proportional to light scattering and linear with cells/ml.

Growth rates for the different tubes are calculated as hours required for cell doubling averaged over 72 h.

Example 4

Expression of the Cytochrome b-245, Beta Polypeptide (CYBB and CYBA) Protein Complex for Hydrogen Peroxide Production in *C. reinhardtii*

The cell wall-deficient CC-400 cw15 mt+ strain of *C. reinhardtii* is used as genetic background for transformations. Cultures are maintained on liquid and solid (1.5% agar) tris-acetate-phosphate (TAP) growth medium under continuous 60 μEm-2s-1 cool white fluorescent light at 25 C. Liquid cultures for physiological analyses, such as oxidase assays, are grown under the same conditions except that lighting is on a diurnal cycle of 16 h light, 8 h dark, which is more consistent with outdoor growing conditions than is continuous light.

Standard methods for generating recombinant DNA expression vectors and expressing heterologous proteins in *C. reinhardtii* are employed. *C. reinhardtii* codon bias is used by adapting the cytochrome (CYBB and CYBA) protein complex (SEQ ID NO: 7 and SEQ ID NO:9) protein (open reading frame (ORF)). Artificial genes with 5' and 3' restriction sites and C-terminal 3X FLAG tags are synthesized using a service provider such as GenScript. Restriction sites are used to ligate and clone the synthesized ORF and fusion sequences into the *C. reinhardtii* expression vector pChlamy_1, which is available from Life Technologies Corporation. The pChlamy_1 vector systems harbor effective selection markers and are optimized for transgene expression in *C. reinhardtii*. Public domain expression vectors based on the pS1105 system are also available for *C. reinhardtii* and are utilized for later stages of this project. For localization of the oxidase to the inner face of the plasma membrane, an N-terminal GPI anchor sequence for a membrane anchoring protein domain are added to the 5' end of the transgene coding sequence. The C-terminal FLAG tag/epitope allows screening of transformants and analysis of protein expression by standard Western blot using commercially available anti-FLAG M2 primary antibody. Chromogenic detection of primary antibody is mediated by an anti-mouse alkaline phosphatase-conjugated secondary antibody and NBT-BCIP substrate. Transformations are done according to the nuclear glass bead method.

Transformed lines of *C. reinhardtii* that show evidence of heterologous oxidase expression in Western blots are grown to 106 cells/ml in liquid medium and tested for in vivo oxidase activity using an assay based on the initial rate of $O_2$ evolution in response to addition of exogenous $H_2O_2$ to intact cells. $O_2$ evolution is measured in a Clark-type $O_2$ electrode. The assay is simple and fast, allowing Km and Vmax values for total oxidase activity to be determined in cell suspensions with relative ease. The assay is also sensitive enough that replica-plated single colonies of transformants can be suspended in solution and their oxidase activity measured accurately, allowing early screening for oxidase activity before possible decay of transgene expression can occur. Untransformed and empty vector control strains therefore exhibit background oxidase activity (this is the assay for oxidase expressing strains).

Analyses of growth is made for all transformed lines with addition of the $H_2O_2$-based algaecide PAK™27 over a range of concentrations, from benign to completely lethal. Growth are tested in 10 ml liquid batch cultures. The cultures are grown in 25×200 mm culture tubes slanted at 15° on an orbital shaker set to 150 rpm.

Liquid cultures for growth experiments are started from replica plated cultures on agar slants and grown to saturation under unstressed conditions (108 cells/ml or more). The cultures are then diluted to approximately 0.5×106 cells/ml with fresh medium and returned to unstressed conditions. After 24 h adjustment to the dilution, PAK™27 doses are applied and cell density measured at 24 h intervals over 72 h by apparent absorbance at 750 nm (A750), which is proportional to light scattering and linear with cells/ml. Growth rates for the different tubes are calculated as hours required for cell doubling averaged over 72 h.

Example 5

Dose Response Data Collected for 2 Strains of Cyanobacteria Exposed to Exogenous $H_2O_2$ These experiments generate dose response curves for growth versus $H_2O_2$-based algaecide concentration. The curves are used to determine the EC50 for growth, which is the "Effective Concentration" of a stressor, in this case $H_2O_2$, that inhibits growth rate by 50% relative to unstressed controls. EC50 for growth rate is determined from non-linear regression curves fitted to growth rate data from 5-7 experimental replicates at 5 to 7 stress doses. To fit curves, non-linear regressions are applied to the dose response data and the fit of the regression curve to the log-logistic equation will be F-tested. Other parameters can be calculated from the regression curve, including EC90, EC10, and the slope of the curve as it passes through the EC50 value, which can suggest mechanisms by which the stressor inhibits growth. PAK™ includes several inactive ingredients intended to maximize the biocidal effect of $H_2O_2$. To confirm that heterologous catalase expressors are resistant to $H_2O_2$ and not to the inactive ingredients, EC50 values for pure $H_2O_2$ is also determined for comparison.

Figure 11:
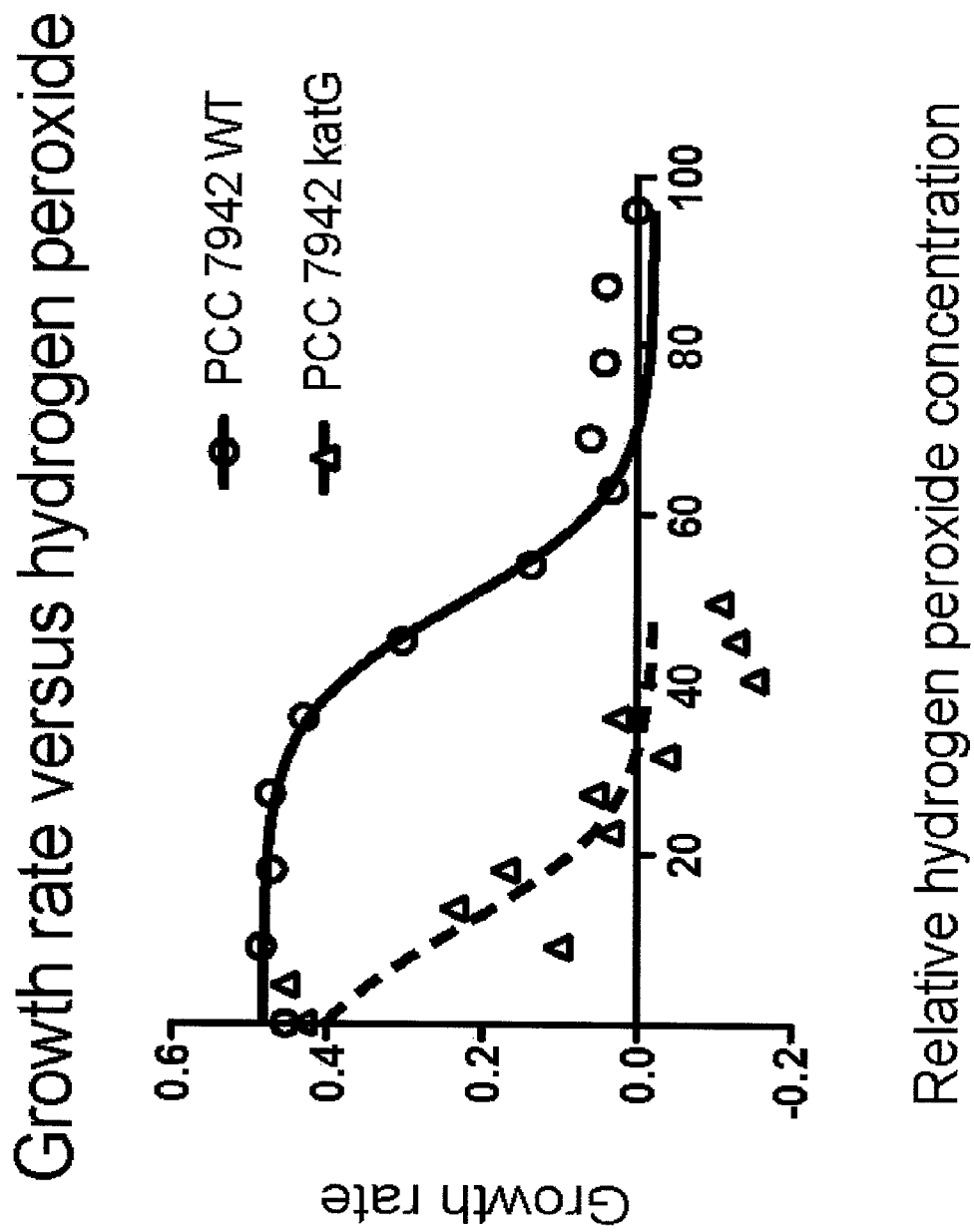
FIG. 11 is a graph showing the dose-response curves for two strains of the cyanobacterium *Synechococcus elongatus* PCC 7942 exposed to varying concentrations of exogenous H$_2$O$_2$. One of the strains lacks catalase activity and its great sensitivity to exogenous H$_2$O$_2$ validates the strategy of overexpressing catalase to achieve H$_2$O$_2$ resistance.

FIG. 11 shows an example of dose response data collected for 2 strains of cyanobacteria exposed to exogenous $H_2O_2$. One of these strains was a wild type (WT) and one was an insertional null mutant for the major cyanobacterial catalase encoded by the katG gene. Visually, it is clear from the data that the strain lacking KatG was much more sensitive to exogenous $H_2O_2$ than the wild type. Non-linear regression analysis of these data quantified the difference between strains, indicating that normal presence of KatG in the wild type conferred nearly a 2-fold resistance to exogenous $H_2O_2$ relative to the null mutant lacking catalase activity. These data prove that catalase activity confers resistance to exogenous $H_2O_2$.

Example 6

Expression of Hydrogen Peroxide Resistance and Hydrogen Peroxide Production in *C. reinhardtii*

For the expression of both hydrogen peroxide resistance and hydrogen peroxide production traits in photosynthetic unicellular organisms, individual lines of photosynthetic unicellular organisms, each possessing either the resistance or the production trait are identified and selected using the methods discussed above. Pedigree breeding, or a similar technique may be used to combine favorable genes, namely hydrogen peroxide resistance with hydrogen peroxide production into a totally new photosynthetic unicellular organism. Two organisms which possess the traits are crossed to produce an $F_1$ (filial generation 1). Selection of desirable individual organisms may begin as early as the $F_1$ generation, and additional selection can occur for one or more generations. Once a progeny organism is selected as having desirable traits, such as the resistance and production traits, additional lines of organisms may be developed from the same original population.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

INDUSTRIAL APPLICATIONS

Renewable liquid fuels and other low-cost commodities can be derived from microalgae and these can ultimately be cost-competitive with petroleum-derived alternatives. Key technological breakthroughs must occur first, however. One of these is that control of unwanted microorganisms in large-scale cultures of algae must become cheap, effective, and environmentally. Microbial pests limit productivity of large-scale algal cultures by competing with desired algae for light and nutrients or by grazing on them. For example, rotifers and other grazers have been shown to lower algal culture concentrations by 90% in only two days and by 99% over several days. A second breakthrough needed to make algal products cost-competitive with petroleum products is that water and nutrient costs for large-scale algal cultures must be reduced. Current estimates put these costs at 10-30% of total production costs. One solution to this problem is utilization of sewage and other wastewaters from municipal and industrial sources but these typically contain microbial pests and organic contaminants. Recycling of used culture water after algal harvesting will also be necessary to minimize the consumption of water by algal biomass production but this presents a similar problem because used culture water can be heavily contaminated with microbial pests and organic wastes, some of which inhibit algal growth.

Production of low cost commodities by terrestrial agriculture would not be possible without the use of sophisticated herbicides and pesticides for control of unwanted plants, animals, fungi, and insects. In contrast, chemical management of pests in large-scale algal cultures is a very poorly developed technology. Existing algaecides approved for control of algal blooms in managed bodies of water (are a starting point for improvement. These are largely based on copper (Cu) and can be highly effective, with the benefit that Cu is initially very toxic to cyanobacteria and to animal grazers but has a low residual activity. Cu is a micronutrient and is detoxified in natural waters by biological sequestration. In some cases, however, addition of Cu to large-scale algal cultures could affect downstream processes, such as the use of algal biomass for aquaculture feeds. Shrimp and other crustaceans, for example, are extremely sensitive to Cu. Presence of Cu could also be harmful to downstream catalysts used for refining of algal biomass, some of which may be sensitive to transition metals (Mitchell 1980), or to biological water treatments used for recycling culture water.

Alternatives to Cu-based algaecides include recently developed products that generate $H_2O_2$ when dissolved in water. $H_2O_2$ is a broad-spectrum biocide that oxidizes organic pollutants in addition to killing microbes and has little residual activity owing to the fact that it quickly and spontaneously decomposes to $H_2O$ and $O_2$. A possible disadvantage of some $H_2O_2$-based algaecides is that their active ingredient is sodium carbonate peroxyhydrate ($2Na_2CO_3.3H_2O_2$). These would add $Na^+$ to culture water and could be problematic for water recycling over time because unavoidable evaporative losses tend to increase dissolved salt concentrations in large-scale algal. $Na^+$ accumulation could be avoided, however, with new $H_2O_2$-based algaecides that use $K^+$ as counter-ion instead of $Na^+$. K is a macronutrient for plants and algae and would be rapidly consumed in large-scale algal cultures by algal growth. Similarly, accumulation of carbonate ($CO_3$) ion from use of $2K_2CO_3.3H_2O_2$ could be problematic but injection of carbon dioxide gas ($CO_2$) for pH management, already common in algal biomass production systems, would tend to convert $CO_3$ to dissolved bicarbonate ion ($HCO_3^-$) and $CO_2$, both of which are consumed by algal photosynthesis. Thus, with simple adjustments to their formulation, $H_2O_2$-based algaecides could be applied at relatively high rates to treat pests in large-scale algal cultures or to clean equipment and leave no long-term residues at all, though for a short time after use, $H_2O_2$ levels in the water would be high.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate embodiment of the invention.

Moreover, though the description of the invention has included description of one or more embodiments and certain variations and modifications, other variations and modifications are within the scope of the invention (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

We claim:

1. A DNA construct wherein said DNA construct comprises a promoter and a hydrogen peroxide resistance protein coding sequence,
    wherein said promoter comprises SEQ ID NO: 14, SEQ ID NO:15, SEQ ID NO:16, and SEQ ID NO:17,
    wherein said hydrogen resistance protein coding sequence is a catalase protein coding sequence, wherein the catalase protein coding sequence is SEQ ID NO:3, and
    wherein said promoter is operably linked to said hydrogen peroxide resistance protein coding sequence.

2. The DNA construct of claim 1, wherein the DNA construct further comprises a translation regulator operably linked to the 3' end of said promoter.

3. The DNA construct of claim 2, wherein said translation regulator comprises SEQ ID NO:11.

4. A transgenic unicellular organism of the order Chlamydomonadales having a DNA construct comprising a hydrogen peroxide resistance protein, wherein said DNA construct is the construct of claim 1 and is stably integrated into a unicellular genome of said transgenic unicellular organism under conditions suitable for the expression of said hydrogen peroxide resistance protein in a cell wall, cell membrane, cytosol or organelle of said transgenic unicellular organism.

5. A transgenic unicellular organism of the order Chlamydomonadales having a DNA construct comprising a hydrogen peroxide resistance protein, wherein said DNA construct is the construct of claim 2, wherein said DNA construct is stably integrated into a unicellular genome of said transgenic unicellular organism under conditions suitable for the expression of said hydrogen peroxide resistance protein in a cell wall, cell membrane, cytosol or organelle of said transgenic unicellular organism.

6. A transgenic unicellular organism of the order Chlamydomonadales having a DNA construct comprising a hydrogen peroxide resistance protein, wherein said DNA construct is the construct of claim 3, wherein said DNA construct is stably integrated into a unicellular genome of said transgenic unicellular organism under conditions suitable for the expression of said hydrogen peroxide resistance protein in a cell wall, cell membrane, cytosol or organelle of said transgenic unicellular organism.

7. A method for producing hydrogen peroxide resistance proteins in a cell wall, a cell membrane or an organelle of a unicellular organism which comprises growing a unicellular organism of the order Chlamydomonadales having said DNA construct of claim 1 stably integrated into a genome under conditions suitable for an expression of the DNA construct in a cellular organism, wherein the DNA construct expresses a protein in said cell wall, said cell membrane, said cytosol or said organelle of said unicellular organism, wherein the expressed protein is a hydrogen peroxide resistance protein.

8. A method for producing hydrogen peroxide resistance proteins in a cell wall, a cell membrane or an organelle of a unicellular organism which comprises growing a unicellular organism of the order Chlamydomonadales having said DNA construct of claim 2 stably integrated into a genome under conditions suitable for an expression of the DNA construct in a cellular organism, wherein the DNA construct expresses a protein in said cell wall, said cell membrane, said cytosol or said organelle of said unicellular organism, wherein the expressed protein is a hydrogen peroxide resistance protein.

9. A method for producing hydrogen peroxide resistance proteins in a cell wall, a cell membrane or an organelle of a unicellular organism which comprises growing a unicellular organism of the order Chlamydomonadales having said DNA construct of claim 3 stably integrated into a genome under conditions suitable for an expression of the DNA construct in a cellular organism, wherein the DNA construct expresses a protein in said cell wall, said cell membrane, said cytosol or said organelle of said unicellular organism, wherein the expressed protein is a hydrogen peroxide resistance protein.

10. A DNA construct wherein said DNA construct comprises a promoter and a hydrogen peroxide resistance protein coding sequence,
wherein said promoter comprises SEQ ID NO: 14, SEQ ID NO:15, SEQ ID NO:16, and SEQ ID NO:17,
wherein said hydrogen resistance protein coding sequence is a catalase protein coding sequence, wherein the catalase protein coding sequence is SEQ ID NO:4; and
wherein said promoter is operably linked to said hydrogen peroxide resistance protein coding sequence.

11. The DNA construct of claim 10, wherein the DNA construct further comprises a translation regulator operably linked to the 3' end of said promoter.

12. The DNA construct of claim 11, wherein said translation regulator comprises SEQ ID NO:11.

13. A transgenic unicellular organism of the order Chlamydomonadales having a DNA construct comprising a hydrogen peroxide resistance protein, wherein said DNA construct is the construct of claim 10 and is stably integrated into a unicellular genome of said transgenic unicellular organism under conditions suitable for the expression of said hydrogen peroxide resistance protein in a cell wall, cell membrane, cytosol or organelle of said transgenic unicellular organism.

14. A transgenic unicellular organism of the order Chlamydomonadales having a DNA construct comprising a hydrogen peroxide resistance protein, wherein said DNA construct is the construct of claim 11, wherein said DNA construct is stably integrated into a unicellular genome of said transgenic unicellular organism under conditions suitable for the expression of said hydrogen peroxide resistance protein in a cell wall, cell membrane, cytosol or organelle of said transgenic unicellular organism.

15. A transgenic unicellular organism of the order Chlamydomonadales having a DNA construct comprising a hydrogen peroxide resistance protein, wherein said DNA construct is the construct of claim 12, wherein said DNA construct is stably integrated into a unicellular genome of said transgenic unicellular organism under conditions suitable for the expression of said hydrogen peroxide resistance protein in a cell wall, cell membrane, cytosol or organelle of said transgenic unicellular organism.

16. A method for producing hydrogen peroxide resistance proteins in a cell wall, a cell membrane or an organelle of a unicellular organism which comprises growing a unicellular organism of the order Chlamydomonadales having said DNA construct of claim 10 stably integrated into a genome under conditions suitable for an expression of the DNA construct in a cellular organism, wherein the DNA construct expresses a protein in said cell wall, said cell membrane, said cytosol or said organelle of said unicellular organism, wherein the expressed protein is a hydrogen peroxide resistance protein.

17. A method for producing hydrogen peroxide resistance proteins in a cell wall, a cell membrane or an organelle of a unicellular organism which comprises growing a unicellular organism of the order Chlamydomonadales having said DNA construct of claim 11 stably integrated into a genome under conditions suitable for an expression of the DNA construct in a cellular organism, wherein the DNA construct expresses a protein in said cell wall, said cell membrane, said cytosol or said organelle of said unicellular organism, wherein the expressed protein is a hydrogen peroxide resistance protein.

18. A method for producing hydrogen peroxide resistance proteins in a cell wall, a cell membrane or an organelle of a unicellular organism which comprises growing a unicellular organism of the order Chlamydomonadales having said DNA construct of claim 12 stably integrated into a genome under conditions suitable for an expression of the DNA construct in a cellular organism, wherein the DNA construct expresses a protein in said cell wall, said cell membrane, said cytosol or said organelle of said unicellular organism, wherein the expressed protein is a hydrogen peroxide resistance protein.

* * * * *